(12) United States Patent
Berlowitz et al.

(10) Patent No.: US 9,786,939 B2
(45) Date of Patent: Oct. 10, 2017

(54) INTEGRATED POWER GENERATION AND CHEMICAL PRODUCTION USING FUEL CELLS

(71) Applicants: Paul J. Berlowitz, Glen Gardner, NJ (US); Timothy Andrew Barckholtz, Whitehouse Station, NJ (US); Frank Hershkowitz, Basking Ridge, NJ (US)

(72) Inventors: Paul J. Berlowitz, Glen Gardner, NJ (US); Timothy Andrew Barckholtz, Whitehouse Station, NJ (US); Frank Hershkowitz, Basking Ridge, NJ (US)

(73) Assignee: ExxonMobil Research and Engineering Company, Annandale, NJ (US)

(*) Notice: Subject to any disclaimer, the term of this patent is extended or adjusted under 35 U.S.C. 154(b) by 741 days.

(21) Appl. No.: 14/207,693

(22) Filed: Mar. 13, 2014

(65) Prior Publication Data

US 2014/0272634 A1     Sep. 18, 2014

Related U.S. Application Data

(60) Provisional application No. 61/788,628, filed on Mar. 15, 2013, provisional application No. 61/787,587, (Continued)

(51) Int. Cl.
*H01M 8/06* (2016.01)
*F02C 3/22* (2006.01)
(Continued)

(52) U.S. Cl.
CPC .............. *H01M 8/06* (2013.01); *C01B 3/16* (2013.01); *C01B 3/34* (2013.01); *C01B 3/48* (2013.01);
(Continued)

(58) Field of Classification Search
CPC ...... H01M 8/06; H01M 8/04; H01M 8/04111; H01M 8/0612; H01M 8/04156;
(Continued)

(56) References Cited

U.S. PATENT DOCUMENTS 3,615,839 A   10/1971   Thompson et al.
3,970,474 A   7/1976    Anbar et al.
(Continued)

FOREIGN PATENT DOCUMENTS

CA   2120858 A1    10/1994
CA   23250702 A1   4/2002
(Continued)

OTHER PUBLICATIONS

Cavallaro et al., "Syngas and electricity production by an integrated autothermal reforming/molten carbonate fuel cell system", Journal of Power Sources, Dec. 1, 1988 pp. 190-196, vol. 76, No. 2, Elsevier.

(Continued)

*Primary Examiner* — Lisa S Park

(57) ABSTRACT

In various aspects, systems and methods are provided for operating a molten carbonate fuel cell assembly at increased power density. This can be accomplished in part by performing an effective amount of an endothermic reaction within the fuel cell stack in an integrated manner. This can allow for increased power density while still maintaining a desired temperature differential within the fuel cell assembly.

18 Claims, 8 Drawing Sheets

Related U.S. Application Data filed on Mar. 15, 2013, provisional application No. 61/787,697, filed on Mar. 15, 2013, provisional application No. 61/787,879, filed on Mar. 15, 2013, provisional application No. 61/884,376, filed on Sep. 30, 2013, provisional application No. 61/884,545, filed on Sep. 30, 2013, provisional application No. 61/884,565, filed on Sep. 30, 2013, provisional application No. 61/884,586, filed on Sep. 30, 2013, provisional application No. 61/884,605, filed on Sep. 30, 2013, provisional application No. 61/884,635, filed on Sep. 30, 2013, provisional application No. 61/889,757, filed on Oct. 11, 2013.

(51) Int. Cl.

| | | |
|---|---|---|
| H01M 8/04 | (2016.01) | |
| H01M 8/04089 | (2016.01) | |
| H01M 8/04746 | (2016.01) | |
| H01M 8/0612 | (2016.01) | |
| H01M 8/0637 | (2016.01) | |
| C21B 15/00 | (2006.01) | |
| C04B 7/36 | (2006.01) | |
| H01M 8/0668 | (2016.01) | |
| H01M 8/0662 | (2016.01) | |
| H01M 8/04791 | (2016.01) | |
| H01M 8/04119 | (2016.01) | |
| C01B 3/50 | (2006.01) | |
| C07C 29/151 | (2006.01) | |
| C10G 2/00 | (2006.01) | |
| C07C 1/04 | (2006.01) | |
| C10K 3/04 | (2006.01) | |
| H01M 8/04111 | (2016.01) | |
| C01B 3/16 | (2006.01) | |
| C25B 3/02 | (2006.01) | |
| C01B 3/34 | (2006.01) | |
| C01B 3/48 | (2006.01) | |
| C07C 29/152 | (2006.01) | |
| F02C 6/18 | (2006.01) | |
| H01M 8/14 | (2006.01) | |

(52) U.S. Cl.
CPC ............. *C01B 3/50* (2013.01); *C04B 7/367* (2013.01); *C07C 1/0485* (2013.01); *C07C 29/152* (2013.01); *C07C 29/1518* (2013.01); *C10G 2/32* (2013.01); *C10G 2/332* (2013.01); *C10G 2/34* (2013.01); *C10K 3/04* (2013.01); *C21B 15/00* (2013.01); *C25B 3/02* (2013.01); *F02C 3/22* (2013.01); *F02C 6/18* (2013.01); *H01M 8/04* (2013.01); *H01M 8/04097* (2013.01); *H01M 8/04111* (2013.01); *H01M 8/04156* (2013.01); *H01M 8/04761* (2013.01); *H01M 8/04805* (2013.01); *H01M 8/0612* (2013.01); *H01M 8/0618* (2013.01); *H01M 8/0625* (2013.01); *H01M 8/0631* (2013.01); *H01M 8/0637* (2013.01); *H01M 8/0662* (2013.01); *H01M 8/0668* (2013.01); *H01M 8/0687* (2013.01); *H01M 8/14* (2013.01); *H01M 8/141* (2013.01); *H01M 8/145* (2013.01); *C01B 2203/00* (2013.01); *C01B 2203/02* (2013.01); *C01B 2203/0205* (2013.01); *C01B 2203/0227* (2013.01); *C01B 2203/0233* (2013.01); *C01B 2203/0283* (2013.01); *C01B 2203/04* (2013.01); *C01B 2203/0405* (2013.01); *C01B 2203/046* (2013.01); *C01B 2203/0415* (2013.01); *C01B 2203/0475* (2013.01); *C01B 2203/0495* (2013.01); *C01B 2203/061* (2013.01); *C01B 2203/062* (2013.01); *C01B 2203/066* (2013.01); *C01B 2203/067* (2013.01); *C01B 2203/1241* (2013.01); *C01B 2203/148* (2013.01); *C01B 2203/84* (2013.01); *C01B 2203/86* (2013.01); *C04B 2290/20* (2013.01); *C21B 2300/02* (2013.01); *H01M 2008/147* (2013.01); *H01M 2250/10* (2013.01); *H01M 2250/407* (2013.01); *H01M 2300/0051* (2013.01); *Y02B 90/14* (2013.01); *Y02E 20/14* (2013.01); *Y02E 20/16* (2013.01); *Y02E 20/185* (2013.01); *Y02E 50/18* (2013.01); *Y02E 60/50* (2013.01); *Y02E 60/526* (2013.01); *Y02E 60/563* (2013.01); *Y02E 60/566* (2013.01); *Y02P 10/132* (2015.11); *Y02P 20/129* (2015.11); *Y02P 20/13* (2015.11); *Y02P 30/30* (2015.11); *Y02P 70/56* (2015.11); *Y02T 10/16* (2013.01)

(58) Field of Classification Search
CPC ........ H01M 8/04805; C01B 3/34; C01B 3/16; C01B 3/50; C10G 2/332; C10G 2/32; C25B 3/02; C10K 3/04; C07C 1/0485; C07C 29/1518

See application file for complete search history.

(56) References Cited

U.S. PATENT DOCUMENTS

| | | | |
|---|---|---|---|
| 4,041,210 | A | 8/1977 | Van Dine |
| 4,160,663 | A | 7/1979 | Hsieh |
| 4,772,634 | A | 9/1988 | Farooque |
| 4,810,595 | A | 3/1989 | Kahara et al. |
| 4,917,971 | A | 4/1990 | Farooque |
| 4,921,765 | A | 5/1990 | Geisbrecht et al. |
| 4,995,807 | A | 2/1991 | Rampley et al. |
| 5,039,579 | A | 8/1991 | Kinoshita |
| 5,071,719 | A | 12/1991 | Rostrup-Nielsen et al. |
| 5,079,103 | A | 1/1992 | Schramm |
| 5,082,752 | A | 1/1992 | Koga et al. |
| 5,084,362 | A | 1/1992 | Farooque |
| 5,134,043 | A | 7/1992 | Nakazawa |
| 5,169,717 | A | 12/1992 | Topsoe |
| 5,198,311 | A | 3/1993 | Nakazawa et al. |
| 5,208,113 | A | 5/1993 | Kinoshita |
| 5,232,793 | A | 8/1993 | Miyauchi et al. |
| 5,348,814 | A * | 9/1994 | Niikura ............... H01M 8/0625 429/423 |
| 5,380,600 | A | 1/1995 | Hansen et al. |
| 5,413,878 | A | 5/1995 | Williams et al. |
| 5,417,051 | A | 5/1995 | Ankersmit et al. |
| 5,422,195 | A | 6/1995 | Bernard |
| 5,470,670 | A | 11/1995 | Yasumoto et al. |
| 5,541,014 | A | 7/1996 | Micheli et al. |
| 5,554,453 | A | 9/1996 | Steinfeld et al. |
| 5,616,430 | A | 4/1997 | Aoyama |
| 5,736,026 | A | 4/1998 | Patel et al. |
| 5,833,734 | A | 11/1998 | Cip et al. |
| 6,090,312 | A | 7/2000 | Ziaka et al. |
| 6,126,718 | A | 10/2000 | Sawa et al. |
| 6,162,556 | A * | 12/2000 | Vollmar ............... H01M 8/0612 429/411 |
| 6,267,799 | B1 | 7/2001 | Innes et al. |
| 6,322,916 | B1 | 11/2001 | Hemmes et al. |
| 6,365,290 | B1 | 4/2002 | Ghezel-Ayagh et al. |
| 6,383,251 | B1 | 5/2002 | Sherwood |
| 6,524,356 | B2 | 2/2003 | Fournier et al. |
| 6,648,942 | B2 | 11/2003 | Hoffman et al. |
| 6,896,988 | B2 | 5/2005 | Wang et al. |
| 7,311,986 | B2 | 12/2007 | Hsu |
| 7,396,603 | B2 | 7/2008 | Farooque et al. |
| 7,563,527 | B2 | 7/2009 | Tanaka et al. |
| 7,862,938 | B2 | 1/2011 | Ghezel-Ayagh |

(56) References Cited

U.S. PATENT DOCUMENTS

| | | |
|---|---|---|
| 7,914,765 B2 | 3/2011 | McLean et al. |
| 8,047,007 B2 | 11/2011 | Zubrin et al. |
| 8,080,344 B2 | 12/2011 | Skok et al. |
| 8,142,943 B2 | 3/2012 | McElroy et al. |
| 8,349,504 B1 | 1/2013 | Radovich |
| 8,562,903 B2 | 10/2013 | Hayton et al. |
| 2002/0142208 A1 | 10/2002 | Keefer et al. |
| 2003/0008183 A1 | 1/2003 | Hsu |
| 2003/0143448 A1* | 7/2003 | Keefer .................. B01D 53/08 429/9 |
| 2004/0038089 A1 | 2/2004 | Hoffman et al. |
| 2004/0202914 A1 | 10/2004 | Sridhar et al. |
| 2005/0079395 A1 | 4/2005 | Varatharajan et al. |
| 2005/0106429 A1 | 5/2005 | Keefer |
| 2005/0112425 A1 | 5/2005 | Hsu |
| 2005/0123810 A1* | 6/2005 | Balan .................. C01B 3/501 429/411 |
| 2005/0164051 A1 | 7/2005 | Venkataraman et al. |
| 2005/0181247 A1 | 8/2005 | Foger et al. |
| 2005/0271914 A1 | 12/2005 | Farooque et al. |
| 2006/0127718 A1 | 6/2006 | Kurashima et al. |
| 2006/0159967 A1 | 7/2006 | Huijsmans et al. |
| 2006/0251940 A1 | 11/2006 | Bamdjaier et al. |
| 2007/0017367 A1 | 1/2007 | McElroy et al. |
| 2007/0072027 A1 | 3/2007 | Sridhar et al. |
| 2007/0099038 A1 | 5/2007 | Galloway |
| 2007/0184310 A1 | 8/2007 | Kim et al. |
| 2007/0224467 A1 | 9/2007 | Nervi et al. |
| 2007/0287046 A1 | 12/2007 | Koda et al. |
| 2008/0057361 A1 | 3/2008 | Moon et al. |
| 2008/0160358 A1 | 7/2008 | Parodi et al. |
| 2009/0042070 A1 | 2/2009 | Brown, Jr. et al. |
| 2009/0169452 A1 | 7/2009 | Constantz et al. |
| 2009/0186244 A1* | 7/2009 | Mayer ................. H01M 8/0295 429/2 |
| 2009/0208784 A1 | 8/2009 | Perry et al. |
| 2009/0317667 A2 | 12/2009 | Nervi et al. |
| 2009/0317669 A1 | 12/2009 | Hildebrandt et al. |
| 2010/0015486 A1 | 1/2010 | Yoshiba |
| 2010/0148410 A1 | 6/2010 | Bleifuss et al. |
| 2010/0239924 A1 | 9/2010 | McElroy et al. |
| 2011/0104577 A1 | 5/2011 | Cui et al. |
| 2011/0111315 A1 | 5/2011 | Cui et al. |
| 2011/0117460 A1 | 5/2011 | Shin |
| 2011/0154951 A1 | 6/2011 | Hiraoka |
| 2011/0167821 A1 | 7/2011 | Baker et al. |
| 2011/0171544 A1 | 7/2011 | Burmeister et al. |
| 2011/0223500 A1 | 9/2011 | Uematsu et al. |
| 2011/0223501 A1 | 9/2011 | Uematsu et al. |
| 2012/0028145 A1 | 2/2012 | Boden et al. |
| 2012/0171588 A1 | 7/2012 | Fan et al. |
| 2012/0214076 A1 | 8/2012 | Hakala |
| 2012/0251898 A1 | 10/2012 | Lehar et al. |
| 2012/0325053 A1 | 12/2012 | Grossi |
| 2013/0014484 A1 | 1/2013 | Caprile et al. |
| 2013/0081516 A1 | 4/2013 | Simmons |
| 2013/0177824 A1 | 7/2013 | Cui et al. |
| 2013/0209904 A1 | 8/2013 | Liu et al. |

FOREIGN PATENT DOCUMENTS

| | | |
|---|---|---|
| CN | 101098022 A | 1/2008 |
| CN | 201902241 U | 7/2011 |
| CN | 2694153 A1 | 9/2011 |
| DE | 4005468 A1 | 8/1991 |
| DE | 19515669 A1 | 10/1996 |
| DE | 19545186 A1 | 6/1997 |
| DE | 19941724 A1 | 8/2000 |
| DE | 10016847 A1 | 10/2001 |
| EP | 0170277 A2 | 5/1986 |
| EP | 0473153 A2 | 4/1992 |
| EP | 1926171 A1 | 5/2008 |
| JP | 56069775 A | 6/1981 |
| JP | H05163180 A | 6/1993 |
| JP | 08096824 A | 4/1996 |
| JP | 10172595 A | 6/1999 |
| JP | 11191427 A | 7/1999 |
| JP | 11312527 A | 11/1999 |
| JP | 2002319248 A | 10/2002 |
| JP | 2004014124 A | 1/2004 |
| JP | 2004079495 A | 3/2004 |
| JP | 2004186074 A | 7/2004 |
| JP | 2006073316 A | 3/2006 |
| JP | 2007287580 A | 11/2007 |
| JP | 2008192425 A | 8/2008 |
| JP | 2008287940 A | 11/2008 |
| JP | 2009043487 A | 2/2009 |
| JP | 2013045535 A1 | 3/2013 |
| KR | 100651270 B1 | 11/2006 |
| KR | 100827954 B1 | 5/2008 |
| KR | 20090067426 A | 6/2009 |
| KR | 20090124824 A | 12/2009 |
| KR | 20110029963 A | 3/2011 |
| KR | 20110032443 A | 3/2011 |
| KR | 101032974 B1 | 5/2011 |
| KR | 20110077775 A | 7/2011 |
| KR | 20120050319 A | 5/2012 |
| NL | 1008883 C2 | 10/1999 |
| WO | 9733828 A1 | 9/1997 |
| WO | 02069430 A2 | 9/2002 |
| WO | 02070402 A2 | 9/2002 |
| WO | 02103833 A1 | 12/2002 |
| WO | 03063276 A2 | 7/2003 |
| WO | 2004013924 A2 | 2/2004 |
| WO | 2005001977 A1 | 1/2005 |
| WO | 2008036169 A2 | 3/2008 |
| WO | 2010044113 A1 | 4/2010 |
| WO | 2010067223 A1 | 6/2010 |
| WO | 2010125443 A1 | 11/2010 |
| WO | 2010147885 A1 | 12/2010 |
| WO | 2010147886 A1 | 12/2010 |
| WO | 2011077224 A1 | 6/2011 |
| WO | 2012091096 A1 | 7/2012 |
| WO | 2012176176 A1 | 12/2012 |
| WO | 2012176177 A1 | 12/2012 |

OTHER PUBLICATIONS

Appleby et al., "Current Technology of PAFC, MCFC and SOFC Systems: Status of Present Fuel Cell Power Plants", Electrochemical Hydrogen Technologies, Electrochemical Production and Combustion of Hydrogen, Jan. 1, 1990, pp. 425-495, Elsevier.

Appleby, "Fuel Cells and Hydrogen Fuel", International Journal of Hydrogen Energy, Feb. 1, 1994, pp. 175-180 vol. 19, No. 2, International Association for Hydrogen Energy, Pergamon Press Ltd., Great Britain.

Chiesa et al., "A Comparative Analysis of IGCCs with CO2 Sequestration", In: Proceedings of 4th International Conference on Greenhouse Gas Control Technologies, Interlaken, Switzerland Aug. 30, 1998-Sep. 2, 1998, pp. 107-112.

Amorelli et al., "An experimental investigation into the use of molten carbonate fuel cells to capture CO2 from gas turbine exhaust gases", 2nd annual conference on Carbon Seqquestration, May 5, 2003 to May 8, 2003, Hilton Alexandria Mark Center, Alexandria, VA.

Sugiura et al., "The carbon dioxide concentrator by using MCFC", Journal of Power Sources, May 25, 2003, pp. 218-227, vol. 118, No. 1-2, ScienceDirect, Elsevier.

Steynberg et al., eds., "Gas loop for POX reformers", Studies in Surface Science and Catalysis: Fischer Tropsch Technology, Jul. 28, 2004, vol. 152, p. 432, fig. 8, Elsevier B.V.

Verda et al., "Thermodynamic and economic optimization of a MCFC-based hybrid system for the combined production of electricity and hydrogen". International Journal of Hydrogen Energy, Jan. 1, 2010, vol. 35, No. 2, pp. 794-806, ScienceDirect, Elsevier.

Campanari et al., "CO2 capture from combined cycles integrated with Molten Carbonate Fuel Cells", International Journal of Greenhouse Gas Control, May 1, 2010, pp. 441-451, vol. 4, No. 3, Greenhouse Gas Control, ScienceDirect, Elsevier.

(56) References Cited

OTHER PUBLICATIONS

Kim et al., "Numerical studies of a separator for stack temperature control in a molten carbonate fuel cell", International Journal of Hydrogen Energy, Apr. 7, 2011, vol. 36, No. 14, pp. 8499-8507, ScienceDirect, Elsevier.
Pilatowski et al., "Thermodynamics of Fuel Cells", Cogeneration Fuel Cell-Sorption Air Conditioning Systems, Jun. 2, 2011, pp. 25-36, Springer.
Lowe et al., "Technology Assessment of Hydrogen Firing of Process Heaters", Energy Procedia, Jul. 1, 2011, pp. 1058-1065, vol. 4, ScienceDirect, Elsevier.
Appl, "Ammonia, 3. Production Plants", Ullmann's Encyclopedia of Industrial Chemistry, Oct. 15, 2011, vol. 3, Wiley-Verlag GmbH & Co., Weinheim.
Anonymous, "Lower and Higher Heating Values of Fuels", Hydrogen Data Resource Center: Hydrogen Calculator, Jan. 1, 2012, U.S. Dept. of Energy.
Giddey et al., "A comprehensive review of direct carbon fuel cell technology", Progress in Energy Combustion Science, Jan. 28, 2012, pp. 360-399, vol. 38, No. 3, Science Direct, Elsevier.
Anonymous, "Heat of Combustion", Wikipedia, the free Encyclopedia, Jun. 6, 2014.
International Search Report with Written Opinion from PCT/US2014/025173 dated Jun. 13, 2014.
International Search Report with Written Opinion from PCT/US2014/025214 dated Jul. 4, 2014.
International Search Report with Written Opinion from PCT/US2014/025228 dated Jul. 4, 2014.
International Search Report with Written Opinion from PCT/US2014/025237 dated Jul. 4, 2014.
International Search Report with Written Opinion from PCT/US2014/025181 dated Jul. 7, 2014.
International Search Report with Written Opinion from PCT/US2014/025186 dated Jul. 7, 2014.
International Search Report with Written Opinion from PCT/US2014/025189 dated Jul. 7, 2014.
International Search Report with Written Opinion from PCT/US2014/025240 dated Jul. 8, 2014.
International Search Report with Written Opinion from PCT/US2014/025216 dated Jul. 15, 2014.
International Search Report with Written Opinion from PCT/US2014/025223 dated Jul. 15, 2014.
International Search Report with Written Opinion from PCT/US2014/025192 dated Jul. 22, 2014.
International Search Report with Written Opinion from PCT/US2014/025208 dated Jul. 22, 2014.
International Search Report with Written Opinion from PCT/US2014/025195 dated Jul. 24, 2014.
International Search Report with Written Opinion from PCT/US2014/025180 dated Jul. 28, 2014.
International Search Report with Written Opinion from PCT/US2014/025175 dated Jul. 28, 2014.
International Search Report with Written Opinion from PCT/US2014/025185 dated Jul. 28, 2014.
International Search Report with Written Opinion from PCT/US2014/025212 dated Jul. 28, 2014.
International Search Report with Written Opinion from PCT/US2014/025179 dated Aug. 5, 2014.
International Search Report with Written Opinion from PCT/US2014/025229 dated Aug. 5, 2014.
Partial International Search Report from PCT/US2014/025188 dated Aug. 29, 2014.
Partial International Search Report from PCT/US2014/025219 dated Aug. 29, 2014.
International Search Report with Written Opinion from PCT/US2014/025203 dated Sep. 1, 2014.
Avidan, "Gasoline and Distillate Fuels from Methanol", Studies in Surface Science and Catalysis, 1988, vol. 36, pp. 307-323, Methane Conversion, Elsevier Science Publishers B.V., Amsterdam.
Keil, "Methanol-to-hydrocarbons: process technology" Microporous and Mesoporous Materials, Jun. 1999, vol. 29 (1-2), pp. 49-66, Elsevier.
Campanari, "Carbon Dioxide separation from high temperature fuel cell power plants", Journal of Power Sources, 2002, vol. 112, pp. 273-289, Science Direct, Elsevier.
Amorelli et al., "An experimental investigation into the use of molten carbonate fuel cells to capture $CO_2$ from gas turbine exhaust gases", Energy, 2004, vol. 29, pp. 1279-1284, Science Direct, Elsevier.
Naqvi, "Dimethyl Ether as Fuel", SRI Consulting Report, Report No. 245A, Sep. 2005, Process Economics Program, Menlo Park, CA.
Greenhouse Gas Technology Center, "Test and Quality Assurance Plan: FuelCell Energy, Inc.—DFC 300A Molten Carbonate Fuel Cell Combined Heat and Power System" SRI/USEPA, Mar. 2007, pp. 1-42, Southern Research Institute, Morrisville, NC.
Abu-Zahra et al.,"$CO_2$ capture from power plants Part I: A parametric study of the technical performance based on monoethanolamine", International Journal of Greenhouse Gas Control, 2007, vol. 1, pp. 37-46, ScienceDirect, Elsevier.
"Molten Carbonate Fuel Cell Technology", Fossil Energy Office of Communications, Jan. 11, 2011, U.S. Department of Energy.
Campanari et al., "Application of MCFCs for active $CO_2$ capture within natural gas combine cycles" Energy Procedia, 2011, vol. 4, pp. 1235-1242, Science Direct, Elsevier.
Caprile, "Carbon capture: Energy wasting technologies or the MCFCs challenge?", International Journal of Hydrogen Energy, 2011, vol. 36, pp. 10269-10277, Science Direct, Elsevier.
Chiesa et al., "$CO_2$ cryagenic separation from combined cycles integrated with molten carbonate fuel cells", International Journal of Hydrogen Energy, 2011, vol. 36, pp. 10355-10365, Science Direct, Elsevier.
Wesoff, "Will FuelCell Energy Be the First Profitable Company in the Industry?", Greentech Media, Dec. 15, 2011.
Manzolini et al., "$CO_2$ Separation from Combined Cycles Using Molten Carbonate Fuel Cells," Journal of Fuel Cell Science and Technology, Feb. 2012, pp. 011018-1 to 011018-8, vol. 9, iss. 1, American Society of Mechanical Engineers.
Zhou et al., "Decrease of energy demand for bioethanol-based polygeneration system through case study," Applied Energy, Mar. 6, 2012, vol. 95, pp. 305-311, Elsevier.
Ghezel-Ayagh, "Electrochemical Membrane for $CO_2$ Capture and Power Generation (No. DE-FE0007634)", presentation given at the 2012 NETL $CO_2$ Capture Technology Meeting, Jul. 9, 2012, Pittsburgh, PA.
Desideri, U., et al., "MCFC-based $CO_2$ capture system for small scale CHP plants," International Journal of Hydrogen Energy, Dec. 2012, pp. 19295-19303, vol. 37, iss. 24, SciVerse Science Direct, Elsevier.
Ghezel-Ayagh, "High Efficiency Direct FuelCell/Turbine® Power Plant", Project Fact Sheet for unit installed at the Billings Clinic in Billings, Montana, U.S. Department of Energy.
Office Action from related U.S. Appl. No. 14/315,419 dated Aug. 1, 2014.
Office Action from related U.S. Appl. No. 14/315,419 dated Jan. 27, 2015.
Office Action from related U.S. Appl. No. 14/315,439 dated Dec. 29, 2014.
Office Action from related U.S. Appl. No. 14/315,527 dated Jan. 9, 2015.
Office Action from related U.S. Appl. No. 14/315,479 dated Nov. 7, 2014.
International Search Report with Written Opinion from PCT/US2014/025188 dated Jan. 21, 2015.
International Search Report with Written Opinion from PCT/US2014/025219 dated Jan. 21, 2015.

* cited by examiner

INTEGRATED POWER GENERATION AND CHEMICAL PRODUCTION USING FUEL CELLS

CROSS-REFERENCE TO RELATED APPLICATIONS

This application claims the benefit of U.S. Ser. Nos. 61/787,587, 61/787,697, 61/787,879, and 61/788,628, all filed on Mar. 15, 2013, each of which is incorporated by reference herein in its entirety. This application also claims the benefit of U.S. Ser. Nos. 61/884,376, 61/884,545, 61/884,565, 61/884,586, 61/884,605, and 61/884,635, all filed on Sep. 30, 2013, each of which is incorporated by reference herein in its entirety. This application further claims the benefit of U.S. Ser. No. 61/889,757, filed on Oct. 11, 2013, which is incorporated by reference herein in its entirety.

This application is related to 4 other commonly assigned U.S. patent applications, filed on Mar. 5, 2014 as follows: Ser. Nos. 14/197,391; 14/197,430; 14/197,551; and Ser. No. 14/197,613. This application is also related to the following 21 commonly assigned U.S. patent applications, filed on Mar. 13, 2014: Ser Nos. 14/207,686; 14/207,686; 14/207,688 14/207,687; 14/207,690; 14/207,696; 14/207,698; 14/207,704; 14/207,706; 14/207,691; 14/207,699; 14/207,700; 14/207,705; 14/207,708; 14/207,711; 14/207,714; 14/207,710; 14/207,712; 14/207,721; 14/207,726; and 14/207,728. Each of these co-pending U.S. applications is hereby incorporated by reference herein in its entirety.

FIELD OF THE INVENTION

In various aspects, the invention is related to chemical production and/or power generation processes integrated with electrical power production using molten carbonate fuel cells.

BACKGROUND OF THE INVENTION

Molten carbonate fuel cells utilize hydrogen and/or other fuels to generate electricity. The hydrogen may be provided by reforming methane or other reformable fuels in a steam reformer that is upstream of the fuel cell or within the fuel cell. Reformable fuels can encompass hydrocarbonaceous materials that can be reacted with steam and/or oxygen at elevated temperature and/or pressure to produce a gaseous product that comprises hydrogen. Alternatively or additionally, fuel can be reformed in the anode cell in a molten carbonate fuel cell, which can be operated to create conditions that are suitable for reforming fuels in the anode. Alternately or additionally, the reforming can occur both externally and internally to the fuel cell.

Traditionally, molten carbonate fuel cells are operated to maximize electricity production per unit of fuel input, which may be referred to as the fuel cell's electrical efficiency. This maximization can be based on the fuel cell alone or in conjunction with another power generation system. In order to achieve increased electrical production and to manage the heat generation, fuel utilization within a fuel cell is typically maintained at 70% to 75%.

U.S. Published Patent Application 2011/0111315 describes a system and process for operating fuel cell systems with substantial hydrogen content in the anode inlet stream. The technology in the '315 publication is concerned with providing enough fuel in the anode inlet so that sufficient fuel remains for the oxidation reaction as the fuel approaches the anode exit. To ensure adequate fuel, the '315 publication provides fuel with a high concentration of $H_2$. The $H_2$ not utilized in the oxidation reaction is recycled to the anode for use in the next pass. On a single pass basis, the $H_2$ utilization may range from 10% to 30%. The '315 reference does not describe significant reforming within the anode, instead relying primarily on external reforming.

U.S. Published Patent Application 2005/0123810 describes a system and method for co-production of hydrogen and electrical energy. The co-production system comprises a fuel cell and a separation unit, which is configured to receive the anode exhaust stream and separate hydrogen. A portion of the anode exhaust is also recycled to the anode inlet. The operating ranges given in the '810 publication appear to be based on a solid oxide fuel cell. Molten carbonate fuel cells are described as an alternative.

U.S. Published Patent Application 2003/0008183 describes a system and method for co-production of hydrogen and electrical power. A fuel cell is mentioned as a general type of chemical converter for converting a hydrocarbon-type fuel to hydrogen. The fuel cell system also includes an external reformer and a high temperature fuel cell. An embodiment of the fuel cell system is described that has an electrical efficiency of about 45% and a chemical production rate of about 25% resulting in a system coproduction efficiency of about 70%. The '183 publication does not appear to describe the electrical efficiency of the fuel cell in isolation from the system.

U.S. Pat. No. 5,084,362 describes a system for integrating a fuel cell with a gasification system so that coal gas can be used as a fuel source for the anode of the fuel cell. Hydrogen generated by the fuel cell is used as an input for a gasifier that is used to generate methane from a coal gas (or other coal) input. The methane from the gasifier is then used as at least part of the input fuel to the fuel cell. Thus, at least a portion of the hydrogen generated by the fuel cell is indirectly recycled to the fuel cell anode inlet in the form of the methane generated by the gasifier.

An article in the Journal of Fuel Cell Science and Technology (G. Manzolini et. al., *J. Fuel Cell Sci. and Tech.*, Vol. 9, February 2012) describes a power generation system that combines a combustion power generator with molten carbonate fuel cells. Various arrangements of fuel cells and operating parameters are described. The combustion output from the combustion generator is used in part as the input for the cathode of the fuel cell. One goal of the simulations in the Manzolini article is to use the MCFC to separate $CO_2$ from the power generator's exhaust. The simulation described in the Manzolini article establishes a maximum outlet temperature of 660° C. and notes that the inlet temperature must be sufficiently cooler to account for the temperature increase across the fuel cell. The electrical efficiency (i.e. electricity generated/fuel input) for the MCFC fuel cell in a base model case is 50%. The electrical efficiency in a test model case, which is optimized for $CO_2$ sequestration, is also 50%.

An article by Desideri et al. (*Intl. J. of Hydrogen Energy*, Vol. 37, 2012) describes a method for modeling the performance of a power generation system using a fuel cell for $CO_2$ separation. Recirculation of anode exhaust to the anode inlet and the cathode exhaust to the cathode inlet are used to improve the performance of the fuel cell. The model parameters describe an MCFC electrical efficiency of 50.3%.

SUMMARY OF THE INVENTION

In an aspect, a method for operating a molten carbonate fuel cell is provided. The method includes introducing a fuel stream comprising reformable fuel into an anode inlet of a molten carbonate fuel cell; introducing a cathode inlet stream comprising $CO_2$ and $O_2$ into a cathode inlet of the fuel cell; operating the fuel cell at a first operating condition to generate electrical power and at least 100 mW/cm² of waste heat, the first operating condition providing a current density of at least about 150 mA/cm²; and performing an effective amount of an endothermic reaction to maintain a temperature differential between the anode inlet and an anode outlet of about 80° C. or less, such as about 60° C. or less.

In another aspect, a method for operating a molten carbonate fuel cell assembly is provided. The method includes introducing a fuel stream comprising reformable fuel into an anode inlet of a molten carbonate fuel cell; introducing a cathode inlet stream comprising $CO_2$ and $O_2$ into a cathode inlet of the fuel cell; operating the fuel cell at a first operating condition to generate electricity, the first operating condition providing a current density of at least about 150 mA/cm², the first operating condition having a corresponding baseline operating condition; and performing an effective amount of an endothermic reaction to maintain a temperature differential between the anode inlet and an anode outlet of about 80° C. or less, such as about 60° C. or less, wherein operating the fuel cell at the baseline operating condition would result in a temperature increase of at least about 100° C. between the anode inlet and the anode outlet, the baseline operating condition for the fuel cell assembly being defined as an operating condition that is the same as the first operating condition except that the baseline operating condition comprises a fuel utilization of about 75% and the fuel stream in the baseline operating condition comprises at least about 80 vol % of methane.

In still another aspect, a method for operating a molten carbonate fuel cell is provided. The method includes introducing a fuel stream comprising reformable fuel into an anode inlet of a molten carbonate fuel cell; introducing a cathode inlet stream comprising $CO_2$ and $O_2$ into a cathode inlet of the fuel cell; operating the fuel cell at a first operating condition to generate electrical power at a first power density and waste heat, the first operating condition comprising a first anode inlet temperature, a first anode inlet flow rate, a first anode fuel partial pressure, a first anode water partial pressure, a first cathode inlet flow rate, a first cathode $CO_2$ partial pressure, and a first cathode $O_2$ partial pressure, the first operating condition having a corresponding maximum power operating condition; and performing an effective amount of an endothermic reaction to maintain a temperature differential between the anode inlet and an anode outlet of about 80° C. or less, such as about 60° C. or less, wherein operating the fuel cell assembly at the maximum power operating condition would result in a power density that differs from the first power density by less than about 20%, the maximum power operating condition corresponding to an operating condition that generates the maximum power density for an operating condition that comprises the first anode inlet temperature, the first anode inlet flow rate, the first anode fuel partial pressure, the first anode water partial pressure, the first cathode inlet flow rate, the first cathode $CO_2$ partial pressure, and the first cathode $O_2$ partial pressure.

DETAILED DESCRIPTION OF THE EMBODIMENTS

Overview

Figure 1:
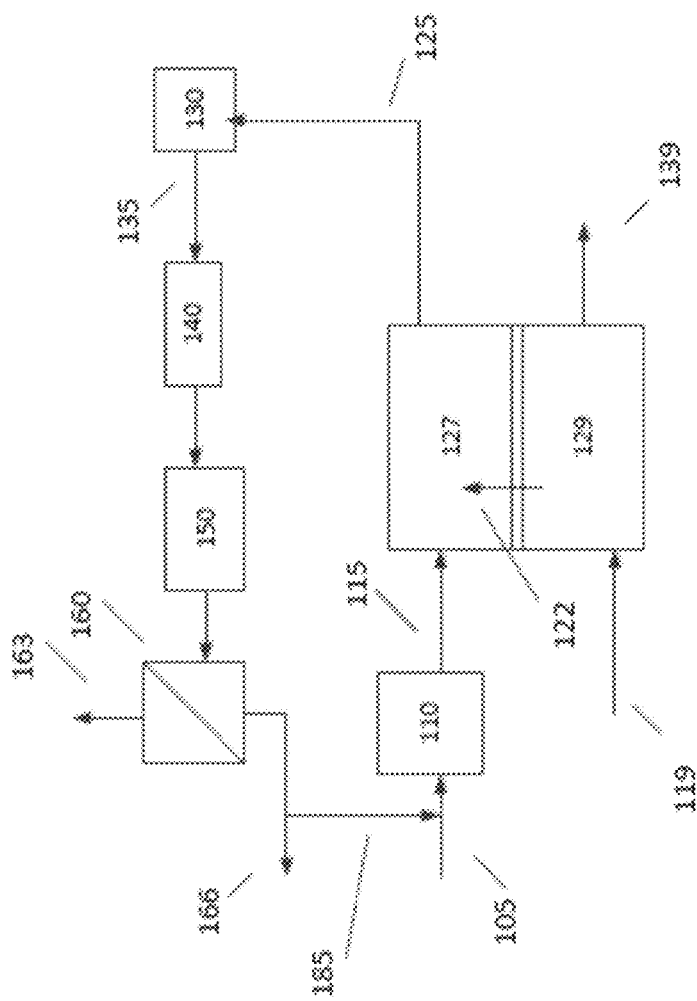
FIG. 1 schematically shows an example of a configuration for molten carbonate fuel cells and associated reforming and separation stages.

Prior art systems seek to maximize various parameters, most prominently electrical energy efficiency in the operation of molten carbonate fuel cell systems. This is typically employed when MCFC systems are used in stand-alone installations such as for distributed power or backup power generation. Heat production, for heating input anode and cathode streams to maintain appropriate fuel cell conditions can be done ex-situ, in-situ, or some combination thereof. Additional heat inputs to provide the thermal energy necessary to reform input fuel (such as methane) to hydrogen can be provided in various ways. This can result in a modest temperature increase across the fuel cell, with the effluent gasses providing sensible and chemical heat energy to input gasses to maintain steady integrated fuel cell system operation. As a result of this integrated operation, limits on the total amount of electrical power that result from the system can be a product of the desired high electrical efficiency and the capacity of the various reforming and heat exchange elements to absorb additional heat.

In various aspects, systems and methods are provided for operating a molten carbonate fuel cell at increased power density beyond conventional operation. Systems and methods according to such aspects can also form a hydrogen output stream, a syngas output stream, and/or another chemical product stream from an endothermic reaction, in addition to the electrical output generated beyond the typical heat-balanced operation. This can be accomplished by increasing the electrical power density of the fuel cell system (the product of the fuel cell voltage and current density per unit area). In doing so, the overall heat produced at the anode can be increased by the combination of both lower efficiency (i.e., lower voltage at greater current) and overall greater productivity. To compensate for this heat production, the fuel cell (and/or an integrated element or stage in a fuel cell stack) can perform an effective amount of an endothermic reaction. As one example, the fuel cell anode can perform an effective amount of reforming. As another example, an integrated endothermic reaction stage, such as a reforming stage and/or a stage for another type of endothermic reaction, can perform an effective amount of an endothermic reaction. Performing an effective amount of reforming or another endothermic reaction in a fuel cell anode and/or in an integrated stage can remove the limitation on operating a molten carbonate fuel cell due to the ability to transport away excess heat. Due to this limitation, and the objective of maintain high electrical efficiency, conventional molten carbonate fuel cells are typically not operated at the maximum power density for the fuel cell. Instead, a current density corresponding to a lower power density is typically used, so that the amount of waste heat can be appropriately managed.

In various aspects, rather than being limited by the amount of waste heat that can be transported away from the fuel cell system, the waste heat can be used as a heat source for the endothermic reaction integrated within the fuel cell assembly. This can require operations that do not seek to maintain integrated heat balance for the system as a whole, but that can convert the excess heat into useful chemical energy, such as in a syngas and/or hydrogen product stream. By performing an effective amount of the endothermic reaction, the overall electrical power density can be increased, and the range of potential electrical operations can be increased (i.e., the total range of electrical power outputs), while still maintaining a suitable temperature differential in a fuel cell. In some aspects, the amount of the endothermic reaction can be selected to have an endothermic heat requirement comparable to, or even greater than, the amount of waste heat generated by the exothermic reaction.

Conventionally, molten carbonate fuel cells have typically been operated to maximize the efficiency of electrical power generation relative to the amount of fuel consumed while maintaining overall system heat balance. In this type of operating condition, sufficient fuel is typically used to provide a) heat to maintain the fuel cell inlet at a desired temperature, and b) to provide sufficient hydrogen (usually after reforming of a reformable fuel) to generate electricity at a high fuel utilization value in the fuel cell. Due to the nature of molten carbonate fuel cells, practical considerations can prevent efficient generation of electricity at fuel utilizations within the fuel cell of more than about 70% or about 75%. To avoid loss of this fuel exiting the fuel cell anode, the anode output stream can conventionally be used as part of the fuel for providing heat to maintain the operating temperature of the fuel cell. In addition to using fuel for generating electrical energy, fuel can be burned for heat in order to maintain the carbonate electrolyte in a molten state.

Due to the nature of molten carbonate fuel cells, practical considerations prevent efficient generation of electricity at fuel utilizations within a fuel cell or fuel cell assembly of more than about 75%. These practical considerations are based in part on the exothermic nature of the fuel cell reaction for generation of electrical power. During conventional operation a fuel cell can have a temperature differential between the inlet of the fuel cell, such as the anode inlet, and the outlet of the fuel cell, such as the anode outlet. This temperature increase across the fuel cell during operation is the result of excess or waste heat from the exothermic reaction. Unfortunately, if the temperature differential across a fuel cell is too large, the structural integrity of the fuel cell can become compromised. In order to avoid this situation, molten carbonate fuel cells are conventionally operated to have a temperature differential of about 80° C. or less between anode inlet and anode outlet, such as about 50° C. or less.

Unfortunately, constraining a molten carbonate fuel cell to both operate at high fuel utilization and at a temperature differential of about 80° C. or less across the anode, such as about 50° C. or less, can also constrain the power density of the fuel cell, and thus constrain the dynamic range (turndown) and applicability of the system. The power density of a fuel cell corresponds to the actual operating voltage $V_A$ multiplied by the current density I. For a molten carbonate fuel cell operating at a voltage $V_A$, the fuel cell also can tend to generate waste heat, the waste heat defined as $(V_0-V_A)*I$ based on the differential between $V_A$ and the ideal voltage $V_0$ for a fuel cell providing current density I. A portion of this waste heat can be consumed by reforming of a reformable fuel within the anode of the fuel cell. The remaining portion of this waste heat can be absorbed by the surrounding fuel cell structures and gas flows, resulting in a temperature differential across the fuel cell. Under conventional operating conditions, the power density of a fuel cell can be limited based on the amount of waste heat that the fuel cell can tolerate without compromising the integrity of the fuel cell.

In various aspects, the amount of waste heat that a fuel cell can tolerate can be increased by performing an effective amount of an endothermic reaction within the fuel cell. One example of an endothermic reaction includes steam reforming of a reformable fuel within a fuel cell anode and/or in an associated reforming stage, such as an integrated reforming stage in a fuel cell stack. By providing additional reformable fuel to the anode of the fuel cell (or to an integrated/associated reforming stage), additional reforming can be performed so that additional waste heat can be consumed. This can reduce the amount of temperature differential across the fuel cell, thus allowing the fuel cell to operate under an operating condition with an increased amount of waste heat. The loss of electrical efficiency can be offset by the creation of an additional product stream, such as syngas and/or $H_2$, that can be used for various purposes including additional electricity generation further expanding the power range of the system.

For a reforming stage in a fuel cell stack that can be associated with an anode (such as associated with multiple anodes), a flow path can be available so that the output flow from the reforming stage is passed into at least one anode. This can correspond to having an initial section of a fuel cell plate not in contact with the electrolyte and instead can serve just as a reforming catalyst. Another option for an associated reforming stage can be to have a separate integrated reforming stage as one of the elements in a fuel cell stack, where the output from the integrated reforming stage can be returned to the input side of one or more of the fuel cells in the fuel cell stack.

From a heat integration standpoint, a characteristic height in a fuel cell stack can be the height of an individual fuel cell stack element. It is noted that the separate reforming stage and/or a separate endothermic reaction stage could have a different height in the stack than a fuel cell. In such a scenario, the height of a fuel cell element can be used as the characteristic height. In some aspects, an integrated endothermic reaction stage can be defined as a stage that is heat integrated with one or more fuel cells, so that the integrated endothermic reaction stage can use the heat from the fuel cells as a heat source for the endothermic reaction. Such an integrated endothermic reaction stage can be defined as being positioned less than 5 times the height of a stack element from any fuel cells providing heat to the integrated stage. For example, an integrated endothermic reaction stage (such as a reforming stage) can be positioned less than 5 times the height of a stack element from any fuel cells that are heat integrated, such as less than 3 times the height of a stack element. In this discussion, an integrated reforming stage and/or integrated endothermic reaction stage that represent an adjacent stack element to a fuel cell element can be defined as being about one stack element height or less away from the adjacent fuel cell element.

In aspects of the invention any convenient number and/or arrangement of integrated reaction stages can be provided within a fuel cell. For example, a fuel cell can comprise at least 1 integrated reaction stage for about every 100 stack elements within a fuel cell, such as about every 50 stack elements, or about every 30 stack elements, or about every 15 stack elements, or about every 10 stack elements, or about every 5 stack elements, or about every 3 stack elements, or about every 1 stack element. Additionally, integrated reaction stages can be arranged with different numbers of stack elements between different integrated reaction stages. For example, a first and a second integrated reaction stage can be separated by 5 stack elements, while the second and a third integrated reaction stage can be separated by 12 stack elements.

In some aspects, a separate reforming stage that is heat integrated with a fuel cell element can correspond to a reforming stage associated with the fuel cell element. In such aspects, an integrated fuel cell element can provide at least a portion of the heat to the associated reforming stage, and the associated reforming stage can provide at least a portion of the reforming stage output to the integrated fuel cell as a fuel stream. In other aspects, a separate reforming stage can be integrated with a fuel cell for heat transfer without being associated with the fuel cell. In this type of situation, the separate reforming stage can receive heat from the fuel cell, but the decision can be made not to use the output of the reforming stage as an input to the fuel cell. Instead, the decision can be made to use the output of such a reforming stage for another purpose, such as directly adding the output to the anode exhaust stream, and/or for forming a separate output stream from the fuel cell assembly.

More generally, a separate stack element in a fuel cell stack can be used to perform any convenient type of endothermic reaction that can take advantage of the waste heat provided by integrated fuel cell stack elements. Instead of plates suitable for performing a reforming reaction on a hydrocarbon fuel stream, a separate stack element can have plates suitable for catalyzing another type of endothermic reaction. A manifold or other arrangement of inlet conduits in the fuel cell stack can be used to provide an appropriate input flow to each stack element. A similar manifold or other arrangement of outlet conduits can additionally or alternately be used to withdraw the output flows from each stack element. Optionally, the output flows from an endothermic reaction stage in a stack can be withdrawn from the fuel cell stack without having the output flow pass through a fuel cell anode. In such an optional aspect, the products of the exothermic reaction can therefore exit from the fuel cell stack without passing through a fuel cell anode. Examples of other types of endothermic reactions that can be performed in stack elements in a fuel cell stack can include, without limitation, ethanol dehydration to form ethylene and ethane cracking.

In various aspects, the amount of waste heat generated by a fuel cell, $(V_O-V_A)*I$ as defined above, can be at least about 30 mW/cm$^2$, such as at least about 40 mW/cm$^2$, or at least about 50 mW/cm$^2$, or at least about 60 mW/cm$^2$, or at least about 70 mW/cm$^2$, or at least about 80 mW/cm$^2$, or at least about 100 mW/cm$^2$, or at least about 120 mW/cm$^2$, or at least about 140 mW/cm$^2$, or at least about 160 mW/cm$^2$, or at least about 180 mW/cm$^2$. Additionally or alternately, the amount of waste heat generated by a fuel cell can be less than about 250 mW/cm$^2$, such as less than about 200 mW/cm$^2$, or less than about 180 mW/cm$^2$, or less than about 165 mW/cm$^2$, or less than about 150 mW/cm$^2$.

Although the amount of waste heat being generated can be relatively high, such waste heat may not necessarily represent operating a fuel cell with poor efficiency. Instead, the waste heat can be generated due to operating a fuel cell at an increased power density. Part of improving the power density of a fuel cell can include operating the fuel cell at a sufficiently high current density. In various aspects, the current density generated by the fuel cell can be at least about 150 mA/cm$^2$, such as at least about 160 mA/cm$^2$, or at least about 170 mA/cm$^2$, or at least about 180 mA/cm$^2$, or at least about 190 mA/cm$^2$, or at least about 200 mA/cm$^2$, or at least about 225 mA/cm$^2$, or at least about 250 mA/cm$^2$. Additionally or alternately, the current density generated by the fuel cell can be about 500 mA/cm$^2$ or less, such as 450 mA/cm$^2$, or less, or 400 mA/cm$^2$, or less or 350 mA/cm$^2$, or less or 300 mA/cm$^2$ or less.

In various aspects, to allow a fuel cell to be operated with increased power generation and increased generation of waste heat, an effective amount of an endothermic reaction (such as a reforming reaction) can be performed. Alternatively, other endothermic reactions unrelated to anode operations can be used to utilize the waste heat by interspersing "plates" or stages into the fuel cell array in thermal communication but not in fluid communication with either anodes or cathodes. The effective amount of the endothermic reaction can be performed in an associated reforming stage, an integrated reforming stage, an integrated stack element for performing an endothermic reaction, or a combination thereof. The effective amount of the endothermic reaction can correspond to an amount sufficient to reduce the temperature rise from the fuel cell inlet to the fuel cell outlet to about 100° C. or less, such as about 90° C. or less, or about 80° C. or less, or about 70° C. or less, or about 60° C. or less, or about 50° C. or less, or about 40° C. or less, or about 30° C. or less. Additionally or alternately, the effective amount of the endothermic reaction can correspond to an amount sufficient to cause a temperature decrease from the fuel cell inlet to the fuel cell outlet of about 100° C. or less, such as about 90° C. or less, or about 80° C. or less, or about 70° C. or less, or about 60° C. or less, or about 50° C. or less, or about 40° C. or less, or about 30° C. or less, or about 20° C. or less, or about 10° C. or less. A temperature decrease from the fuel cell inlet to the fuel cell outlet can occur when the effective amount of the endothermic reaction exceeds the waste heat generated. Additionally or alternately, this can correspond to having the endothermic reaction(s) (such as a combination of reforming and another endothermic reaction) consume at least about 40% of the waste heat generated by the fuel cell, such as consuming at least about 50% of the waste heat, or at least about 60% of the waste heat, or at least about 75% of the waste heat. Further additionally or alternately, the endothermic reaction(s) can consume about 95% of the waste heat or less, such as about 90% of the waste heat or less, or about 85% of the waste heat or less.

In various aspects, a fuel cell can be operated at a first operating condition. The first operating condition can include a sufficient specification of parameters to determine operation of the fuel cell, such as (but not limited to) a specification of the temperature at the anode inlet, a temperature at the cathode inlet, a pressure in the anode, a pressure in the cathode, a partial pressure of fuel in the anode inlet stream, a partial pressure of water in the anode inlet stream, a $CO_2$ partial pressure in the cathode inlet stream, an oxygen partial pressure in the cathode inlet stream, an equivalent hydrogen content in the anode inlet stream, a fuel utilization for the fuel cell, and/or other parameters.

The first operating condition can have a corresponding baseline operating condition. A baseline operating condition is defined herein as having the same operating condition values as a first operating condition, with the exception that the fuel utilization for a baseline operating condition is in the range from about 70% to about 80% and the anode inlet stream is composed of at least 80% by volume of methane (on a dry basis, i.e., excluding the water content). Thus, a baseline operating condition can provide a way to characterize the operational parameters for a given first operating condition if the parameters were used for conventional fuel cell operation.

In an aspect, a first operating condition can be selected that increases the electrical power of the fuel cell, where the corresponding baseline operating condition would result in a temperature increase between the anode inlet and anode outlet greater than about 75° C., such as greater than about 100° C. In such an aspect, the first operating condition can represent a modification of the baseline condition, preferably according to the methods described herein, that can reduce the heat increase between anode inlet and anode outlet to a more desirable level, such as a difference between anode inlet and anode outlet of about 100° C. or less, or about 80° C. or less, or about 60° C. or less, or about 50° C. or less, or about 40° C. or less. It is noted that, in some aspects, a corresponding conventional set of conditions for fuel cell operation may not be available. For example, a fuel cell may have an integrated, but not electrically associated, endothermic reaction stage where an effective amount of an endothermic reaction is performed to offset a temperature increase due to the exothermic nature of the fuel cell reaction. In such an example where the endothermic reaction stage is not electrically associated with the fuel cell, the differences between the first operating condition and the baseline operating condition may not result in a substantial change in the temperature difference between the anode inlet and anode outlet in the first operating condition and the baseline operating condition. In other words, even though the first operating condition can provide a temperature increase between anode inlet and anode outlet of less than about 50° C., the corresponding baseline condition may not result in a temperature increase between anode inlet and anode outlet of greater than 75° C.

The first operating condition can additionally or alternately have a corresponding maximum power operating condition. A corresponding maximum power operating condition can have the same anode inlet temperature, anode inlet flow rate, anode fuel partial pressure, anode water partial pressure, cathode inlet flow rate, cathode $CO_2$ partial pressure, and cathode $O_2$ partial pressure as the first operating condition. The maximum power operating condition can differ in that the fuel cell is operated at the maximum power density on a curve of power density versus current density. In some aspects, the power density of the maximum power operating condition can differ from the power density for the first operating condition by about 20% or less, such as about 15% or less, or about 10% or less, or about 5% or less. It is noted that the "fuel partial pressure" refers to a combined partial pressure of all fuel components in the anode inlet stream.

Syngas can be withdrawn from an anode exhaust by any convenient method. In some aspects, syngas can be withdrawn from the anode exhaust by performing separations on the anode exhaust to remove at least a portion of the components in the anode exhaust different from $H_2$ and CO. For example, an anode exhaust can first be passed through an optional water-gas shift stage to adjust the relative amounts of $H_2$ and CO. One or more separation stages can then be used to remove $H_2O$ and/or $CO_2$ from the anode exhaust. The remaining portion of the anode exhaust can then correspond to the syngas stream, which can then be withdrawn for use in any convenient manner. Additionally or alternately, the withdrawn syngas stream can be passed through one or more water-gas shift stages and/or passed through one or more separation stages.

The ratio of $H_2$ to CO at the exit from a fuel cell anode is usually determined by the water gas shift equilibrium at the exit temperature for the anode. After exiting the anode, the ratio of $H_2$ to CO can be modified to generate a desired syngas stream, such as by separating out $CO_2$, exposing the anode exhaust and/or the withdrawn syngas stream to additional water gas shift stages, and/or by other methods. In various aspects, the anode exhaust can have a ratio of $H_2$ to CO of about 1.5:1 to about 10:1, such as at least about 3.0:1, or at least about 4.0:1, or at least about 5.0:1, and/or about 8.0:1 or less or about 6.0:1 or less. A syngas stream can be withdrawn from the anode exhaust. In various aspects, a syngas stream withdrawn from an anode exhaust can have a ratio of moles of $H_2$ to moles of CO of at least about 0.9:1, such as at least about 1.0:1, or at least about 1.2:1, or at least about 1.5:1, or at least about 1.7:1, or at least about 1.8:1, or at least about 1.9:1. Additionally or alternately, the molar ratio of $H_2$ to CO in a syngas withdrawn from an anode exhaust can be about 3.0:1 or less, such as about 2.7:1 or less, or about 2.5:1 or less, or about 2.3:1 or less, or about 2.2:1 or less, or about 2.1:1 or less. It is noted that higher ratios of $H_2$ to CO in a withdrawn syngas stream can tend to reduce the amount of CO relative to the amount of $CO_2$ in a cathode exhaust. However, many types of syngas applications benefit from syngas with a molar ratio of $H_2$ to CO of at least about 1.5:1 to about 2.5:1 or less, so forming a syngas stream with a molar ratio of $H_2$ to CO content of, for example, about 1.7:1 to about 2.3:1 may be desirable for some applications.

It is noted that an additional or alternative way of modifying the molar ratio of $H_2$ to CO in the withdrawn syngas can be to separate an $H_2$ stream from the anode exhaust and/or the syngas, such as by performing a membrane separation. Such a separation to form a separate $H_2$ output stream can be performed at any convenient location, such as prior to and/or after passing the anode exhaust through a water-gas shift reaction stage, and/or prior to and/or after passing the anode exhaust through one or more separation stages for removing components in the anode exhaust different from $H_2$ and CO. Optionally, a water-gas shift stage can be used both before and after separation of an $H_2$ stream from the anode exhaust. In an additional or alternative embodiment, $H_2$ can optionally be separated from the anode exhaust and/or from the withdrawn syngas stream. In some aspects, a separated $H_2$ stream can correspond to a high purity $H_2$ stream, such as an $H_2$ stream containing at least about 90 vol % of $H_2$, such as at least about 95 vol % of $H_2$ or at least about 99 vol % of $H_2$.

As an addition, complement, and/or alternative to the fuel cell operating strategies described herein, a molten carbonate fuel cell (such as a fuel cell assembly) can be operated with an excess of reformable fuel relative to the amount of hydrogen reacted in the anode of the fuel cell. Instead of selecting the operating conditions of a fuel cell to improve or maximize the electrical efficiency of the fuel cell, an excess of reformable fuel can be passed into the anode of the fuel cell to increase the chemical energy output of the fuel cell. Optionally but preferably, this can lead to an increase in the total efficiency of the fuel cell based on the combined electrical efficiency and chemical efficiency of the fuel cell.

In some aspects, the reformable hydrogen content of reformable fuel in the input stream delivered to the anode and/or to a reforming stage associated with the anode can be at least about 50% greater than the amount of hydrogen oxidized in the anode, such as at least about 75% greater or at least about 100% greater. In various aspects, a ratio of the reformable hydrogen content of the reformable fuel in the fuel stream relative to an amount of hydrogen reacted in the anode can be at least about 1.5:1, or at least about 2.0:1, or at least about 2.5:1, or at least about 3.0:1. Additionally or alternately, the ratio of reformable hydrogen content of the reformable fuel in the fuel stream relative to the amount of hydrogen reacted in the anode can be about 20:1 or less, such as about 15:1 or less or about 10:1 or less. In one aspect, it is contemplated that less than 100% of the reformable hydrogen content in the anode inlet stream can be converted to hydrogen. For example, at least about 80% of the reformable hydrogen content in an anode inlet stream can be converted to hydrogen in the anode and/or in an associated reforming stage, such as at least about 85%, or at least about 90%.

As an addition, complement, and/or alternative to the fuel cell operating strategies described herein, a molten carbonate fuel cell can be operated so that the amount of reforming can be selected relative to the amount of oxidation in order to achieve a desired thermal ratio for the fuel cell. As used herein, the "thermal ratio" is defined as the heat produced by exothermic reactions in a fuel cell assembly divided by the endothermic heat demand of reforming reactions occurring within the fuel cell assembly. Expressed mathematically, the thermal ratio (TH)=$Q_{EX}/Q_{EN}$, where $Q_{EX}$ is the sum of heat produced by exothermic reactions and $Q_{EN}$ is the sum of heat consumed by the endothermic reactions occurring within the fuel cell. Note that the heat produced by the exothermic reactions corresponds to any heat due to reforming reactions, water gas shift reactions, and the electrochemical reactions in the cell. The heat generated by the electrochemical reactions can be calculated based on the ideal electrochemical potential of the fuel cell reaction across the electrolyte minus the actual output voltage of the fuel cell. For example, the ideal electrochemical potential of the reaction in a MCFC is believed to be about 1.04V based on the net reaction that occurs in the cell. During operation of the MCFC, the cell will typically have an output voltage less than 1.04 V due to various losses. For example, a common output/operating voltage can be about 0.7 V. The heat generated is equal to the electrochemical potential of the cell (i.e. ~1.04V) minus the operating voltage. For example, the heat produced by the electrochemical reactions in the cell is ~0.34 V when the output voltage of ~0.7V. Thus, in this scenario, the electrochemical reactions would produce ~0.7 V of electricity and ~0.34 V of heat energy. In such an example, the ~0.7 V of electrical energy is not included as part of $Q_{EX}$. In other words, heat energy is not electrical energy.

In various aspects, a thermal ratio can be determined for any convenient fuel cell structure, such as a fuel cell stack, an individual fuel cell within a fuel cell stack, a fuel cell stack with an integrated reforming stage, a fuel cell stack with an integrated endothermic reaction stage, or a combination thereof. The thermal ratio may also be calculated for different units within a fuel cell stack, such as an assembly of fuel cells or fuel cell stacks. For example, the thermal ratio may be calculated for a single anode within a single fuel cell, an anode section within a fuel cell stack, or an anode section within a fuel cell stack along with integrated reforming stages and/or integrated endothermic reaction stage elements in sufficiently close proximity to the anode section to be integrated from a heat integration standpoint.

As used herein, "an anode section" comprises anodes within a fuel cell stack that share a common inlet or outlet manifold.

In various aspects of the invention, the operation of the fuel cells can be characterized based on a thermal ratio. Where fuel cells are operated to have a desired thermal ratio, a molten carbonate fuel cell can be operated to have a thermal ratio of about 1.5 or less, for example about 1.3 or less, or about 1.15 or less, or about 1.0 or less, or about 0.95 or less, or about 0.90 or less, or about 0.85 or less, or about 0.80 or less, or about 0.75 or less. Additionally or alternately, the thermal ratio can be at least about 0.25, or at least about 0.35, or at least about 0.45, or at least about 0.50. Additionally or alternately, in some aspects the fuel cell can be operated to have a temperature rise between anode input and anode output of about 40° C. or less, such as about 20° C. or less, or about 10° C. or less. Further additionally or alternately, the fuel cell can be operated to have an anode outlet temperature that is from about 10° C. lower to about 10° C. higher than the temperature of the anode inlet. Still further additionally or alternately, the fuel cell can be operated to have an anode inlet temperature that is greater than the anode outlet temperature, such as at least about 5° C. greater, or at least about 10° C. greater, or at least about 20° C. greater, or at least about 25° C. greater. Yet still further additionally or alternately, the fuel cell can be operated to have an anode inlet temperature that is greater than the anode outlet temperature by about 100° C. or less, such as by about 80° C. or less, or about 60° C. or less, or about 50° C. or less, or about 40° C. or less, or about 30° C. or less, or about 20° C. or less.

As an addition, complement, and/or alternative to the fuel cell operating strategies described herein, a molten carbonate fuel cell (such as a fuel cell assembly) can be operated with increased production of syngas (or hydrogen) while also reducing or minimizing the amount of $CO_2$ exiting the fuel cell in the cathode exhaust stream. Syngas can be a valuable input for a variety of processes. In addition to having fuel value, syngas can be used as a raw material for forming other higher value products, such as by using syngas as an input for Fischer-Tropsch synthesis and/or methanol synthesis processes. One option for making syngas can be to reform a hydrocarbon or hydrocarbon-like fuel, such as methane or natural gas. For many types of industrial processes, a syngas having a ratio of $H_2$ to CO of close to 2:1 (or even lower) can often be desirable. A water gas shift reaction can be used to reduce the $H_2$ to CO ratio in a syngas if additional $CO_2$ is available, such as is produced in the anodes.

One way of characterizing the overall benefit provided by integrating syngas generation with use of molten carbonate fuel cells can be based on a ratio of the net amount of syngas that exits the fuel cells in the anode exhaust relative to the amount of $CO_2$ that exits the fuel cells in the cathode exhaust. This characterization measures the effectiveness of producing power with low emissions and high efficiency (both electrical and chemical). In this description, the net amount of syngas in an anode exhaust is defined as the combined number of moles of $H_2$ and number of moles of CO present in the anode exhaust, offset by the amount of $H_2$ and CO present in the anode inlet. Because the ratio is based on the net amount of syngas in the anode exhaust, simply passing excess $H_2$ into the anode does not change the value of the ratio. However, $H_2$ and/or CO generated due to reforming in the anode and/or in an internal reforming stage associated with the anode can lead to higher values of the ratio. Hydrogen oxidized in the anode can lower the ratio. It is noted that the water gas shift reaction can exchange $H_2$ for CO, so the combined moles of $H_2$ and CO represents the total potential syngas in the anode exhaust, regardless of the eventual desired ratio of $H_2$ to CO in a syngas. The syngas content of the anode exhaust ($H_2$+CO) can then be compared with the $CO_2$ content of the cathode exhaust. This can provide a type of efficiency value that can also account for the amount of carbon capture. This can equivalently be expressed as an equation as Ratio of net syngas in anode exhaust to cathode $CO_2$=net moles of $(H_2+CO)_{ANODE}$/moles of $(CO_2)_{CATHODE}$ In various aspects, the ratio of net moles of syngas in the anode exhaust to the moles of $CO_2$ in the cathode exhaust can be at least about 2.0, such as at least about 3.0, or at least about 4.0, or at least about 5.0. In some aspects, the ratio of net syngas in the anode exhaust to the amount of $CO_2$ in the cathode exhaust can be still higher, such as at least about 10.0, or at least about 15.0, or at least about 20.0. Ratio values of about 40.0 or less, such as about 30.0 or less, or about 20.0 or less, can additionally or alternatively be achieved. In aspects where the amount of $CO_2$ at the cathode inlet is about 6.0 volume % or less, such as about 5.0 volume % or less, ratio values of at least about 1.5 may be sufficient/realistic. Such molar ratio values of net syngas in the anode exhaust to the amount of $CO_2$ in the cathode exhaust can be greater than the values for conventionally operated fuel cells.

As an addition, complement, and/or alternative to the fuel cell operating strategies described herein, a molten carbonate fuel cell (such as a fuel cell assembly) can be operated at a reduced fuel utilization value, such as a fuel utilization of about 50% or less, while also having a high $CO_2$ utilization value, such as at least about 60%. In this type of configuration, the molten carbonate fuel cell can be effective for carbon capture, as the $CO_2$ utilization can advantageously be sufficiently high. Rather than attempting to maximize electrical efficiency, in this type of configuration the total efficiency of the fuel cell can be improved or increased based on the combined electrical and chemical efficiency. The chemical efficiency can be based on withdrawal of a hydrogen and/or syngas stream from the anode exhaust as an output for use in other processes. Even though the electrical efficiency may be reduced relative to some conventional configurations, making use of the chemical energy output in the anode exhaust can allow for a desirable total efficiency for the fuel cell.

In various aspects, the fuel utilization in the fuel cell anode can be about 50% or less, such as about 40% or less, or about 30% or less, or about 25% or less, or about 20% or less. In various aspects, in order to generate at least some electric power, the fuel utilization in the fuel cell can be at least about 5%, such as at least about 10%, or at least about 15%, or at least about 20%, or at least about 25%, or at least about 30%. Additionally or alternatively, the $CO_2$ utilization can be at least about 60%, such as at least about 65%, or at least about 70%, or at least about 75%.

As an addition, complement, and/or alternative to the fuel cell operating strategies described herein, a molten carbonate fuel cell (such as a fuel cell assembly) can also be operated at conditions that can improve or optimize the combined electrical efficiency and chemical efficiency of the fuel cell. Instead of selecting conventional conditions for maximizing the electrical efficiency of a fuel cell, the operating conditions can allow for output of excess synthesis gas and/or hydrogen in the anode exhaust of the fuel cell. The synthesis gas and/or hydrogen can then be used in a variety of applications, including chemical synthesis processes and collection of hydrogen for use as a "clean" fuel. In aspects of the invention, electrical efficiency can be reduced to achieve a high overall efficiency, which includes a chemical efficiency based on the chemical energy value of syngas and/or hydrogen produced relative to the energy value of the fuel input for the fuel cell.

In some aspects, the operation of the fuel cells can be characterized based on electrical efficiency. Where fuel cells are operated to have a low electrical efficiency (EE), a molten carbonate fuel cell can be operated to have an electrical efficiency of about 40% or less, for example, about 35% EE or less, about 30% EE or less, about 25% EE or less, or about 20% EE or less, about 15% EE or less, or about 10% EE or less. Additionally or alternatively, the EE can be at least about 5%, or at least about 10%, or at least about 15%, or at least about 20%. Further additionally or alternatively, the operation of the fuel cells can be characterized based on total fuel cell efficiency (TFCE), such as a combined electrical efficiency and chemical efficiency of the fuel cell(s). Where fuel cells are operated to have a high total fuel cell efficiency, a molten carbonate fuel cell can be operated to have a TFCE (and/or combined electrical efficiency and chemical efficiency) of about 55% or more, for example, about 60% or more, or about 65% or more, or about 70% or more, or about 75% or more, or about 80% or more, or about 85% or more. It is noted that for a total fuel cell efficiency and/or combined electrical efficiency and chemical efficiency, any additional electricity generated from use of excess heat generated by the fuel cell can be excluded from the efficiency calculation.

In various aspects of the invention, the operation of the fuel cells can be characterized based on a desired electrical efficiency of about 40% or less and a desired total fuel cell efficiency of about 55% or more. Where fuel cells are operated to have a desired electrical efficiency and a desired total fuel cell efficiency, a molten carbonate fuel cell can be operated to have an electrical efficiency of about 40% or less with a TFCE of about 55% or more, for example, about 35% EE or less with about a TFCE of 60% or more, about 30% EE or less with about a TFCE of about 65% or more, about 25% EE or less with about a 70% TFCE or more, or about 20% EE or less with about a TFCE of 75% or more, about 15% EE or less with about a TFCE of 80% or more, or about 10% EE or less with about a TFCE of about 85% or more.

Definitions

Syngas: In this description, syngas is defined as mixture of $H_2$ and CO in any ratio. Optionally, $H_2O$ and/or $CO_2$ may be present in the syngas. Optionally, inert compounds (such as nitrogen) and residual reformable fuel compounds may be present in the syngas. If components other than $H_2$ and CO are present in the syngas, the combined volume percentage of $H_2$ and CO in the syngas can be at least 25 vol % relative to the total volume of the syngas, such as at least 40 vol %, or at least 50 vol %, or at least 60 vol %. Additionally or alternately, the combined volume percentage of $H_2$ and CO in the syngas can be 100 vol % or less, such as 95 vol % or less or 90 vol % or less.

Reformable fuel: A reformable fuel is defined as a fuel that contains carbon-hydrogen bonds that can be reformed to generate $H_2$. Hydrocarbons are examples of reformable fuels, as are other hydrocarbonaceous compounds such as alcohols. Although CO and $H_2O$ can participate in a water gas shift reaction to form hydrogen, CO is not considered a reformable fuel under this definition.

Reformable hydrogen content: The reformable hydrogen content of a fuel is defined as the number of $H_2$ molecules that can be derived from a fuel by reforming the fuel and then driving the water gas shift reaction to completion to maximize $H_2$ production. It is noted that $H_2$ by definition has a reformable hydrogen content of 1, although $H_2$ itself is not defined as a reformable fuel herein. Similarly, CO has a reformable hydrogen content of 1. Although CO is not strictly reformable, driving the water gas shift reaction to completion will result in exchange of a CO for an $H_2$. As examples of reformable hydrogen content for reformable fuels, the reformable hydrogen content of methane is $4H_2$ molecules while the reformable hydrogen content of ethane is $7H_2$ molecules. More generally, if a fuel has the composition CxHyOz, then the reformable hydrogen content of the fuel at 100% reforming and water-gas shift is $n(H_2$ max reforming$)=2x+y/2-z$. Based on this definition, fuel utilization within a cell can then be expressed as $n(H_2$ ox$)/n(H_2$ max reforming). Of course, the reformable hydrogen content of a mixture of components can be determined based on the reformable hydrogen content of the individual components. The reformable hydrogen content of compounds that contain other heteroatoms, such as oxygen, sulfur or nitrogen, can also be calculated in a similar manner.

Oxidation Reaction: In this discussion, the oxidation reaction within the anode of a fuel cell is defined as the reaction corresponding to oxidation of $H_2$ by reaction with $CO_3^{2-}$ to form $H_2O$ and $CO_2$. It is noted that the reforming reaction within the anode, where a compound containing a carbon-hydrogen bond is converted into $H_2$ and CO or $CO_2$, is excluded from this definition of the oxidation reaction in the anode. The water-gas shift reaction is similarly outside of this definition of the oxidation reaction. It is further noted that references to a combustion reaction are defined as references to reactions where $H_2$ or a compound containing carbon-hydrogen bond(s) are reacted with $O_2$ to form $H_2O$ and carbon oxides in a non-electrochemical burner, such as the combustion zone of a combustion-powered generator.

Aspects of the invention can adjust anode fuel parameters to achieve a desired operating range for the fuel cell. Anode fuel parameters can be characterized directly, and/or in relation to other fuel cell processes in the form of one or more ratios. For example, the anode fuel parameters can be controlled to achieve one or more ratios including a fuel utilization, a fuel cell heating value utilization, a fuel surplus ratio, a reformable fuel surplus ratio, a reformable hydrogen content fuel ratio, and combinations thereof.

Fuel utilization: Fuel utilization is an option for characterizing operation of the anode based on the amount of oxidized fuel relative to the reformable hydrogen content of an input stream can be used to define a fuel utilization for a fuel cell. In this discussion, "fuel utilization" is defined as the ratio of the amount of hydrogen oxidized in the anode for production of electricity (as described above) versus the reformable hydrogen content of the anode input (including any associated reforming stages). Reformable hydrogen content has been defined above as the number of $H_2$ molecules that can be derived from a fuel by reforming the fuel and then driving the water gas shift reaction to completion to maximize $H_2$ production. For example, each methane introduced into an anode and exposed to steam reforming conditions results in generation of the equivalent of $4H_2$ molecules at max production. (Depending on the reforming and/or anode conditions, the reforming product can correspond to a non-water gas shifted product, where one or more of the $H_2$ molecules is present instead in the form of a CO molecule.) Thus, methane is defined as having a reformable hydrogen content of $4H_2$ molecules. As another example, under this definition ethane has a reformable hydrogen content of $7H_2$ molecules.

The utilization of fuel in the anode can also be characterized by defining a heating value utilization based on a ratio of the Lower Heating Value of hydrogen oxidized in the anode due to the fuel cell anode reaction relative to the Lower Heating Value of all fuel delivered to the anode and/or a reforming stage associated with the anode. The "fuel cell heating value utilization" as used herein can be computed using the flow rates and Lower Heating Value (LHV) of the fuel components entering and leaving the fuel cell anode. As such, fuel cell heating value utilization can be computed as (LHV(anode_in)−LHV(anode_out))/LHV(anode_in), where LHV(anode_in) and LHV(anode_out) refer to the LHV of the fuel components (such as $H_2$, $CH_4$, and/or CO) in the anode inlet and outlet streams or flows, respectively. In this definition, the LHV of a stream or flow may be computed as a sum of values for each fuel component in the input and/or output stream. The contribution of each fuel component to the sum can correspond to the fuel component's flow rate (e.g., mol/hr) multiplied by the fuel component's LHV (e.g., joules/mol).

Lower Heating Value: The lower heating value is defined as the enthalpy of combustion of a fuel component to vapor phase, fully oxidized products (i.e., vapor phase $CO_2$ and $H_2O$ product). For example, any $CO_2$ present in an anode input stream does not contribute to the fuel content of the anode input, since $CO_2$ is already fully oxidized. For this definition, the amount of oxidation occurring in the anode due to the anode fuel cell reaction is defined as oxidation of $H_2$ in the anode as part of the electrochemical reaction in the anode, as defined above.

It is noted that, for the special case where the only fuel in the anode input flow is $H_2$, the only reaction involving a fuel component that can take place in the anode represents the conversion of $H_2$ into $H_2O$. In this special case, the fuel utilization simplifies to ($H_2$-rate-in minus $H_2$-rate-out)/$H_2$-rate-in. In such a case, $H_2$ would be the only fuel component, and so the $H_2$ LHV would cancel out of the equation. In the more general case, the anode feed may contain, for example, $CH_4$, $H_2$, and CO in various amounts. Because these species can typically be present in different amounts in the anode outlet, the summation as described above can be needed to determine the fuel utilization.

Alternatively or in addition to fuel utilization, the utilization for other reactants in the fuel cell can be characterized. For example, the operation of a fuel cell can additionally or alternately be characterized with regard to "$CO_2$ utilization" and/or "oxidant" utilization. The values for $CO_2$ utilization and/or oxidant utilization can be specified in a similar manner.

Fuel surplus ratio: Still another way to characterize the reactions in a molten carbonate fuel cell is by defining a utilization based on a ratio of the Lower Heating Value of all fuel delivered to the anode and/or a reforming stage associated with the anode relative to the Lower Heating Value of hydrogen oxidized in the anode due to the fuel cell anode reaction. This quantity will be referred to as a fuel surplus ratio. As such the fuel surplus ratio can be computed as (LHV (anode_in)/(LHV(anode_in)−LHV(anode_out)) where LHV(anode_in) and LHV(anode_out) refer to the LHV of the fuel components (such as $H_2$, $CH_4$, and/or CO) in the anode inlet and outlet streams or flows, respectively. In various aspects of the invention, a molten carbonate fuel cell can be operated to have a fuel surplus ratio of at least about 1.0, such as at least about 1.5, or at least about 2.0, or at least about 2.5, or at least about 3.0, or at least about 4.0. Additionally or alternately, the fuel surplus ratio can be about 25.0 or less.

It is noted that not all of the reformable fuel in the input stream for the anode may be reformed. Preferably, at least about 90% of the reformable fuel in the input stream to the anode (and/or into an associated reforming stage) can be reformed prior to exiting the anode, such as at least about 95% or at least about 98%. In some alternative aspects, the amount of reformable fuel that is reformed can be from about 75% to about 90%, such as at least about 80%.

The above definition for fuel surplus ratio provides a method for characterizing the amount of reforming occurring within the anode and/or reforming stage(s) associated with a fuel cell relative to the amount of fuel consumed in the fuel cell anode for generation of electric power.

Optionally, the fuel surplus ratio can be modified to account for situations where fuel is recycled from the anode output to the anode input. When fuel (such as $H_2$, CO, and/or unreformed or partially reformed hydrocarbons) is recycled from anode output to anode input, such recycled fuel components do not represent a surplus amount of reformable or reformed fuel that can be used for other purposes. Instead, such recycled fuel components merely indicate a desire to reduce fuel utilization in a fuel cell.

Reformable fuel surplus ratio: Calculating a reformable fuel surplus ratio is one option to account for such recycled fuel components, to narrow the definition of surplus fuel, so that only the LHV of reformable fuels is included in the input stream to the anode. As used herein the "reformable fuel surplus ratio" is defined as the Lower Heating Value of reformable fuel delivered to the anode and/or a reforming stage associated with the anode relative to the Lower Heating Value of hydrogen oxidized in the anode due to the fuel cell anode reaction. Under the definition for reformable fuel surplus ratio, the LHV of any $H_2$ or CO in the anode input is excluded. Such an LHV of reformable fuel can still be measured by characterizing the actual composition entering a fuel cell anode, so no distinction between recycled components and fresh components needs to be made. Although some non-reformed or partially reformed fuel may also be recycled, in most aspects the majority of the fuel recycled to the anode can correspond to reformed products such as $H_2$ or CO. Expressed mathematically, the reformable fuel surplus ratio ($R_{RFS}$)=$LHV_{RF}/LHV_{OH}$, where $LHV_{RF}$ is the Lower Heating Value (LHV) of the reformable fuel and $LHV_{OH}$ is the Lower Heating Value (LHV) of the hydrogen oxidized in the anode. The LHV of the hydrogen oxidized in the anode may be calculated by subtracting the LHV of the anode outlet stream from the LHV of the anode inlet stream (e.g., LHV(anode_in)−LHV(anode_out)). In various aspects of the invention, a molten carbonate fuel cell can be operated to have a reformable fuel surplus ratio of at least about 0.25, such as at least about 0.5, or at least about 1.0, or at least about 1.5, or at least about 2.0, or at least about 2.5, or at least about 3.0, or at least about 4.0. Additionally or alternately, the reformable fuel surplus ratio can be about 25.0 or less. It is noted that this narrower definition based on the amount of reformable fuel delivered to the anode relative to the amount of oxidation in the anode can distinguish between two types of fuel cell operation methods that have low fuel utilization. Some fuel cells achieve low fuel utilization by recycling a substantial portion of the anode output back to the anode input. This recycle can allow any hydrogen in the anode input to be used again as an input to the anode. This can reduce the amount of reforming, as even though the fuel utilization is low for a single pass through the fuel cell, at least a portion of the unused fuel is recycled for use in a later pass. Thus, fuel cells with a wide variety of fuel utilization values may have the same ratio of reformable fuel delivered to the anode reforming stage(s) versus hydrogen oxidized in the anode reaction. In order to change the ratio of reformable fuel delivered to the anode reforming stages relative to the amount of oxidation in the anode, either an anode feed with a native content of non-reformable fuel needs to be identified, or unused fuel in the anode output needs to be withdrawn for other uses, or both.

Reformable hydrogen surplus ratio: Still another option for characterizing the operation of a fuel cell is based on a "reformable hydrogen surplus ratio." The reformable fuel surplus ratio defined above is defined based on the lower heating value of reformable fuel components. The reformable hydrogen surplus ratio is defined as the reformable hydrogen content of reformable fuel delivered to the anode and/or a reforming stage associated with the anode relative to the hydrogen reacted in the anode due to the fuel cell anode reaction. As such, the "reformable hydrogen surplus ratio" can be computed as (RFC(reformable_anode_in)/ (RFC(reformable_anode_in)-RFC(anode_out)), where RFC (reformable_anode_in) refers to the reformable hydrogen content of reformable fuels in the anode inlet streams or flows, while RFC (anode_out) refers to the reformable hydrogen content of the fuel components (such as $H_2$, $CH_4$, and/or CO) in the anode inlet and outlet streams or flows. The RFC can be expressed in moles/s, moles/hr, or similar. An example of a method for operating a fuel cell with a large ratio of reformable fuel delivered to the anode reforming stage(s) versus amount of oxidation in the anode can be a method where excess reforming is performed in order to balance the generation and consumption of heat in the fuel cell. Reforming a reformable fuel to form $H_2$ and CO is an endothermic process. This endothermic reaction can be countered by the generation of electrical current in the fuel cell, which can also produce excess heat corresponding (roughly) to the difference between the amount of heat generated by the anode oxidation reaction and the carbonate formation reaction and the energy that exits the fuel cell in the form of electric current. The excess heat per mole of hydrogen involved in the anode oxidation reaction/carbonate formation reaction can be greater than the heat absorbed to generate a mole of hydrogen by reforming. As a result, a fuel cell operated under conventional conditions can exhibit a temperature increase from inlet to outlet. Instead of this type of conventional operation, the amount of fuel reformed in the reforming stages associated with the anode can be increased. For example, additional fuel can be reformed so that the heat generated by the exothermic fuel cell reactions can be (roughly) balanced by the heat consumed in reforming, or even the heat consumed by reforming can be beyond the excess heat generated by the fuel oxidation, resulting in a temperature drop across the fuel cell. This can result in a substantial excess of hydrogen relative to the amount needed for electrical power generation. As one example, a feed to the anode inlet of a fuel cell or an associated reforming stage can be substantially composed of reformable fuel, such as a substantially pure methane feed. During conventional operation for electric power generation using such a fuel, a molten carbonate fuel cell can be operated with a fuel utilization of about 75%. This means that about 75% (or ¾) of the fuel content delivered to the anode is used to form hydrogen that is then reacted in the anode with carbonate ions to form $H_2O$ and $CO_2$. In conventional operation, the remaining about 25% of the fuel content can be reformed to $H_2$ within the fuel cell (or can pass through the fuel cell unreacted for any CO or $H_2$ in the fuel), and then combusted outside of the fuel cell to form $H_2O$ and $CO_2$ to provide heat for the cathode inlet to the fuel cell. The reformable hydrogen surplus ratio in this situation can be 4/(4−1)=4/3.

Electrical efficiency: As used herein, the term "electrical efficiency" ("EE") is defined as the electrochemical power produced by the fuel cell divided by the rate of Lower Heating Value ("LHV") of fuel input to the fuel cell. The fuel inputs to the fuel cell includes both fuel delivered to the anode as well as any fuel used to maintain the temperature of the fuel cell, such as fuel delivered to a burner associated with a fuel cell. In this description, the power produced by the fuel may be described in terms of LHV(el) fuel rate.

Electrochemical power: As used herein, the term "electrochemical power" or LHV(el) is the power generated by the circuit connecting the cathode to the anode in the fuel cell and the transfer of carbonate ions across the fuel cell's electrolyte. Electrochemical power excludes power produced or consumed by equipment upstream or downstream from the fuel cell. For example, electricity produced from heat in a fuel cell exhaust stream is not considered part of the electrochemical power. Similarly, power generated by a gas turbine or other equipment upstream of the fuel cell is not part of the electrochemical power generated. The "electrochemical power" does not take electrical power consumed during operation of the fuel cell into account, or any loss incurred by conversion of the direct current to alternating current. In other words, electrical power used to supply the fuel cell operation or otherwise operate the fuel cell is not subtracted from the direct current power produced by the fuel cell. As used herein, the power density is the current density multiplied by voltage. As used herein, the total fuel cell power is the power density multiplied by the fuel cell area.

Fuel inputs: As used herein, the term "anode fuel input," designated as LHV(anode_in), is the amount of fuel within the anode inlet stream. The term "fuel input", designated as LHV(in), is the total amount of fuel delivered to the fuel cell, including both the amount of fuel within the anode inlet stream and the amount of fuel used to maintain the temperature of the fuel cell. The fuel may include both reformable and nonreformable fuels, based on the definition of a reformable fuel provided herein. Fuel input is not the same as fuel utilization.

Total fuel cell efficiency: As used herein, the term "total fuel cell efficiency" ("TFCE") is defined as: the electrochemical power generated by the fuel cell, plus the rate of LHV of syngas produced by the fuel cell, divided by the rate of LHV of fuel input to the anode. In other words, TFCE= (LHV(el)+LHV(sg net))/LHV(anode_in), where LHV(anode_in) refers to rate at which the LHV of the fuel components (such as $H_2$, $CH_4$, and/or CO) delivered to the anode and LHV(sg net) refers to a rate at which syngas ($H_2$, CO) is produced in the anode, which is the difference between syngas input to the anode and syngas output from the anode. LHV(el) describes the electrochemical power generation of the fuel cell. The total fuel cell efficiency excludes heat generated by the fuel cell that is put to beneficial use outside of the fuel cell. In operation, heat generated by the fuel cell may be put to beneficial use by downstream equipment. For example, the heat may be used to generate additional electricity or to heat water. These uses, when they occur apart from the fuel cell, are not part of the total fuel cell efficiency, as the term is used in this application. The total fuel cell efficiency is for the fuel cell operation only, and does not include power production, or consumption, upstream, or downstream, of the fuel cell.

Chemical efficiency: As used herein, the term "chemical efficiency", is defined as the lower heating value of $H_2$ and CO in the anode exhaust of the fuel cell, or LHV(sg out), divided by the fuel input, or LHV(in).

Neither the electrical efficiency nor the total system efficiency takes the efficiency of upstream or downstream processes into consideration. For example, it may be advantageous to use turbine exhaust as a source of $CO_2$ for the fuel cell cathode. In this arrangement, the efficiency of the turbine is not considered as part of the electrical efficiency or the total fuel cell efficiency calculation. Similarly, outputs from the fuel cell may be recycled as inputs to the fuel cell. A recycle loop is not considered when calculating electrical efficiency or the total fuel cell efficiency in single pass mode.

Syngas produced: As used herein, the term "syngas produced" is the difference between syngas input to the anode and syngas output from the anode. Syngas may be used as an input, or fuel, for the anode, at least in part. For example, a system may include an anode recycle loop that returns syngas from the anode exhaust to the anode inlet where it is supplemented with natural gas or other suitable fuel. Syngas produced LHV (sg net)=(LHV(sg out)−LHV(sg in)), where LHV(sg in) and LHV(sg out) refer to the LHV of the syngas in the anode inlet and syngas in the anode outlet streams or flows, respectively. It is noted that at least a portion of the syngas produced by the reforming reactions within an anode can typically be utilized in the anode to produce electricity. The hydrogen utilized to produce electricity is not included in the definition of "syngas produced" because it does not exit the anode. As used herein, the term "syngas ratio" is the LHV of the net syngas produced divided by the LHV of the fuel input to the anode or LHV (sg net)/LHV(anode in). Molar flow rates of syngas and fuel can be used instead of LHV to express a molar-based syngas ratio and a molar-based syngas produced.

Steam to carbon ratio (S/C): As used herein, the steam to carbon ratio (S/C) is the molar ratio of steam in a flow to reformable carbon in the flow. Carbon in the form of CO and $CO_2$ are not included as reformable carbon in this definition. The steam to carbon ratio can be measured and/or controlled at different points in the system. For example, the composition of an anode inlet stream can be manipulated to achieve a S/C that is suitable for reforming in the anode. The S/C can be given as the molar flow rate of $H_2O$ divided by the product of the molar flow rate of fuel multiplied by the number of carbon atoms in the fuel, e.g. one for methane. Thus, S/C=$f_{H2O}$/($f_{CH4}$×#C), where $f_{H2O}$ is the molar flow rate of water, where $f_{CH4}$ is the molar flow rate of methane (or other fuel) and #C is the number of carbons in the fuel.

EGR ratio: Aspects of the invention can use a turbine in partnership with a fuel cell. The combined fuel cell and turbine system may include exhaust gas recycle ("EGR"). In an EGR system, at least a portion of the exhaust gas generated by the turbine can be sent to a heat recovery generator. Another portion of the exhaust gas can be sent to the fuel cell. The EGR ratio describes the amount of exhaust gas routed to the fuel cell versus the total exhaust gas routed to either the fuel cell or heat recovery generator. As used herein, the "EGR ratio" is the flow rate for the fuel cell bound portion of the exhaust gas divided by the combined flow rate for the fuel cell bound portion and the recovery bound portion, which is sent to the heat recovery generator.

In various aspects of the invention, a molten carbonate fuel cell (MCFC) can be used to facilitate separation of $CO_2$ from a $CO_2$-containing stream while also generating additional electrical power. The $CO_2$ separation can be further enhanced by taking advantage of synergies with the combustion-based power generator that can provide at least a portion of the input feed to the cathode portion of the fuel cell.

Fuel Cell and Fuel Cell Components: In this discussion, a fuel cell can correspond to a single cell, with an anode and a cathode separated by an electrolyte. The anode and cathode can receive input gas flows to facilitate the respective anode and cathode reactions for transporting charge across the electrolyte and generating electricity. A fuel cell stack can represent a plurality of cells in an integrated unit. Although a fuel cell stack can include multiple fuel cells, the fuel cells can typically be connected in parallel and can function (approximately) as if they collectively represented a single fuel cell of a larger size. When an input flow is delivered to the anode or cathode of a fuel cell stack, the fuel stack can include flow channels for dividing the input flow between each of the cells in the stack and flow channels for combining the output flows from the individual cells. In this discussion, a fuel cell array can be used to refer to a plurality of fuel cells (such as a plurality of fuel cell stacks) that are arranged in series, in parallel, or in any other convenient manner (e.g., in a combination of series and parallel). A fuel cell array can include one or more stages of fuel cells and/or fuel cell stacks, where the anode/cathode output from a first stage may serve as the anode/cathode input for a second stage. It is noted that the anodes in a fuel cell array do not have to be connected in the same way as the cathodes in the array. For convenience, the input to the first anode stage of a fuel cell array may be referred to as the anode input for the array, and the input to the first cathode stage of the fuel cell array may be referred to as the cathode input to the array. Similarly, the output from the final anode/cathode stage may be referred to as the anode/cathode output from the array.

It should be understood that reference to use of a fuel cell herein typically denotes a "fuel cell stack" composed of individual fuel cells, and more generally refers to use of one or more fuel cell stacks in fluid communication. Individual fuel cell elements (plates) can typically be "stacked" together in a rectangular array called a "fuel cell stack". This fuel cell stack can typically take a feed stream and distribute reactants among all of the individual fuel cell elements and can then collect the products from each of these elements. When viewed as a unit, the fuel cell stack in operation can be taken as a whole even though composed of many (often tens or hundreds) of individual fuel cell elements. These individual fuel cell elements can typically have similar voltages (as the reactant and product concentrations are similar), and the total power output can result from the summation of all of the electrical currents in all of the cell elements, when the elements are electrically connected in series. Stacks can also be arranged in a series arrangement to produce high voltages. A parallel arrangement can boost the current. If a sufficiently large volume fuel cell stack is available to process a given exhaust flow, the systems and methods described herein can be used with a single molten carbonate fuel cell stack. In other aspects of the invention, a plurality of fuel cell stacks may be desirable or needed for a variety of reasons.

For the purposes of this invention, unless otherwise specified, the term "fuel cell" should be understood to also refer to and/or is defined as including a reference to a fuel cell stack composed of set of one or more individual fuel cell elements for which there is a single input and output, as that is the manner in which fuel cells are typically employed in practice. Similarly, the term fuel cells (plural), unless otherwise specified, should be understood to also refer to and/or is defined as including a plurality of separate fuel cell stacks.

In other words, all references within this document, unless specifically noted, can refer interchangeably to the operation of a fuel cell stack as a "fuel cell". For example, the volume of exhaust generated by a commercial scale combustion generator may be too large for processing by a fuel cell (i.e., a single stack) of conventional size. In order to process the full exhaust, a plurality of fuel cells (i.e., two or more separate fuel cells or fuel cell stacks) can be arranged in parallel, so that each fuel cell can process (roughly) an equal portion of the combustion exhaust. Although multiple fuel cells can be used, each fuel cell can typically be operated in a generally similar manner, given its (roughly) equal portion of the combustion exhaust.

"Internal reforming" and "external reforming": A fuel cell or fuel cell stack may include one or more internal reforming sections. As used herein, the term "internal reforming" refers to fuel reforming occurring within the body of a fuel cell, a fuel cell stack, or otherwise within a fuel cell assembly. External reforming, which is often used in conjunction with a fuel cell, occurs in a separate piece of equipment that is located outside of the fuel cell stack. In other words, the body of the external reformer is not in direct physical contact with the body of a fuel cell or fuel cell stack. In a typical set up, the output from the external reformer can be fed to the anode inlet of a fuel cell. Unless otherwise noted specifically, the reforming described within this application is internal reforming.

Internal reforming may occur within a fuel cell anode. Internal reforming can additionally or alternately occur within an internal reforming element integrated within a fuel cell assembly. The integrated reforming element may be located between fuel cell elements within a fuel cell stack. In other words, one of the trays in the stack can be a reforming section instead of a fuel cell element. In one aspect, the flow arrangement within a fuel cell stack directs fuel to the internal reforming elements and then into the anode portion of the fuel cells. Thus, from a flow perspective, the internal reforming elements and fuel cell elements can be arranged in series within the fuel cell stack. As used herein, the term "anode reforming" is fuel reforming that occurs within an anode. As used herein, the term "internal reforming" is reforming that occurs within an integrated reforming element and not in an anode section.

In some aspects, a reforming stage that is internal to a fuel cell assembly can be considered to be associated with the anode(s) in the fuel cell assembly. In some alternative aspects, for a reforming stage in a fuel cell stack that can be associated with an anode (such as associated with multiple anodes), a flow path can be available so that the output flow from the reforming stage is passed into at least one anode. This can correspond to having an initial section of a fuel cell plate that is not in contact with the electrolyte and instead serves just as a reforming catalyst. Another option for an associated reforming stage can be to have a separate integrated reforming stage as one of the elements in a fuel cell stack, where the output from the integrated reforming stage is returned to the input side of one or more of the fuel cells in the fuel cell stack.

From a heat integration standpoint, a characteristic height in a fuel cell stack can be the height of an individual fuel cell stack element. It is noted that the separate reforming stage or a separate endothermic reaction stage could have a different height in the stack than a fuel cell. In such a scenario, the height of a fuel cell element can be used as the characteristic height. In some aspects, an integrated endothermic reaction stage can be defined as a stage that is heat integrated with one or more fuel cells, so that the integrated endothermic reaction stage can use the heat from the fuel cells as a heat source for reforming. Such an integrated endothermic reaction stage can be defined as being positioned less than 5 times the height of a stack element from any fuel cells providing heat to the integrated stage. For example, an integrated endothermic reaction stage (such as a reforming stage) can be positioned less than 5 times the height of a stack element from any fuel cells that are heat integrated, such as less than 3 times the height of a stack element. In this discussion, an integrated reforming stage or integrated endothermic reaction stage that represents an adjacent stack element to a fuel cell element can be defined as being about one stack element height or less away from the adjacent fuel cell element.

In some aspects, a separate reforming stage that is heat integrated with a fuel cell element can also correspond to a reforming stage that is associated with the fuel cell element. In such aspects, an integrated fuel cell element can provide at least a portion of the heat to the associated reforming stage, and the associated reforming stage can provide at least a portion of the reforming stage output to the integrated fuel cell as a fuel stream. In other aspects, a separate reforming stage can be integrated with a fuel cell for heat transfer without being associated with the fuel cell. In this type of situation, the separate reforming stage can receive heat from the fuel cell, but the output of the reforming stage is not used as an input to the fuel cell. Instead, the output of such a reforming stage can be used for another purpose, such as directly adding the output to the anode exhaust stream, or for forming a separate output stream from the fuel cell assembly.

More generally, a separate stack element in a fuel cell stack can be used to perform any convenient type of endothermic reaction that can take advantage of the waste heat provided by integrated fuel cell stack elements. Instead of plates suitable for performing a reforming reaction on a hydrocarbon fuel stream, a separate stack element can have plates suitable for catalyzing another type of endothermic reaction. A manifold or other arrangement of inlet conduits in the fuel cell stack can be used to provide an appropriate input flow to each stack element. A similar manifold or other arrangement of outlet conduits can also be used to withdraw the output flows from each stack element. Optionally, the output flows from a endothermic reaction stage in a stack can be withdrawn from the fuel cell stack without having the output flow pass through a fuel cell anode. In such an optional aspect, the products of the exothermic reaction will therefore exit from the fuel cell stack without passing through a fuel cell anode. Examples of other types of endothermic reactions that can be performed in stack elements in a fuel cell stack include ethanol dehydration to form ethylene and ethane cracking.

Recycle: As defined herein, recycle of a portion of a fuel cell output (such as an anode exhaust or a stream separated or withdrawn from an anode exhaust) to a fuel cell inlet can correspond to a direct or indirect recycle stream. A direct recycle of a stream to a fuel cell inlet is defined as recycle of the stream without passing through an intermediate process, while an indirect recycle involves recycle after passing a stream through one or more intermediate processes. For example, if the anode exhaust is passed through a $CO_2$ separation stage prior to recycle, this is considered an indirect recycle of the anode exhaust. If a portion of the anode exhaust, such as an $H_2$ stream withdrawn from the anode exhaust, is passed into a gasifier for converting coal into a fuel suitable for introduction into the fuel cell, then that is also considered an indirect recycle.

Anode Inputs and Outputs

In various aspects of the invention, the MCFC array can be fed by a fuel received at the anode inlet that comprises, for example, both hydrogen and a hydrocarbon such as methane (or alternatively a hydrocarbonaceous or hydrocarbon-like compound that may contain heteroatoms different from C and H). Most of the methane (or other hydrocarbonaceous or hydrocarbon-like compound) fed to the anode can typically be fresh methane. In this description, a fresh fuel such as fresh methane refers to a fuel that is not recycled from another fuel cell process. For example, methane recycled from the anode outlet stream back to the anode inlet may not be considered "fresh" methane, and can instead be described as reclaimed methane. The fuel source used can be shared with other components, such as a turbine that uses a portion of the fuel source to provide a $CO_2$-containing stream for the cathode input. The fuel source input can include water in a proportion to the fuel appropriate for reforming the hydrocarbon (or hydrocarbon-like) compound in the reforming section that generates hydrogen. For example, if methane is the fuel input for reforming to generate $H_2$, the molar ratio of water to fuel can be from about one to one to about ten to one, such as at least about two to one. A ratio of four to one or greater is typical for external reforming, but lower values can be typical for internal reforming. To the degree that $H_2$ is a portion of the fuel source, in some optional aspects no additional water may be needed in the fuel, as the oxidation of $H_2$ at the anode can tend to produce $H_2O$ that can be used for reforming the fuel. The fuel source can also optionally contain components incidental to the fuel source (e.g., a natural gas feed can contain some content of $CO_2$ as an additional component). For example, a natural gas feed can contain $CO_2$, $N_2$, and/or other inert (noble) gases as additional components. Optionally, in some aspects the fuel source may also contain CO, such as CO from a recycled portion of the anode exhaust. An additional or alternate potential source for CO in the fuel into a fuel cell assembly can be CO generated by steam reforming of a hydrocarbon fuel performed on the fuel prior to entering the fuel cell assembly.

More generally, a variety of types of fuel streams may be suitable for use as an input stream for the anode of a molten carbonate fuel cell. Some fuel streams can correspond to streams containing hydrocarbons and/or hydrocarbon-like compounds that may also include heteroatoms different from C and H. In this discussion, unless otherwise specified, a reference to a fuel stream containing hydrocarbons for an MCFC anode is defined to include fuel streams containing such hydrocarbon-like compounds. Examples of hydrocarbon (including hydrocarbon-like) fuel streams include natural gas, streams containing C1-C4 carbon compounds (such as methane or ethane), and streams containing heavier C5+ hydrocarbons (including hydrocarbon-like compounds), as well as combinations thereof. Still other additional or alternate examples of potential fuel streams for use in an anode input can include biogas-type streams, such as methane produced from natural (biological) decomposition of organic material.

In some aspects, a molten carbonate fuel cell can be used to process an input fuel stream, such as a natural gas and/or hydrocarbon stream, with a low energy content due to the presence of diluent compounds. For example, some sources of methane and/or natural gas are sources that can include substantial amounts of either $CO_2$ or other inert molecules, such as nitrogen, argon, or helium. Due to the presence of elevated amounts of $CO_2$ and/or inerts, the energy content of a fuel stream based on the source can be reduced. Using a low energy content fuel for a combustion reaction (such as for powering a combustion-powered turbine) can pose difficulties. However, a molten carbonate fuel cell can generate power based on a low energy content fuel source with a reduced or minimal impact on the efficiency of the fuel cell. The presence of additional gas volume can require additional heat for raising the temperature of the fuel to the temperature for reforming and/or the anode reaction. Additionally, due to the equilibrium nature of the water gas shift reaction within a fuel cell anode, the presence of additional $CO_2$ can have an impact on the relative amounts of $H_2$ and CO present in the anode output. However, the inert compounds otherwise can have only a minimal direct impact on the reforming and anode reactions. The amount of $CO_2$ and/or inert compounds in a fuel stream for a molten carbonate fuel cell, when present, can be at least about 1 vol %, such as at least about 2 vol %, or at least about 5 vol %, or at least about 10 vol %, or at least about 15 vol %, or at least about 20 vol %, or at least about 25 vol %, or at least about 30 vol %, or at least about 35 vol %, or at least about 40 vol %, or at least about 45 vol %, or at least about 50 vol %, or at least about 75 vol %. Additionally or alternately, the amount of $CO_2$ and/or inert compounds in a fuel stream for a molten carbonate fuel cell can be about 90 vol % or less, such as about 75 vol % or less, or about 60 vol % or less, or about 50 vol % or less, or about 40 vol % or less, or about 35 vol % or less.

Yet other examples of potential sources for an anode input stream can correspond to refinery and/or other industrial process output streams. For example, coking is a common process in many refineries for converting heavier compounds to lower boiling ranges. Coking typically produces an off-gas containing a variety of compounds that are gases at room temperature, including CO and various C1-C4 hydrocarbons. This off-gas can be used as at least a portion of an anode input stream. Other refinery off-gas streams can additionally or alternately be suitable for inclusion in an anode input stream, such as light ends (C1-C4) generated during cracking or other refinery processes. Still other suitable refinery streams can additionally or alternately include refinery streams containing CO or $CO_2$ that also contain $H_2$ and/or reformable fuel compounds.

Still other potential sources for an anode input can additionally or alternatively include streams with increased water content. For example, an ethanol output stream from an ethanol plant (or another type of fermentation process) can include a substantial portion of $H_2O$ prior to final distillation. Such $H_2O$ can typically cause only minimal impact on the operation of a fuel cell. Thus, a fermentation mixture of alcohol (or other fermentation product) and water can be used as at least a portion of an anode input stream.

Biogas, or digester gas, is another additional or alternate potential source for an anode input. Biogas may primarily comprise methane and $CO_2$ and is typically produced by the breakdown or digestion of organic matter. Anaerobic bacteria may be used to digest the organic matter and produce the biogas. Impurities, such as sulfur-containing compounds, may be removed from the biogas prior to use as an anode input.

The output stream from an MCFC anode can include $H_2O$, $CO_2$, CO, and $H_2$. Optionally, the anode output stream could also have unreacted fuel (such as $H_2$ or $CH_4$) or inert compounds in the feed as additional output components. Instead of using this output stream as a fuel source to provide heat for a reforming reaction or as a combustion fuel for heating the cell, one or more separations can be performed on the anode output stream to separate the $CO_2$ from the components with potential value as inputs to another process, such as $H_2$ or CO. The $H_2$ and/or CO can be used as a syngas for chemical synthesis, as a source of hydrogen for chemical reaction, and/or as a fuel with reduced greenhouse gas emissions.

In various aspects, the composition of the output stream from the anode can be impacted by several factors. Factors that can influence the anode output composition can include the composition of the input stream to the anode, the amount of current generated by the fuel cell, and/or the temperature at the exit of the anode. The temperature of at the anode exit can be relevant due to the equilibrium nature of the water gas shift reaction. In a typical anode, at least one of the plates forming the wall of the anode can be suitable for catalyzing the water gas shift reaction. As a result, if a) the composition of the anode input stream is known, b) the extent of reforming of reformable fuel in the anode input stream is known, and c) the amount of carbonate transported from the cathode to anode (corresponding to the amount of electrical current generated) is known, the composition of the anode output can be determined based on the equilibrium constant for the water gas shift reaction.

$$K_{eq}=[CO_2][H_2]/[CO][H_2O]$$

In the above equation, $K_{eq}$ is the equilibrium constant for the reaction at a given temperature and pressure, and [X] is the partial pressure of component X. Based on the water gas shift reaction, it can be noted that an increased $CO_2$ concentration in the anode input can tend to result in additional CO formation (at the expense of $H_2$) while an increased $H_2O$ concentration can tend to result in additional $H_2$ formation (at the expense of CO).

To determine the composition at the anode output, the composition of the anode input can be used as a starting point. This composition can then be modified to reflect the extent of reforming of any reformable fuels that can occur within the anode. Such reforming can reduce the hydrocarbon content of the anode input in exchange for increased hydrogen and $CO_2$. Next, based on the amount of electrical current generated, the amount of $H_2$ in the anode input can be reduced in exchange for additional $H_2O$ and $CO_2$. This composition can then be adjusted based on the equilibrium constant for the water gas shift reaction to determine the exit concentrations for $H_2$, CO, $CO_2$, and $H_2O$.

Table 1 shows the anode exhaust composition at different fuel utilizations for a typical type of fuel. The anode exhaust composition can reflect the combined result of the anode reforming reaction, water gas shift reaction, and the anode oxidation reaction. The output composition values in Table 1 were calculated by assuming an anode input composition with an about 2 to 1 ratio of steam ($H_2O$) to carbon (reformable fuel). The reformable fuel was assumed to be methane, which was assumed to be 100% reformed to hydrogen. The initial $CO_2$ and $H_2$ concentrations in the anode input were assumed to be negligible, while the input $N_2$ concentration was about 0.5%. The fuel utilization $U_f$ (as defined herein) was allowed to vary from about 35% to about 70% as shown in the table. The exit temperature for the fuel cell anode was assumed to be about 650° C. for purposes of determining the correct value for the equilibrium constant.

TABLE 1

| Uf | % | 35% | 40% | 45% | 50% | 55% | 60% | 65% | 70% |
|---|---|---|---|---|---|---|---|---|---|
| | | | | Anode Exhaust Composition | | | | | |
| $H_2O$ | %, wet | 32.5% | 34.1% | 35.5% | 36.7% | 37.8% | 38.9% | 39.8% | 40.5% |
| $CO_2$ | %, wet | 26.7% | 29.4% | 32.0% | 34.5% | 36.9% | 39.3% | 41.5% | 43.8% |
| $H_2$ | %, wet | 29.4% | 26.0% | 22.9% | 20.0% | 17.3% | 14.8% | 12.5% | 10.4% |
| CO | %, wet | 10.8% | 10.0% | 9.2% | 8.4% | 7.5% | 6.7% | 5.8% | 4.9% |
| $N_2$ | %, wet | 0.5% | 0.5% | 0.5% | 0.4% | 0.4% | 0.4% | 0.4% | 0.4% |
| $CO_2$ | %, dry | 39.6% | 44.6% | 49.6% | 54.5% | 59.4% | 64.2% | 69.0% | 73.7% |
| $H_2$ | %, dry | 43.6% | 39.4% | 35.4% | 31.5% | 27.8% | 24.2% | 20.7% | 17.5% |
| CO | %, dry | 16.1% | 15.2% | 14.3% | 13.2% | 12.1% | 10.9% | 9.7% | 8.2% |
| $N_2$ | %, dry | 0.7% | 0.7% | 0.7% | 0.7% | 0.7% | 0.7% | 0.7% | 0.7% |
| $H_2$/CO | | 2.7 | 2.6 | 2.5 | 2.4 | 2.3 | 2.2 | 2.1 | 2.1 |
| $(H_2 - CO_2)/(CO + CO_2)$ | | 0.07 | −0.09 | −0.22 | −0.34 | −0.44 | −0.53 | −0.61 | −0.69 |

Table 1 shows anode output compositions for a particular set of conditions and anode input composition. More generally, in various aspects the anode output can include about 10 vol % to about 50 vol % $H_2O$. The amount of $H_2O$ can vary greatly, as $H_2O$ in the anode can be produced by the anode oxidation reaction. If an excess of $H_2O$ beyond what is needed for reforming is introduced into the anode, the excess $H_2O$ can typically pass through largely unreacted, with the exception of $H_2O$ consumed (or generated) due to fuel reforming and the water gas shift reaction. The $CO_2$ concentration in the anode output can also vary widely, such as from about 20 vol % to about 50 vol % $CO_2$. The amount of $CO_2$ can be influenced by both the amount of electrical current generated as well as the amount of $CO_2$ in the anode input flow. The amount of $H_2$ in the anode output can additionally or alternately be from about 10 vol % $H_2$ to about 50 vol % $H_2$, depending on the fuel utilization in the anode. At the anode output, the amount of CO can be from about 5 vol % to about 20 vol %. It is noted that the amount of CO relative to the amount of $H_2$ in the anode output for a given fuel cell can be determined in part by the equilibrium constant for the water gas shift reaction at the temperature and pressure present in the fuel cell. The anode output can further additionally or alternately include 5 vol % or less of various other components, such as $N_2$, $CH_4$ (or other unreacted carbon-containing fuels), and/or other components.

Optionally, one or more water gas shift reaction stages can be included after the anode output to convert CO and $H_2O$ in the anode output into $CO_2$ and $H_2$, if desired. The amount of $H_2$ present in the anode output can be increased, for example, by using a water gas shift reactor at lower temperature to convert $H_2O$ and CO present in the anode output into $H_2$ and $CO_2$. Alternatively, the temperature can be raised and the water-gas shift reaction can be reversed, producing more CO and $H_2O$ from $H_2$ and $CO_2$. Water is an expected output of the reaction occurring at the anode, so the anode output can typically have an excess of $H_2O$ relative to the amount of CO present in the anode output. Alternatively, $H_2O$ can be added to the stream after the anode exit but before the water gas shift reaction. CO can be present in the anode output due to incomplete carbon conversion during reforming and/or due to the equilibrium balancing reactions between $H_2O$, CO, $H_2$, and $CO_2$ (i.e., the water-gas shift equilibrium) under either reforming conditions or the conditions present during the anode reaction. A water gas shift reactor can be operated under conditions to drive the equilibrium further in the direction of forming $CO_2$ and $H_2$ at the expense of CO and $H_2O$. Higher temperatures can tend to favor the formation of CO and $H_2O$. Thus, one option for operating the water gas shift reactor can be to expose the anode output stream to a suitable catalyst, such as a catalyst including iron oxide, zinc oxide, copper on zinc oxide, or the like, at a suitable temperature, e.g., between about 190° C. to about 210° C. Optionally, the water-gas shift reactor can include two stages for reducing the CO concentration in an anode output stream, with a first higher temperature stage operated at a temperature from at least about 300° C. to about 375° C. and a second lower temperature stage operated at a temperature of about 225° C. or less, such as from about 180° C. to about 210° C. In addition to increasing the amount of $H_2$ present in the anode output, the water-gas shift reaction can additionally or alternately increase the amount of $CO_2$ at the expense of CO. This can exchange difficult-to-remove carbon monoxide (CO) for carbon dioxide, which can be more readily removed by condensation (e.g., cryogenic removal), chemical reaction (such as amine removal), and/or other $CO_2$ removal methods. Additionally or alternately, it may be desirable to increase the CO content present in the anode exhaust in order to achieve a desired ratio of $H_2$ to CO.

After passing through the optional water gas shift reaction stage, the anode output can be passed through one or more separation stages for removal of water and/or $CO_2$ from the anode output stream. For example, one or more $CO_2$ output streams can be formed by performing $CO_2$ separation on the anode output using one or more methods individually or in combination. Such methods can be used to generate $CO_2$ output stream(s) having a $CO_2$ content of 90 vol % or greater, such as at least 95% vol % $CO_2$, or at least 98 vol % $CO_2$. Such methods can recover about at least about 70% of the $CO_2$ content of the anode output, such as at least about 80% of the $CO_2$ content of the anode output, or at least about 90%. Alternatively, in some aspects it may be desirable to recover only a portion of the $CO_2$ within an anode output stream, with the recovered portion of $CO_2$ being about 33% to about 90% of the $CO_2$ in the anode output, such as at least about 40%, or at least about 50%. For example, it may be desirable to retain some $CO_2$ in the anode output flow so that a desired composition can be achieved in a subsequent water gas shift stage. Suitable separation methods may comprise use of a physical solvent (e.g., Selexol™ or Rectisol™); amines or other bases (e.g., MEA or MDEA); refrigeration (e.g., cryogenic separation); pressure swing adsorption; vacuum swing adsorption; and combinations thereof. A cryogenic $CO_2$ separator can be an example of a suitable separator. As the anode output is cooled, the majority of the water in the anode output can be separated out as a condensed (liquid) phase. Further cooling and/or pressurizing of the water-depleted anode output flow can then separate high purity $CO_2$, as the other remaining components in the anode output flow (such as $H_2$, $N_2$, $CH_4$) do not tend to readily form condensed phases. A cryogenic $CO_2$ separator can recover between about 33% and about 90% of the $CO_2$ present in a flow, depending on the operating conditions.

Removal of water from the anode exhaust to form one or more water output streams can also be beneficial, whether prior to, during, or after performing $CO_2$ separation. The amount of water in the anode output can vary depending on operating conditions selected. For example, the steam-to-carbon ratio established at the anode inlet can affect the water content in the anode exhaust, with high steam-to-carbon ratios typically resulting in a large amount of water that can pass through the anode unreacted and/or reacted only due to the water gas shift equilibrium in the anode. Depending on the aspect, the water content in the anode exhaust can correspond to up to about 30% or more of the volume in the anode exhaust. Additionally or alternately, the water content can be about 80% or less of the volume of the anode exhaust. While such water can be removed by compression and/or cooling with resulting condensation, the removal of this water can require extra compressor power and/or heat exchange surface area and excessive cooling water. One beneficial way to remove a portion of this excess water can be based on use of an adsorbent bed that can capture the humidity from the moist anode effluent and can then be 'regenerated' using dry anode feed gas, in order to provide additional water for the anode feed. HVAC-style (heating, ventilation, and air conditioning) adsorption wheels design can be applicable, because anode exhaust and inlet can be similar in pressure, and minor leakage from one stream to the other can have minimal impact on the overall process. In embodiments where $CO_2$ removal is performed using a cryogenic process, removal of water prior to or during $CO_2$ removal may be desirable, including removal by triethyleneglycol (TEG) system and/or desiccants. By contrast, if an amine wash is used for $CO_2$ removal, water can be removed from the anode exhaust downstream from the $CO_2$ removal stage.

Alternately or in addition to a $CO_2$ output stream and/or a water output stream, the anode output can be used to form one or more product streams containing a desired chemical or fuel product. Such a product stream or streams can correspond to a syngas stream, a hydrogen stream, or both syngas product and hydrogen product streams. For example, a hydrogen product stream containing at least about 70 vol % $H_2$, such as at least about 90 vol % $H_2$ or at least about 95 vol % $H_2$, can be formed. Additionally or alternately, a syngas stream containing at least about 70 vol % of $H_2$ and CO combined, such as at least about 90 vol % of $H_2$ and CO can be formed. The one or more product streams can have a gas volume corresponding to at least about 75% of the combined $H_2$ and CO gas volumes in the anode output, such as at least about 85% or at least about 90% of the combined $H_2$ and CO gas volumes. It is noted that the relative amounts of $H_2$ and CO in the products streams may differ from the $H_2$ to CO ratio in the anode output based on use of water gas shift reaction stages to convert between the products.

In some aspects, it can be desirable to remove or separate a portion of the $H_2$ present in the anode output. For example, in some aspects the $H_2$ to CO ratio in the anode exhaust can be at least about 3.0:1. By contrast, processes that make use of syngas, such as Fischer-Tropsch synthesis, may consume $H_2$ and CO in a different ratio, such as a ratio that is closer to 2:1. One alternative can be to use a water gas shift reaction to modify the content of the anode output to have an $H_2$ to CO ratio closer to a desired syngas composition. Another alternative can be to use a membrane separation to remove a portion of the $H_2$ present in the anode output to achieve a desired ratio of $H_2$ and CO, or still alternately to use a combination of membrane separation and water gas shift reactions. One advantage of using a membrane separation to remove only a portion of the $H_2$ in the anode output can be that the desired separation can be performed under relatively mild conditions. Since one goal can be to produce a retentate that still has a substantial $H_2$ content, a permeate of high purity hydrogen can be generated by membrane separation without requiring severe conditions. For example, rather than having a pressure on the permeate side of the membrane of about 100 kPaa or less (such as ambient pressure), the permeate side can be at an elevated pressure relative to ambient while still having sufficient driving force to perform the membrane separation. Additionally or alternately, a sweep gas such as methane can be used to provide a driving force for the membrane separation. This can reduce the purity of the $H_2$ permeate stream, but may be advantageous, depending on the desired use for the permeate stream.

In various aspects of the invention, at least a portion of the anode exhaust stream (preferably after separation of $CO_2$ and/or $H_2O$) can be used as a feed for a process external to the fuel cell and associated reforming stages. In various aspects, the anode exhaust can have a ratio of $H_2$ to CO of about 1.5:1 to about 10:1, such as at least about 3.0:1, or at least about 4.0:1, or at least about 5.0:1. A syngas stream can be generated or withdrawn from the anode exhaust. The anode exhaust gas, optionally after separation of $CO_2$ and/or $H_2O$, and optionally after performing a water gas shift reaction and/or a membrane separation to remove excess hydrogen, can correspond to a stream containing substantial portions of $H_2$ and/or CO. For a stream with a relatively low content of CO, such as a stream where the ratio of $H_2$ to CO is at least about 3:1, the anode exhaust can be suitable for use as an $H_2$ feed. Examples of processes that could benefit from an $H_2$ feed can include, but are not limited to, refinery processes, an ammonia synthesis plant, or a turbine in a (different) power generation system, or combinations thereof. Depending on the application, still lower $CO_2$ contents can be desirable. For a stream with an $H_2$-to-CO ratio of less than about 2.2 to 1 and greater than about 1.9 to 1, the stream can be suitable for use as a syngas feed. Examples of processes that could benefit from a syngas feed can include, but are not limited to, a gas-to-liquids plant (such as a plant using a Fischer-Tropsch process with a non-shifting catalyst) and/or a methanol synthesis plant. The amount of the anode exhaust used as a feed for an external process can be any convenient amount. Optionally, when a portion of the anode exhaust is used as a feed for an external process, a second portion of the anode exhaust can be recycled to the anode input and/or recycled to the combustion zone for a combustion-powered generator.

The input streams useful for different types of Fischer-Tropsch synthesis processes can provide an example of the different types of product streams that may be desirable to generate from the anode output. For a Fischer-Tropsch synthesis reaction system that uses a shifting catalyst, such as an iron-based catalyst, the desired input stream to the reaction system can include $CO_2$ in addition to $H_2$ and CO. If a sufficient amount of $CO_2$ is not present in the input stream, a Fischer-Tropsch catalyst with water gas shift activity can consume CO in order to generate additional $CO_2$, resulting in a syngas that can be deficient in CO. For integration of such a Fischer-Tropsch process with an MCFC fuel cell, the separation stages for the anode output can be operated to retain a desired amount of $CO_2$ (and optionally $H_2O$) in the syngas product. By contrast, for a Fischer-Tropsch catalyst based on a non-shifting catalyst, any $CO_2$ present in a product stream could serve as an inert component in the Fischer-Tropsch reaction system.

In an aspect where the membrane is swept with a sweep gas such as a methane sweep gas, the methane sweep gas can correspond to a methane stream used as the anode fuel or in a different low pressure process, such as a boiler, furnace, gas turbine, or other fuel-consuming device. In such an aspect, low levels of $CO_2$ permeation across the membrane can have minimal consequence. Such $CO_2$ that may permeate across the membrane can have a minimal impact on the reactions within the anode, and such $CO_2$ can remain contained in the anode product. Therefore, the $CO_2$ (if any) lost across the membrane due to permeation does not need to be transferred again across the MCFC electrolyte. This can significantly reduce the separation selectivity requirement for the hydrogen permeation membrane. This can allow, for example, use of a higher-permeability membrane having a lower selectivity, which can enable use of a lower pressure and/or reduced membrane surface area. In such an aspect of the invention, the volume of the sweep gas can be a large multiple of the volume of hydrogen in the anode exhaust, which can allow the effective hydrogen concentration on the permeate side to be maintained close to zero. The hydrogen thus separated can be incorporated into the turbine-fed methane where it can enhance the turbine combustion characteristics, as described above.

It is noted that excess $H_2$ produced in the anode can represent a fuel where the greenhouse gases have already been separated. Any $CO_2$ in the anode output can be readily separated from the anode output, such as by using an amine wash, a cryogenic $CO_2$ separator, and/or a pressure or vacuum swing absorption process. Several of the components of the anode output ($H_2$, CO, $CH_4$) are not easily removed, while $CO_2$ and $H_2O$ can usually be readily removed. Depending on the embodiment, at least about 90 vol % of the $CO_2$ in the anode output can be separated out to form a relatively high purity $CO_2$ output stream. Thus, any $CO_2$ generated in the anode can be efficiently separated out to form a high purity $CO_2$ output stream. After separation, the remaining portion of the anode output can correspond primarily to components with chemical and/or fuel value, as well as reduced amounts of $CO_2$ and/or $H_2O$, Since a substantial portion of the $CO_2$ generated by the original fuel (prior to reforming) can have been separated out, the amount of $CO_2$ generated by subsequent burning of the remaining portion of the anode output can be reduced. In particular, to the degree that the fuel in the remaining portion of the anode output is $H_2$, no additional greenhouse gases can typically be formed by burning of this fuel.

The anode exhaust can be subjected to a variety of gas processing options, including water-gas shift and separation of the components from each other. Two general anode processing schemes are shown in FIGS. 1 and 2.

Figure 2:
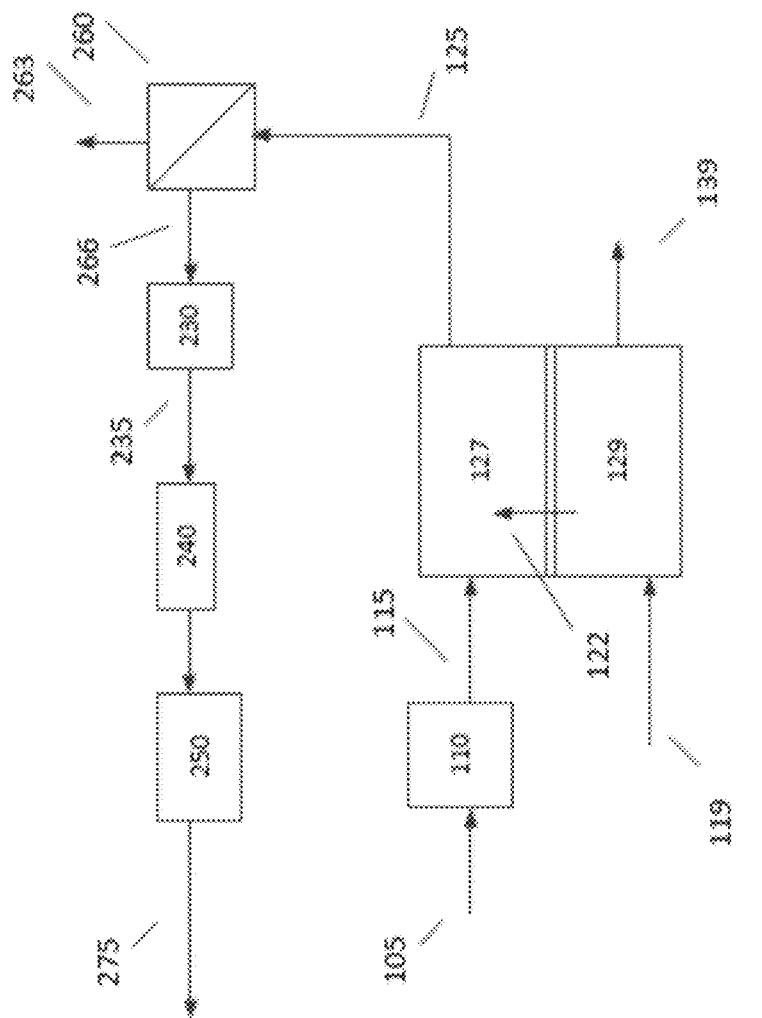
FIG. 2 schematically shows another example of a configuration for molten carbonate fuel cells and associated reforming and separation stages.

FIG. 1 schematically shows an example of a reaction system for operating a fuel cell array of molten carbonate fuel cells in conjunction with a chemical synthesis process. In FIG. 1, a fuel stream 105 is provided to a reforming stage (or stages) 110 associated with the anode 127 of a fuel cell 120, such as a fuel cell that is part of a fuel cell stack in a fuel cell array. The reforming stage 110 associated with fuel cell 120 can be internal to a fuel cell assembly. In some optional aspects, an external reforming stage (not shown) can also be used to reform a portion of the reformable fuel in an input stream prior to passing the input stream into a fuel cell assembly. Fuel stream 105 can preferably include a reformable fuel, such as methane, other hydrocarbons, and/or other hydrocarbon-like compounds such as organic compounds containing carbon-hydrogen bonds. Fuel stream 105 can also optionally contain $H_2$ and/or CO, such as $H_2$ and/or CO provided by optional anode recycle stream 185. It is noted that anode recycle stream 185 is optional, and that in many aspects no recycle stream is provided from the anode exhaust 125 back to anode 127, either directly or indirectly via combination with fuel stream 105 or reformed fuel stream 115. After reforming, the reformed fuel stream 115 can be passed into anode 127 of fuel cell 120. A $CO_2$ and $O_2$-containing stream 119 can also be passed into cathode 129. A flow of carbonate ions 122, $CO_3^{2-}$, from the cathode portion 129 of the fuel cell can provide the remaining reactant needed for the anode fuel cell reactions. Based on the reactions in the anode 127, the resulting anode exhaust 125 can include $H_2O$, $CO_2$, one or more components corresponding to incompletely reacted fuel ($H_2$, CO, $CH_4$, or other components corresponding to a reformable fuel), and optionally one or more additional nonreactive components, such as $N_2$ and/or other contaminants that are part of fuel stream 105. The anode exhaust 125 can then be passed into one or more separation stages. For example, a $CO_2$ removal stage 140 can correspond to a cryogenic $CO_2$ removal system, an amine wash stage for removal of acid gases such as $CO_2$, or another suitable type of $CO_2$ separation stage for separating a $CO_2$ output stream 143 from the anode exhaust. Optionally, the anode exhaust can first be passed through a water gas shift reactor 130 to convert any CO present in the anode exhaust (along with some $H_2O$) into $CO_2$ and $H_2$ in an optionally water gas shifted anode exhaust 135. Depending on the nature of the $CO_2$ removal stage, a water condensation or removal stage 150 may be desirable to remove a water output stream 153 from the anode exhaust. Though shown in FIG. 1 after the $CO_2$ separation stage 140, it may optionally be located before the $CO_2$ separation stage 140 instead. Additionally, an optional membrane separation stage 160 for separation of $H_2$ can be used to generate a high purity permeate stream 163 of $H_2$. The resulting retentate stream 166 can then be used as an input to a chemical synthesis process. Stream 166 could additionally or alternately be shifted in a second water-gas shift reactor 131 to adjust the $H_2$, CO, and $CO_2$ content to a different ratio, producing an output stream 168 for further use in a chemical synthesis process. In FIG. 1, anode recycle stream 185 is shown as being withdrawn from the retentate stream 166, but the anode recycle stream 185 could additionally or alternately be withdrawn from other convenient locations in or between the various separation stages. The separation stages and shift reactor(s) could additionally or alternately be configured in different orders, and/or in a parallel configuration. Finally, a stream with a reduced content of $CO_2$ 139 can be generated as an output from cathode 129. For the sake of simplicity, various stages of compression and heat addition/removal that might be useful in the process, as well as steam addition or removal, are not shown.

As noted above, the various types of separations performed on the anode exhaust can be performed in any convenient order. FIG. 2 shows an example of an alternative order for performing separations on an anode exhaust. In FIG. 2, anode exhaust 125 can be initially passed into separation stage 260 for removing a portion 263 of the hydrogen content from the anode exhaust 125. This can allow, for example, reduction of the $H_2$ content of the anode exhaust to provide a retentate 266 with a ratio of $H_2$ to CO closer to 2:1. The ratio of $H_2$ to CO can then be further adjusted to achieve a desired value in a water gas shift stage 230. The water gas shifted output 235 can then pass through $CO_2$ separation stage 240 and water removal stage 250 to produce an output stream 275 suitable for use as an input to a desired chemical synthesis process. Optionally, output stream 275 could be exposed to an additional water gas shift stage (not shown). A portion of output stream 275 can optionally be recycled (not shown) to the anode input. Of course, still other combinations and sequencing of separation stages can be used to generate a stream based on the anode output that has a desired composition. For the sake of simplicity, various stages of compression and heat addition/removal that might be useful in the process, as well as steam addition or removal, are not shown.

Cathode Inputs and Outputs

Conventionally, a molten carbonate fuel cell can be operated based on drawing a desired load while consuming some portion of the fuel in the fuel stream delivered to the anode. The voltage of the fuel cell can then be determined by the load, fuel input to the anode, air and $CO_2$ provided to the cathode, and the internal resistances of the fuel cell. The $CO_2$ to the cathode can be conventionally provided in part by using the anode exhaust as at least a part of the cathode input stream. By contrast, the present invention can use separate/different sources for the anode input and cathode input. By removing any direct link between the composition of the anode input flow and the cathode input flow, additional options become available for operating the fuel cell, such as to generate excess synthesis gas, to improve capture of carbon dioxide, and/or to improve the total efficiency (electrical plus chemical power) of the fuel cell, among others.

In a molten carbonate fuel cell, the transport of carbonate ions across the electrolyte in the fuel cell can provide a method for transporting $CO_2$ from a first flow path to a second flow path, where the transport method can allow transport from a lower concentration (the cathode) to a higher concentration (the anode), which can thus facilitate capture of $CO_2$. Part of the selectivity of the fuel cell for $CO_2$ separation can be based on the electrochemical reactions allowing the cell to generate electrical power. For nonreactive species (such as $N_2$) that effectively do not participate in the electrochemical reactions within the fuel cell, there can be an insignificant amount of reaction and transport from cathode to anode. By contrast, the potential (voltage) difference between the cathode and anode can provide a strong driving force for transport of carbonate ions across the fuel cell. As a result, the transport of carbonate ions in the molten carbonate fuel cell can allow $CO_2$ to be transported from the cathode (lower $CO_2$ concentration) to the anode (higher $CO_2$ concentration) with relatively high selectivity. However, a challenge in using molten carbonate fuel cells for carbon dioxide removal can be that the fuel cells have limited ability to remove carbon dioxide from relatively dilute cathode feeds. The voltage and/or power generated by a carbonate fuel cell can start to drop rapidly as the $CO_2$ concentration falls below about 2.0 vol %. As the $CO_2$ concentration drops further, e.g., to below about 1.0 vol %, at some point the voltage across the fuel cell can become low enough that little or no further transport of carbonate may occur and the fuel cell ceases to function. Thus, at least some $CO_2$ is likely to be present in the exhaust gas from the cathode stage of a fuel cell under commercially viable operating conditions.

The amount of carbon dioxide delivered to the fuel cell cathode(s) can be determined based on the $CO_2$ content of a source for the cathode inlet. One example of a suitable $CO_2$-containing stream for use as a cathode input flow can be an output or exhaust flow from a combustion source. Examples of combustion sources include, but are not limited to, sources based on combustion of natural gas, combustion of coal, and/or combustion of other hydrocarbon-type fuels (including biologically derived fuels). Additional or alternate sources can include other types of boilers, fired heaters, furnaces, and/or other types of devices that burn carbon-containing fuels in order to heat another substance (such as water or air). To a first approximation, the $CO_2$ content of the output flow from a combustion source can be a minor portion of the flow. Even for a higher $CO_2$ content exhaust flow, such as the output from a coal-fired combustion source, the $CO_2$ content from most commercial coal-fired power plants can be about 15 vol % or less. More generally, the $CO_2$ content of an output or exhaust flow from a combustion source can be at least about 1.5 vol %, or at least about 1.6 vol %, or at least about 1.7 vol %, or at least about 1.8 vol %, or at least about 1.9 vol %, or at least greater 2 vol %, or at least about 4 vol %, or at least about 5 vol %, or at least about 6 vol %, or at least about 8 vol %. Additionally or alternately, the $CO_2$ content of an output or exhaust flow from a combustion source can be about 20 vol % or less, such as about 15 vol % or less, or about 12 vol % or less, or about 10 vol % or less, or about 9 vol % or less, or about 8 vol % or less, or about 7 vol % or less, or about 6.5 vol % or less, or about 6 vol % or less, or about 5.5 vol % or less, or about 5 vol % or less, or about 4.5 vol % or less. The concentrations given above are on a dry basis. It is noted that the lower $CO_2$ content values can be present in the exhaust from some natural gas or methane combustion sources, such as generators that are part of a power generation system that may or may not include an exhaust gas recycle loop.

Other potential sources for a cathode input stream can additionally or alternately include sources of bio-produced $CO_2$. This can include, for example, $CO_2$ generated during processing of bio-derived compounds, such as $CO_2$ generated during ethanol production. An additional or alternate example can include $CO_2$ generated by combustion of a bio-produced fuel, such as combustion of lignocellulose. Still other additional or alternate potential $CO_2$ sources can correspond to output or exhaust streams from various industrial processes, such as $CO_2$-containing streams generated by plants for manufacture of steel, cement, and/or paper.

Yet another additional or alternate potential source of $CO_2$ can be $CO_2$-containing streams from a fuel cell. The $CO_2$-containing stream from a fuel cell can correspond to a cathode output stream from a different fuel cell, an anode output stream from a different fuel cell, a recycle stream from the cathode output to the cathode input of a fuel cell, and/or a recycle stream from an anode output to a cathode input of a fuel cell. For example, an MCFC operated in standalone mode under conventional conditions can generate a cathode exhaust with a $CO_2$ concentration of at least about 5 vol %. Such a $CO_2$-containing cathode exhaust could be used as a cathode input for an MCFC operated according to an aspect of the invention. More generally, other types of fuel cells that generate a $CO_2$ output from the cathode exhaust can additionally or alternatively be used, as well as other types of $CO_2$-containing streams not generated by a "combustion" reaction and/or by a combustion-powered generator. Optionally but preferably, a $CO_2$-containing stream from another fuel cell can be from another molten carbonate fuel cell. For example, for molten carbonate fuel cells connected in series with respect to the cathodes, the output from the cathode for a first molten carbonate fuel cell can be used as the input to the cathode for a second molten carbonate fuel cell.

For various types of $CO_2$-containing streams from sources other than combustion sources, the $CO_2$ content of the stream can vary widely. The $CO_2$ content of an input stream to a cathode can contain at least about 2 vol % of $CO_2$, such as at least about 4 vol %, or at least about 5 vol %, or at least about 6 vol %, or at least about 8 vol %. Additionally or alternatively, the $CO_2$ content of an input stream to a cathode can be about 30 vol % or less, such as about 25 vol % or less, or about 20 vol % or less, or about 15 vol % or less, or about 10 vol % or less, or about 8 vol % or less, or about 6 vol % or less, or about 4 vol % or less. For some still higher $CO_2$ content streams, the $CO_2$ content can be greater than about 30 vol %, such as a stream substantially composed of $CO_2$ with only incidental amounts of other compounds. As an example, a gas-fired turbine without exhaust gas recycle can produce an exhaust stream with a $CO_2$ content of approximately 4.2 vol %. With EGR, a gas-fired turbine can produce an exhaust stream with a $CO_2$ content of about 6-8 vol %. Stoichiometric combustion of methane can produce an exhaust stream with a $CO_2$ content of about 11 vol %. Combustion of coal can produce an exhaust stream with a $CO_2$ content of about 15-20 vol %. Fired heaters using refinery off-gas can produce an exhaust stream with a $CO_2$ content of about 12-15 vol %. A gas turbine operated on a low BTU gas without any EGR can produce an exhaust stream with a $CO_2$ content of ~12 vol %.

In addition to $CO_2$, a cathode input stream must include $O_2$ to provide the components necessary for the cathode reaction. Some cathode input streams can be based on having air as a component. For example, a combustion exhaust stream can be formed by combusting a hydrocarbon fuel in the presence of air. Such a combustion exhaust stream, or another type of cathode input stream having an oxygen content based on inclusion of air, can have an oxygen content of about 20 vol % or less, such as about 15 vol % or less, or about 10 vol % or less. Additionally or alternatively, the oxygen content of the cathode input stream can be at least about 4 vol %, such as at least about 6 vol %, or at least about 8 vol %. More generally, a cathode input stream can have a suitable content of oxygen for performing the cathode reaction. In some aspects, this can correspond to an oxygen content of about 5 vol % to about 15 vol %, such as from about 7 vol % to about 9 vol %. For many types of cathode input streams, the combined amount of $CO_2$ and $O_2$ can correspond to less than about 21 vol % of the input stream, such as less than about 15 vol % of the stream or less than about 10 vol % of the stream. An air stream containing oxygen can be combined with a $CO_2$ source that has low oxygen content. For example, the exhaust stream generated by burning coal may include a low oxygen content that can be mixed with air to form a cathode inlet stream.

In addition to $CO_2$ and $O_2$, a cathode input stream can also be composed of inert/non-reactive species such as $N_2$, $H_2O$, and other typical oxidant (air) components. For example, for a cathode input derived from an exhaust from a combustion reaction, if air is used as part of the oxidant source for the combustion reaction, the exhaust gas can include typical components of air such as $N_2$, $H_2O$, and other compounds in minor amounts that are present in air. Depending on the nature of the fuel source for the combustion reaction, additional species present after combustion based on the fuel source may include one or more of $H_2O$, oxides of nitrogen (NOx) and/or sulfur (SOx), and other compounds either present in the fuel and/or that are partial or complete combustion products of compounds present in the fuel, such as CO. These species may be present in amounts that do not poison the cathode catalyst surfaces though they may reduce the overall cathode activity. Such reductions in performance may be acceptable, or species that interact with the cathode catalyst may be reduced to acceptable levels by known pollutant removal technologies.

The amount of $O_2$ present in a cathode input stream (such as an input cathode stream based on a combustion exhaust) can advantageously be sufficient to provide the oxygen needed for the cathode reaction in the fuel cell. Thus, the volume percentage of $O_2$ can advantageously be at least 0.5 times the amount of $CO_2$ in the exhaust. Optionally, as necessary, additional air can be added to the cathode input to provide sufficient oxidant for the cathode reaction. When some form of air is used as the oxidant, the amount of $N_2$ in the cathode exhaust can be at least about 78 vol %, e.g., at least about 88 vol %, and/or about 95 vol % or less. In some aspects, the cathode input stream can additionally or alternately contain compounds that are generally viewed as contaminants, such as $H_2S$ or $NH_3$. In other aspects, the cathode input stream can be cleaned to reduce or minimize the content of such contaminants.

In addition to the reaction to form carbonate ions for transport across the electrolyte, the conditions in the cathode can also be suitable for conversion of nitrogen oxides into nitrate and/or nitrate ions. Hereinafter, only nitrate ions will be referred to for convenience. The resulting nitrate ions can also be transported across the electrolyte for reaction in the anode. NOx concentrations in a cathode input stream can typically be on the order of ppm, so this nitrate transport reaction can have a minimal impact on the amount of carbonate transported across the electrolyte. However, this method of NOx removal can be beneficial for cathode input streams based on combustion exhausts from gas turbines, as this can provide a mechanism for reducing NOx emissions. The conditions in the cathode can additionally or alternately be suitable for conversion of unburned hydrocarbons (in combination with $O_2$ in the cathode input stream) to typical combustion products, such as $CO_2$ and $H_2O$.

A suitable temperature for operation of an MCFC can be between about 450° C. and about 750° C., such as at least about 500° C., e.g., with an inlet temperature of about 550° C. and an outlet temperature of about 625° C. Prior to entering the cathode, heat can be added to or removed from the combustion exhaust, if desired, e.g., to provide heat for other processes, such as reforming the fuel input for the anode. For example, if the source for the cathode input stream is a combustion exhaust stream, the combustion exhaust stream may have a temperature greater than a desired temperature for the cathode inlet. In such an aspect, heat can be removed from the combustion exhaust prior to use as the cathode input stream. Alternatively, the combustion exhaust could be at very low temperature, for example after a wet gas scrubber on a coal-fired boiler, in which case the combustion exhaust can be below about 100° C. Alternatively, the combustion exhaust could be from the exhaust of a gas turbine operated in combined cycle mode, in which the gas can be cooled by raising steam to run a steam turbine for additional power generation. In this case, the gas can be below about 50° C. Heat can be added to a combustion exhaust that is cooler than desired.

Fuel Cell Arrangement

In various aspects, a configuration option for a fuel cell (such as a fuel cell array containing multiple fuel cell stacks) can be to divide the $CO_2$-containing stream between a plurality of fuel cells. Some types of sources for $CO_2$-containing streams can generate large volumetric flow rates relative to the capacity of an individual fuel cell. For example, the $CO_2$-containing output stream from an industrial combustion source can typically correspond to a large flow volume relative to desirable operating conditions for a single MCFC of reasonable size. Instead of processing the entire flow in a single MCFC, the flow can be divided amongst a plurality of MCFC units, usually at least some of which can be in parallel, so that the flow rate in each unit can be within a desired flow range.

A second configuration option can be to utilize fuel cells in series to successively remove $CO_2$ from a flow stream. Regardless of the number of initial fuel cells to which a $CO_2$-containing stream can be distributed to in parallel, each initial fuel cell can be followed by one or more additional cells in series to further remove additional $CO_2$. If the desired amount of $CO_2$ in the cathode output is sufficiently low, attempting to remove $CO_2$ from a cathode input stream down to the desired level in a single fuel cell or fuel cell stage could lead to a low and/or unpredictable voltage output for the fuel cell. Rather than attempting to remove $CO_2$ to the desired level in a single fuel cell or fuel cell stage, $CO_2$ can be removed in successive cells until a desired level can be achieved. For example, each cell in a series of fuel cells can be used to remove some percentage (e.g., about 50%) of the $CO_2$ present in a fuel stream. In such an example, if three fuel cells are used in series, the $CO_2$ concentration can be reduced (e.g., to about 15% or less of the original amount present, which can correspond to reducing the $CO_2$ concentration from about 6% to about 1% or less over the course of three fuel cells in series).

In another configuration, the operating conditions can be selected in early fuel stages in series to provide a desired output voltage while the array of stages can be selected to achieve a desired level of carbon separation. As an example, an array of fuel cells can be used with three fuel cells in series. The first two fuel cells in series can be used to remove $CO_2$ while maintaining a desired output voltage. The final fuel cell can then be operated to remove $CO_2$ to a desired concentration but at a lower voltage.

In still another configuration, there can be separate connectivity for the anodes and cathodes in a fuel cell array. For example, if the fuel cell array includes fuel cathodes connected in series, the corresponding anodes can be connected in any convenient manner, not necessarily matching up with the same arrangement as their corresponding cathodes, for example. This can include, for instance, connecting the anodes in parallel, so that each anode receives the same type of fuel feed, and/or connecting the anodes in a reverse series, so that the highest fuel concentration in the anodes can correspond to those cathodes having the lowest $CO_2$ concentration.

In yet another configuration, the amount of fuel delivered to one or more anode stages and/or the amount of $CO_2$ delivered to one or more cathode stages can be controlled in order to improve the performance of the fuel cell array. For example, a fuel cell array can have a plurality of cathode stages connected in series. In an array that includes three cathode stages in series, this can mean that the output from a first cathode stage can correspond to the input for a second cathode stage, and the output from the second cathode stage can correspond to the input for a third cathode stage. In this type of configuration, the $CO_2$ concentration can decrease with each successive cathode stage. To compensate for this reduced $CO_2$ concentration, additional hydrogen and/or methane can be delivered to the anode stages corresponding to the later cathode stages. The additional hydrogen and/or methane in the anodes corresponding to the later cathode stages can at least partially offset the loss of voltage and/or current caused by the reduced $CO_2$ concentration, which can increase the voltage and thus net power produced by the fuel cell. In another example, the cathodes in a fuel cell array can be connected partially in series and partially in parallel. In this type of example, instead of passing the entire combustion output into the cathodes in the first cathode stage, at least a portion of the combustion exhaust can be passed into a later cathode stage. This can provide an increased $CO_2$ content in a later cathode stage. Still other options for using variable feeds to either anode stages or cathode stages can be used if desired.

The cathode of a fuel cell can correspond to a plurality of cathodes from an array of fuel cells, as previously described. In some aspects, a fuel cell array can be operated to improve or maximize the amount of carbon transferred from the cathode to the anode. In such aspects, for the cathode output from the final cathode(s) in an array sequence (typically at least including a series arrangement, or else the final cathode(s) and the initial cathode(s) would be the same), the output composition can include about 2.0 vol % or less of $CO_2$ (e.g., about 1.5 vol % or less or about 1.2 vol % or less) and/or at least about 1.0 vol % of $CO_2$, such as at least about 1.2 vol % or at least about 1.5 vol %. Due to this limitation, the net efficiency of $CO_2$ removal when using molten carbonate fuel cells can be dependent on the amount of $CO_2$ in the cathode input. For cathode input streams with $CO_2$ contents of greater than about 6 vol %, such as at least about 8%, the limitation on the amount of $CO_2$ that can be removed is not severe. However, for a combustion reaction using natural gas as a fuel and with excess air, as is typically found in a gas turbine, the amount of $CO_2$ in the combustion exhaust may only correspond to a $CO_2$ concentration at the cathode input of less than about 5 vol %. Use of exhaust gas recycle can allow the amount of $CO_2$ at the cathode input to be increased to at least about 5 vol %, e.g., at least about 6 vol %. If EGR is increased when using natural gas as a fuel to produce a $CO_2$ concentration beyond about 6 vol %, then the flammability in the combustor can be decreased and the gas turbine may become unstable. However, when $H_2$ is added to the fuel, the flammability window can be significantly increased, allowing the amount of exhaust gas recycle to be increased further, so that concentrations of $CO_2$ at the cathode input of at least about 7.5 vol % or at least about 8 vol % can be achieved. As an example, based on a removal limit of about 1.5 vol % at the cathode exhaust, increasing the $CO_2$ content at the cathode input from about 5.5 vol % to about 7.5 vol % can correspond to a ~10% increase in the amount of $CO_2$ that can be captured using a fuel cell and transported to the anode loop for eventual $CO_2$ separation. The amount of $O_2$ in the cathode output can additionally or alternately be reduced, typically in an amount proportional to the amount of $CO_2$ removed, which can result in small corresponding increases in the amount(s) of the other (non-cathode-reactive) species at the cathode exit.

In other aspects, a fuel cell array can be operated to improve or maximize the energy output of the fuel cell, such as the total energy output, the electric energy output, the syngas chemical energy output, or a combination thereof. For example, molten carbonate fuel cells can be operated with an excess of reformable fuel in a variety of situations, such as for generation of a syngas stream for use in chemical synthesis plant and/or for generation of a high purity hydrogen stream. The syngas stream and/or hydrogen stream can be used as a syngas source, a hydrogen source, as a clean fuel source, and/or for any other convenient application. In such aspects, the amount of $CO_2$ in the cathode exhaust can be related to the amount of $CO_2$ in the cathode input stream and the $CO_2$ utilization at the desired operating conditions for improving or maximizing the fuel cell energy output.

Additionally or alternately, depending on the operating conditions, an MCFC can lower the $CO_2$ content of a cathode exhaust stream to about 5.0 vol % or less, e.g., about 4.0 vol % or less, or about 2.0 vol % or less, or about 1.5 vol % or less, or about 1.2 vol % or less. Additionally or alternately, the $CO_2$ content of the cathode exhaust stream can be at least about 0.9 vol %, such as at least about 1.0 vol %, or at least about 1.2 vol %, or at least about 1.5 vol %.

Molten Carbonate Fuel Cell Operation

In some aspects, a fuel cell may be operated in a single pass or once-through mode. In single pass mode, reformed products in the anode exhaust are not returned to the anode inlet. Thus, recycling syngas, hydrogen, or some other product from the anode output directly to the anode inlet is not done in single pass operation. More generally, in single pass operation, reformed products in the anode exhaust are also not returned indirectly to the anode inlet, such as by using reformed products to process a fuel stream subsequently introduced into the anode inlet. Optionally, $CO_2$ from the anode outlet can be recycled to the cathode inlet during operation of an MCFC in single pass mode. More generally, in some alternative aspects, recycling from the anode outlet to the cathode inlet may occur for an MCFC operating in single pass mode. Heat from the anode exhaust or output may additionally or alternately be recycled in a single pass mode. For example, the anode output flow may pass through a heat exchanger that cools the anode output and warms another stream, such as an input stream for the anode and/or the cathode. Recycling heat from anode to the fuel cell is consistent with use in single pass or once-through operation. Optionally but not preferably, constituents of the anode output may be burned to provide heat to the fuel cell during single pass mode.

Figure 3:
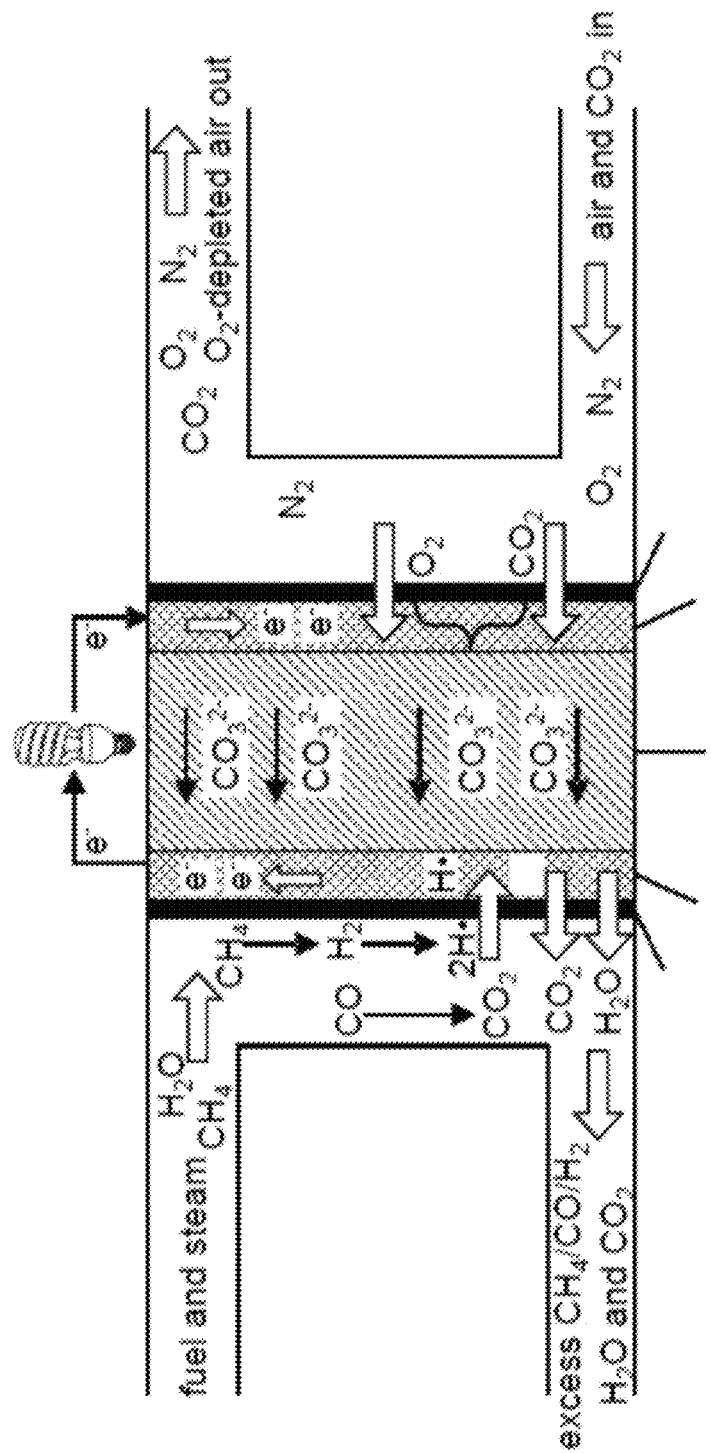
FIG. 3 schematically shows an example of the operation of a molten carbonate fuel cell.

FIG. 3 shows a schematic example of the operation of an MCFC for generation of electrical power. In FIG. 3, the anode portion of the fuel cell can receive fuel and steam ($H_2O$) as inputs, with outputs of water, $CO_2$, and optionally excess $H_2$, $CH_4$ (or other hydrocarbons), and/or CO. The cathode portion of the fuel cell can receive $CO_2$ and some oxidant (e.g., air/$O_2$) as inputs, with an output corresponding to a reduced amount of $CO_2$ in $O_2$-depleted oxidant (air). Within the fuel cell, $CO_3^{2-}$ ions formed in the cathode side can be transported across the electrolyte to provide the carbonate ions needed for the reactions occurring at the anode.

Several reactions can occur within a molten carbonate fuel cell such as the example fuel cell shown in FIG. 3. The reforming reactions can be optional, and can be reduced or eliminated if sufficient $H_2$ is provided directly to the anode. The following reactions are based on $CH_4$, but similar reactions can occur when other fuels are used in the fuel cell.

<anode reforming> $CH_4+H_2O=>3H_2+CO$ (1)

<water gas shift> $CO+H_2O=>H_2+CO_2$ (2)

<reforming and water gas shift combined> $CH_4+2H_2O=>4H_2+CO_2$ (3)

<anode $H_2$ oxidation> $H_2+CO_3^{2-}=>H_2O+CO_2+2e^-$ (4)

<cathode> $½O_2+CO_2+2e^-=>CO_3^{2-}$ (5)

Reaction (1) represents the basic hydrocarbon reforming reaction to generate $H_2$ for use in the anode of the fuel cell. The CO formed in reaction (1) can be converted to $H_2$ by the water-gas shift reaction (2). The combination of reactions (1) and (2) is shown as reaction (3). Reactions (1) and (2) can occur external to the fuel cell, and/or the reforming can be performed internal to the anode.

Reactions (4) and (5), at the anode and cathode respectively, represent the reactions that can result in electrical power generation within the fuel cell. Reaction (4) combines $H_2$, either present in the feed or optionally generated by reactions (1) and/or (2), with carbonate ions to form $H_2O$, $CO_2$, and electrons to the circuit. Reaction (5) combines $O_2$, $CO_2$, and electrons from the circuit to form carbonate ions. The carbonate ions generated by reaction (5) can be transported across the electrolyte of the fuel cell to provide the carbonate ions needed for reaction (4). In combination with the transport of carbonate ions across the electrolyte, a closed current loop can then be formed by providing an electrical connection between the anode and cathode.

In various embodiments, a goal of operating the fuel cell can be to improve the total efficiency of the fuel cell and/or the total efficiency of the fuel cell plus an integrated chemical synthesis process. This is typically in contrast to conventional operation of a fuel cell, where the goal can be to operate the fuel cell with high electrical efficiency for using the fuel provided to the cell for generation of electrical power. As defined above, total fuel cell efficiency may be determined by dividing the electric output of the fuel cell plus the lower heating value of the fuel cell outputs by the lower heating value of the input components for the fuel cell. In other words, TFCE=(LHV(el)+LHV(sg out))/LHV(in), where LHV(in) and LHV(sg out) refer to the LHV of the fuel components (such as $H_2$, $CH_4$, and/or CO) delivered to the fuel cell and syngas ($H_2$, CO and/or $CO_2$) in the anode outlet streams or flows, respectively. This can provide a measure of the electric energy plus chemical energy generated by the fuel cell and/or the integrated chemical process. It is noted that under this definition of total efficiency, heat energy used within the fuel cell and/or used within the integrated fuel cell/chemical synthesis system can contribute to total efficiency. However, any excess heat exchanged or otherwise withdrawn from the fuel cell or integrated fuel cell/chemical synthesis system is excluded from the definition. Thus, if excess heat from the fuel cell is used, for example, to generate steam for electricity generation by a steam turbine, such excess heat is excluded from the definition of total efficiency.

Several operational parameters may be manipulated to operate a fuel cell with excess reformable fuel. Some parameters can be similar to those currently recommended for fuel cell operation. In some aspects, the cathode conditions and temperature inputs to the fuel cell can be similar to those recommended in the literature. For example, the desired electrical efficiency and the desired total fuel cell efficiency may be achieved at a range of fuel cell operating temperatures typical for molten carbonate fuel cells. In typical operation, the temperature can increase across the fuel cell.

In other aspects, the operational parameters of the fuel cell can deviate from typical conditions so that the fuel cell is operated to allow a temperature decrease from the anode inlet to the anode outlet and/or from the cathode inlet to the cathode outlet. For example, the reforming reaction to convert a hydrocarbon into $H_2$ and CO is an endothermic reaction. If a sufficient amount of reforming is performed in a fuel cell anode relative to the amount of oxidation of hydrogen to generate electrical current, the net heat balance in the fuel cell can be endothermic. This can cause a temperature drop between the inlets and outlets of a fuel cell. During endothermic operation, the temperature drop in the fuel cell can be controlled so that the electrolyte in the fuel cell remains in a molten state.

Parameters that can be manipulated in a way so as to differ from those currently recommended can include the amount of fuel provided to the anode, the composition of the fuel provided to the anode, and/or the separation and capture of syngas in the anode output without significant recycling of syngas from the anode exhaust to either the anode input or the cathode input. In some aspects, no recycle of syngas or hydrogen from the anode exhaust to either the anode input or the cathode input can be allowed to occur, either directly or indirectly. In additional or alternative aspects, a limited amount of recycle can occur. In such aspects, the amount of recycle from the anode exhaust to the anode input and/or the cathode input can be less than about 10 vol % of the anode exhaust, such as less than about 5 vol %, or less than about 1 vol %.

Additionally or alternately, a goal of operating a fuel cell can be to separate $CO_2$ from the output stream of a combustion reaction or another process that produces a $CO_2$ output stream, in addition to allowing generation of electric power. In such aspects, the combustion reaction(s) can be used to power one or more generators or turbines, which can provide a majority of the power generated by the combined generator/fuel cell system. Rather than operating the fuel cell to optimize power generation by the fuel cell, the system can instead be operated to improve the capture of carbon dioxide from the combustion-powered generator while reducing or minimizing the number of fuels cells required for capturing the carbon dioxide. Selecting an appropriate configuration for the input and output flows of the fuel cell, as well as selecting appropriate operating conditions for the fuel cell, can allow for a desirable combination of total efficiency and carbon capture.

In some embodiments, the fuel cells in a fuel cell array can be arranged so that only a single stage of fuel cells (such as fuel cell stacks) can be present. In this type of embodiment, the anode fuel utilization for the single stage can represent the anode fuel utilization for the array. Another option can be that a fuel cell array can contain multiple stages of anodes and multiple stages of cathodes, with each anode stage having a fuel utilization within the same range, such as each anode stage having a fuel utilization within 10% of a specified value, for example within 5% of a specified value. Still another option can be that each anode stage can have a fuel utilization equal to a specified value or lower than the specified value by less than an amount, such as having each anode stage be not greater than a specified value by 10% or less, for example, by 5% or less. As an illustrative example, a fuel cell array with a plurality of anode stages can have each anode stage be within about 10% of 50% fuel utilization, which would correspond to each anode stage having a fuel utilization between about 40% and about 60%. As another example, a fuel cell array with a plurality of stages can have each anode stage be not greater than 60% anode fuel utilization with the maximum deviation being about 5% less, which would correspond to each anode stage having a fuel utilization between about 55% to about 60%. In still another example, one or more stages of fuel cells in a fuel cell array can be operated at a fuel utilization from about 30% to about 50%, such as operating a plurality of fuel cell stages in the array at a fuel utilization from about 30% to about 50%. More generally, any of the above types of ranges can be paired with any of the anode fuel utilization values specified herein.

Still another additional or alternate option can include specifying a fuel utilization for less than all of the anode stages. For example, in some aspects of the invention fuel cells/stacks can be arranged at least partially in one or more series arrangements such that anode fuel utilization can be specified for the first anode stage in a series, the second anode stage in a series, the final anode stage in a series, or any other convenient anode stage in a series. As used herein, the "first" stage in a series corresponds to the stage (or set of stages, if the arrangement contains parallel stages as well) to which input is directly fed from the fuel source(s), with later ("second," "third," "final," etc.) stages representing the stages to which the output from one or more previous stages is fed, instead of directly from the respective fuel source(s). In situations where both output from previous stages and input directly from the fuel source(s) are co-fed into a stage, there can be a "first" (set of) stage(s) and a "last" (set of) stage(s), but other stages ("second," "third," etc.) can be more tricky among which to establish an order (e.g., in such cases, ordinal order can be determined by concentration levels of one or more components in the composite input feed composition, such as $CO_2$ for instance, from highest concentration "first" to lowest concentration "last" with approximately similar compositional distinctions representing the same ordinal level.)

Yet another additional or alternate option can be to specify the anode fuel utilization corresponding to a particular cathode stage (again, where fuel cells/stacks can be arranged at least partially in one or more series arrangements). As noted above, based on the direction of the flows within the anodes and cathodes, the first cathode stage may not correspond to (be across the same fuel cell membrane from) the first anode stage. Thus, in some aspects of the invention, the anode fuel utilization can be specified for the first cathode stage in a series, the second cathode stage in a series, the final cathode stage in a series, or any other convenient cathode stage in a series.

Yet still another additional or alternate option can be to specify an overall average of fuel utilization over all fuel cells in a fuel cell array. In various aspects, the overall average of fuel utilization for a fuel cell array can be about 65% or less, for example, about 60% or less, about 55% or less, about 50% or less, or about 45% or less (additionally or alternately, the overall average fuel utilization for a fuel cell array can be at least about 25%, for example at least about 30%, at least about 35%, or at least about 40%). Such an average fuel utilization need not necessarily constrain the fuel utilization in any single stage, so long as the array of fuel cells meets the desired fuel utilization.

Applications for $CO_2$ Output after Capture

In various aspects of the invention, the systems and methods described above can allow for production of carbon dioxide as a pressurized fluid. For example, the $CO_2$ generated from a cryogenic separation stage can initially correspond to a pressurized $CO_2$ liquid with a purity of at least about 90%, e.g., at least about 95%, at least about 97%, at least about 98%, or at least about 99%. This pressurized $CO_2$ stream can be used, e.g., for injection into wells in order to further enhance oil or gas recovery such as in secondary oil recovery. When done in proximity to a facility that encompasses a gas turbine, the overall system may benefit from additional synergies in use of electrical/mechanical power and/or through heat integration with the overall system.

Alternatively, for systems dedicated to an enhanced oil recovery (EOR) application (i.e., not comingled in a pipeline system with tight compositional standards), the $CO_2$ separation requirements may be substantially relaxed. The EOR application can be sensitive to the presence of $O_2$, so $O_2$ can be absent, in some embodiments, from a $CO_2$ stream intended for use in EOR. However, the EOR application can tend to have a low sensitivity to dissolved CO, $H_2$, and/or $CH_4$. Also, pipelines that transport the $CO_2$ can be sensitive to these impurities. Those dissolved gases can typically have only subtle impacts on the solubilizing ability of $CO_2$ used for EOR. Injecting gases such as CO, $H_2$, and/or $CH_4$ as EOR gases can result in some loss of fuel value recovery, but such gases can be otherwise compatible with EOR applications.

Additionally or alternately, a potential use for $CO_2$ as a pressurized liquid can be as a nutrient in biological processes such as algae growth/harvesting. The use of MCFCs for $CO_2$ separation can ensure that most biologically significant pollutants could be reduced to acceptably low levels, resulting in a $CO_2$-containing stream having only minor amounts of other "contaminant" gases (such as CO, $H_2$, $N_2$, and the like, and combinations thereof) that are unlikely to substantially negatively affect the growth of photosynthetic organisms. This can be in stark contrast to the output streams generated by most industrial sources, which can often contain potentially highly toxic material such as heavy metals.

In this type of aspect of the invention, the $CO_2$ stream generated by separation of $CO_2$ in the anode loop can be used to produce biofuels and/or chemicals, as well as precursors thereof. Further additionally or alternately, $CO_2$ may be produced as a dense fluid, allowing for much easier pumping and transport across distances, e.g., to large fields of photosynthetic organisms. Conventional emission sources can emit hot gas containing modest amounts of $CO_2$ (e.g., about 4-15%) mixed with other gases and pollutants. These materials would normally need to be pumped as a dilute gas to an algae pond or biofuel "farm". By contrast, the MCFC system according to the invention can produce a concentrated $CO_2$ stream (~60-70% by volume on a dry basis) that can be concentrated further to 95%+(for example 96%+, 97%+, 98%+, or 99%+) and easily liquefied. This stream can then be transported easily and efficiently over long distances at relatively low cost and effectively distributed over a wide area. In these embodiments, residual heat from the combustion source/MCFC may be integrated into the overall system as well.

An alternative embodiment may apply where the $CO_2$ source/MCFC and biological/chemical production sites are co-located. In that case, only minimal compression may be necessary (i.e., to provide enough $CO_2$ pressure to use in the biological production, e.g., from about 15 psig to about 150 psig). Several novel arrangements can be possible in such a case. Secondary reforming may optionally be applied to the anode exhaust to reduce $CH_4$ content, and water-gas shift may optionally additionally or alternately be present to drive any remaining CO into $CO_2$ and $H_2$.

The components from an anode output stream and/or cathode output stream can be used for a variety of purposes. One option can be to use the anode output as a source of hydrogen, as described above. For an MCFC integrated with or co-located with a refinery, the hydrogen can be used as a hydrogen source for various refinery processes, such as hydroprocessing. Another option can be to additionally or alternately use hydrogen as a fuel source where the $CO_2$ from combustion has already been "captured." Such hydrogen can be used in a refinery or other industrial setting as a fuel for a boiler, furnace, and/or fired heater, and/or the hydrogen can be used as a feed for an electric power generator, such as a turbine. Hydrogen from an MCFC fuel cell can further additionally or alternatively be used as an input stream for other types of fuel cells that require hydrogen as an input, possibly including vehicles powered by fuel cells. Still another option can be to additionally or alternately use syngas generated as an output from an MCFC fuel cell as a fermentation input.

Another option can be to additionally or alternately use syngas generated from the anode output. Of course, syngas can be used as a fuel, although a syngas based fuel can still lead to some $CO_2$ production when burned as fuel. In other aspects, a syngas output stream can be used as an input for a chemical synthesis process. One option can be to additionally or alternately use syngas for a Fischer-Tropsch type process, and/or another process where larger hydrocarbon molecules are formed from the syngas input. Another option can be to additionally or alternately use syngas to form an intermediate product such as methanol. Methanol could be used as the final product, but in other aspects methanol generated from syngas can be used to generate larger compounds, such as gasoline, olefins, aromatics, and/or other products. It is noted that a small amount of $CO_2$ can be acceptable in the syngas feed to a methanol synthesis process, and/or to a Fischer-Tropsch process utilizing a shifting catalyst. Hydroformylation is an additional or alternate example of still another synthesis process that can make use of a syngas input.

It is noted that one variation on use of an MCFC to generate syngas can be to use MCFC fuel cells as part of a system for processing methane and/or natural gas withdrawn by an offshore oil platform or other production system that is a considerable distance from its ultimate market. Instead of attempting to transport the gas phase output from a well, or attempting to store the gas phase product for an extended period, the gas phase output from a well can be used as the input to an MCFC fuel cell array. This can lead to a variety of benefits. First, the electric power generated by the fuel cell array can be used as a power source for the platform. Additionally, the syngas output from the fuel cell array can be used as an input for a Fischer-Tropsch process at the production site. This can allow for formation of liquid hydrocarbon products more easily transported by pipeline, ship, or railcar from the production site to, for example, an on-shore facility or a larger terminal Still other integration options can additionally or alternately include using the cathode output as a source of higher purity, heated nitrogen. The cathode input can often include a large portion of air, which means a substantial portion of nitrogen can be included in the cathode input. The fuel cell can transport $CO_2$ and $O_2$ from the cathode across the electrolyte to the anode, and the cathode outlet can have lower concentrations of $CO_2$ and $O_2$, and thus a higher concentration of $N_2$ than found in air. With subsequent removal of the residual $O_2$ and $CO_2$, this nitrogen output can be used as an input for production of ammonia or other nitrogen-containing chemicals, such as urea, ammonium nitrate, and/or nitric acid. It is noted that urea synthesis could additionally or alternately use $CO_2$ separate from the anode output as an input feed.

Integration Example: Applications for Integration with Combustion Turbines

In some aspects of the invention, a combustion source for generating power and exhausting a $CO_2$-containing exhaust can be integrated with the operation of molten carbonate fuel cells. An example of a suitable combustion source is a gas turbine. Preferably, the gas turbine can combust natural gas, methane gas, or another hydrocarbon gas in a combined cycle mode integrated with steam generation and heat recovery for additional efficiency. Modern natural gas combined cycle efficiencies are about 60% for the largest and newest designs. The resulting $CO_2$-containing exhaust gas stream can be produced at an elevated temperature compatible with the MCFC operation, such as 300° C. ~700° C. and preferably 500° C. ~650° C. The gas source can optionally but preferably be cleaned of contaminants such as sulfur that can poison the MCFC before entering the turbine. Alternatively, the gas source can be a coal-fired generator, wherein the exhaust gas would typically be cleaned post-combustion due to the greater level of contaminants in the exhaust gas. In such an alternative, some heat exchange to/from the gas may be necessary to enable clean-up at lower temperatures. In additional or alternate embodiments, the source of the $CO_2$-containing exhaust gas can be the output from a boiler, combustor, or other heat source that burns carbon-rich fuels. In other additional or alternate embodiments, the source of the $CO_2$-containing exhaust gas can be bio-produced $CO_2$ in combination with other sources.

For integration with a combustion source, some alternative configurations for processing of a fuel cell anode can be desirable. For example, an alternative configuration can be to recycle at least a portion of the exhaust from a fuel cell anode to the input of a fuel cell anode. The output stream from an MCFC anode can include $H_2O$, $CO_2$, optionally CO, and optionally but typically unreacted fuel (such as $H_2$ or $CH_4$) as the primary output components. Instead of using this output stream as an external fuel stream and/or an input stream for integration with another process, one or more separations can be performed on the anode output stream in order to separate the $CO_2$ from the components with potential fuel value, such as $H_2$ or CO. The components with fuel value can then be recycled to the input of an anode.

This type of configuration can provide one or more benefits. First, $CO_2$ can be separated from the anode output, such as by using a cryogenic $CO_2$ separator. Several of the components of the anode output ($H_2$, CO, $CH_4$) are not easily condensable components, while $CO_2$ and $H_2O$ can be separated individually as condensed phases. Depending on the embodiment, at least about 90 vol % of the $CO_2$ in the anode output can be separated to form a relatively high purity $CO_2$ output stream. Alternatively, in some aspects less $CO_2$ can be removed from the anode output, so that about 50 vol % to about 90 vol % of the $CO_2$ in the anode output can be separated out, such as about 80 vol % or less or about 70 vol % or less. After separation, the remaining portion of the anode output can correspond primarily to components with fuel value, as well as reduced amounts of $CO_2$ and/or $H_2O$. This portion of the anode output after separation can be recycled for use as part of the anode input, along with additional fuel. In this type of configuration, even though the fuel utilization in a single pass through the MCFC(s) may be low, the unused fuel can be advantageously recycled for another pass through the anode. As a result, the single-pass fuel utilization can be at a reduced level, while avoiding loss (exhaust) of unburned fuel to the environment.

Additionally or alternatively to recycling a portion of the anode exhaust to the anode input, another configuration option can be to use a portion of the anode exhaust as an input for a combustion reaction for a turbine or other combustion device, such as a boiler, furnace, and/or fired heater. The relative amounts of anode exhaust recycled to the anode input and/or as an input to the combustion device can be any convenient or desirable amount. If the anode exhaust is recycled to only one of the anode input and the combustion device, the amount of recycle can be any convenient amount, such as up to 100% of the portion of the anode exhaust remaining after any separation to remove $CO_2$ and/or $H_2O$. When a portion of the anode exhaust is recycled to both the anode input and the combustion device, the total recycled amount by definition can be 100% or less of the remaining portion of anode exhaust. Otherwise, any convenient split of the anode exhaust can be used. In various embodiments of the invention, the amount of recycle to the anode input can be at least about 10% of the anode exhaust remaining after separations, for example at least about 25%, at least about 40%, at least about 50%, at least about 60%, at least about 75%, or at least about 90%. Additionally or alternately in those embodiments, the amount of recycle to the anode input can be about 90% or less of the anode exhaust remaining after separations, for example about 75% or less, about 60% or less, about 50% or less, about 40% or less, about 25% or less, or about 10% or less. Further additionally or alternatively, in various embodiments of the invention, the amount of recycle to the combustion device can be at least about 10% of the anode exhaust remaining after separations, for example at least about 25%, at least about 40%, at least about 50%, at least about 60%, at least about 75%, or at least about 90%. Additionally or alternately in those embodiments, the amount of recycle to the combustion device can be about 90% or less of the anode exhaust remaining after separations, for example about 75% or less, about 60% or less, about 50% or less, about 40% or less, about 25% or less, or about 10% or less.

In still other alternative aspects of the invention, the fuel for a combustion device can additionally or alternately be a fuel with an elevated quantity of components that are inert and/or otherwise act as a diluent in the fuel. $CO_2$ and $N_2$ are examples of components in a natural gas feed that can be relatively inert during a combustion reaction. When the amount of inert components in a fuel feed reaches a sufficient level, the performance of a turbine or other combustion source can be impacted. The impact can be due in part to the ability of the inert components to absorb heat, which can tend to quench the combustion reaction. Examples of fuel feeds with a sufficient level of inert components can include fuel feeds containing at least about 20 vol % $CO_2$, or fuel feeds containing at least about 40 vol % $N_2$, or fuel feeds containing combinations of $CO_2$ and $N_2$ that have sufficient inert heat capacity to provide similar quenching ability. (It is noted that $CO_2$ has a greater heat capacity than $N_2$, and therefore lower concentrations of $CO_2$ can have a similar impact as higher concentrations of $N_2$. $CO_2$ can also participate in the combustion reactions more readily than $N_2$, and in doing so remove $H_2$ from the combustion. This consumption of $H_2$ can have a large impact on the combustion of the fuel, by reducing the flame speed and narrowing the flammability range of the air and fuel mixture.) More generally, for a fuel feed containing inert components that impact the flammability of the fuel feed, the inert components in the fuel feed can be at least about 20 vol %, such as at least about 40 vol %, or at least about 50 vol %, or at least about 60 vol %. Preferably, the amount of inert components in the fuel feed can be about 80 vol % or less.

When a sufficient amount of inert components are present in a fuel feed, the resulting fuel feed can be outside of the flammability window for the fuel components of the feed. In this type of situation, addition of $H_2$ from a recycled portion of the anode exhaust to the combustion zone for the generator can expand the flammability window for the combination of fuel feed and $H_2$, which can allow, for example, a fuel feed containing at least about 20 vol % $CO_2$ or at least about 40% $N_2$ (or other combinations of $CO_2$ and $N_2$) to be successfully combusted.

Relative to a total volume of fuel feed and $H_2$ delivered to a combustion zone, the amount of $H_2$ for expanding the flammability window can be at least about 5 vol % of the total volume of fuel feed plus $H_2$, such as at least about 10 vol %, and/or about 25 vol % or less. Another option for characterizing the amount of $H_2$ to add to expand the flammability window can be based on the amount of fuel components present in the fuel feed before $H_2$ addition. Fuel components can correspond to methane, natural gas, other hydrocarbons, and/or other components conventionally viewed as fuel for a combustion-powered turbine or other generator. The amount of $H_2$ added to the fuel feed can correspond to at least about one third of the volume of fuel components (1:3 ratio of $H_2$:fuel component) in the fuel feed, such as at least about half of the volume of the fuel components (1:2 ratio). Additionally or alternately, the amount of $H_2$ added to the fuel feed can be roughly equal to the volume of fuel components in the fuel feed (1:1 ratio) or less. For example, for a feed containing about 30 vol % $CH_4$, about 10% $N_2$, and about 60% $CO_2$, a sufficient amount of anode exhaust can be added to the fuel feed to achieve about a 1:2 ratio of $H_2$ to $CH_4$. For an idealized anode exhaust that contained only $H_2$, addition of $H_2$ to achieve a 1:2 ratio would result in a feed containing about 26 vol % $CH_4$, 13 vol % $H_2$, 9 vol % $N_2$, and 52 vol % $CO_2$.

Exhaust Gas Recycle

Aside from providing exhaust gas to a fuel cell array for capture and eventual separation of the $CO_2$, an additional or alternate potential use for exhaust gas can include recycle back to the combustion reaction to increase the $CO_2$ content. When hydrogen is available for addition to the combustion reaction, such as hydrogen from the anode exhaust of the fuel cell array, further benefits can be gained from using recycled exhaust gas to increase the $CO_2$ content within the combustion reaction.

In various aspects of the invention, the exhaust gas recycle loop of a power generation system can receive a first portion of the exhaust gas from combustion, while the fuel cell array can receive a second portion. The amount of exhaust gas from combustion recycled to the combustion zone of the power generation system can be any convenient amount, such as at least about 15% (by volume), for example at least about 25%, at least about 35%, at least about 45%, or at least about 50%. Additionally or alternatively, the amount of combustion exhaust gas recirculated to the combustion zone can be about 65% (by volume) or less, e.g., about 60% or less, about 55% or less, about 50% or less, or about 45% or less.

In one or more aspects of the invention, a mixture of an oxidant (such as air and/or oxygen-enriched air) and fuel can be combusted and (simultaneously) mixed with a stream of recycled exhaust gas. The stream of recycled exhaust gas, which can generally include products of combustion such as $CO_2$, can be used as a diluent to control, adjust, or otherwise moderate the temperature of combustion and of the exhaust that can enter the succeeding expander. As a result of using oxygen-enriched air, the recycled exhaust gas can have an increased $CO_2$ content, thereby allowing the expander to operate at even higher expansion ratios for the same inlet and discharge temperatures, thereby enabling significantly increased power production.

A gas turbine system can represent one example of a power generation system where recycled exhaust gas can be used to enhance the performance of the system. The gas turbine system can have a first/main compressor coupled to an expander via a shaft. The shaft can be any mechanical, electrical, or other power coupling, thereby allowing a portion of the mechanical energy generated by the expander to drive the main compressor. The gas turbine system can also include a combustion chamber configured to combust a mixture of a fuel and an oxidant. In various aspects of the invention, the fuel can include any suitable hydrocarbon gas/liquid, such as syngas, natural gas, methane, ethane, propane, butane, naphtha diesel, kerosene, aviation fuel, coal derived fuel, bio-fuel, oxygenated hydrocarbon feedstock, or any combinations thereof. The oxidant can, in some embodiments, be derived from a second or inlet compressor fluidly coupled to the combustion chamber and adapted to compress a feed oxidant. In one or more embodiments of the invention, the feed oxidant can include atmospheric air and/or enriched air. When the oxidant includes enriched air alone or a mixture of atmospheric air and enriched air, the enriched air can be compressed by the inlet compressor (in the mixture, either before or after being mixed with the atmospheric air). The enriched air and/or the air-enriched air mixture can have an overall oxygen concentration of at least about 25 volume %, e.g., at least about 30 volume %, at least about 35 volume %, at least about 40 volume %, at least about 45 volume %, or at least about 50 volume %. Additionally or alternately, the enriched air and/or the air-enriched air mixture can have an overall oxygen concentration of about 80 volume % or less, such as about 70 volume % or less.

The enriched air can be derived from any one or more of several sources. For example, the enriched air can be derived from such separation technologies as membrane separation, pressure swing adsorption, temperature swing adsorption, nitrogen plant-byproduct streams, and/or combinations thereof. The enriched air can additionally or alternatively be derived from an air separation unit (ASU), such as a cryogenic ASU, for producing nitrogen for pressure maintenance or other purposes. In certain embodiments of the invention, the reject stream from such an ASU can be rich in oxygen, having an overall oxygen content from about 50 volume % to about 70 volume %, can be used as at least a portion of the enriched air and subsequently diluted, if needed, with unprocessed atmospheric air to obtain the desired oxygen concentration.

In addition to the fuel and oxidant, the combustion chamber can optionally also receive a compressed recycle exhaust gas, such as an exhaust gas recirculation primarily having $CO_2$ and nitrogen components. The compressed recycle exhaust gas can be derived from the main compressor, for instance, and adapted to help facilitate combustion of the oxidant and fuel, e.g., by moderating the temperature of the combustion products. As can be appreciated, recirculating the exhaust gas can serve to increase $CO_2$ concentration.

An exhaust gas directed to the inlet of the expander can be generated as a product of combustion reaction. The exhaust gas can have a heightened $CO_2$ content based, at least in part, on the introduction of recycled exhaust gas into the combustion reaction. As the exhaust gas expands through the expander, it can generate mechanical power to drive the main compressor, to drive an electrical generator, and/or to power other facilities.

The power generation system can, in many embodiments, also include an exhaust gas recirculation (EGR) system. In one or more aspects of the invention, the EGR system can include a heat recovery steam generator (HRSG) and/or another similar device fluidly coupled to a steam gas turbine. In at least one embodiment, the combination of the HRSG and the steam gas turbine can be characterized as a power-producing closed Rankine cycle. In combination with the gas turbine system, the HRSG and the steam gas turbine can form part of a combined-cycle power generating plant, such as a natural gas combined-cycle (NGCC) plant. The gaseous exhaust can be introduced to the HRSG in order to generate steam and a cooled exhaust gas. The HRSG can include various units for separating and/or condensing water out of the exhaust stream, transferring heat to form steam, and/or modifying the pressure of streams to a desired level. In certain embodiments, the steam can be sent to the steam gas turbine to generate additional electrical power.

After passing through the HRSG and optional removal of at least some $H_2O$, the $CO_2$-containing exhaust stream can, in some embodiments, be recycled for use as an input to the combustion reaction. As noted above, the exhaust stream can be compressed (or decompressed) to match the desired reaction pressure within the vessel for the combustion reaction.

Example of Integrated System

Figure 4:
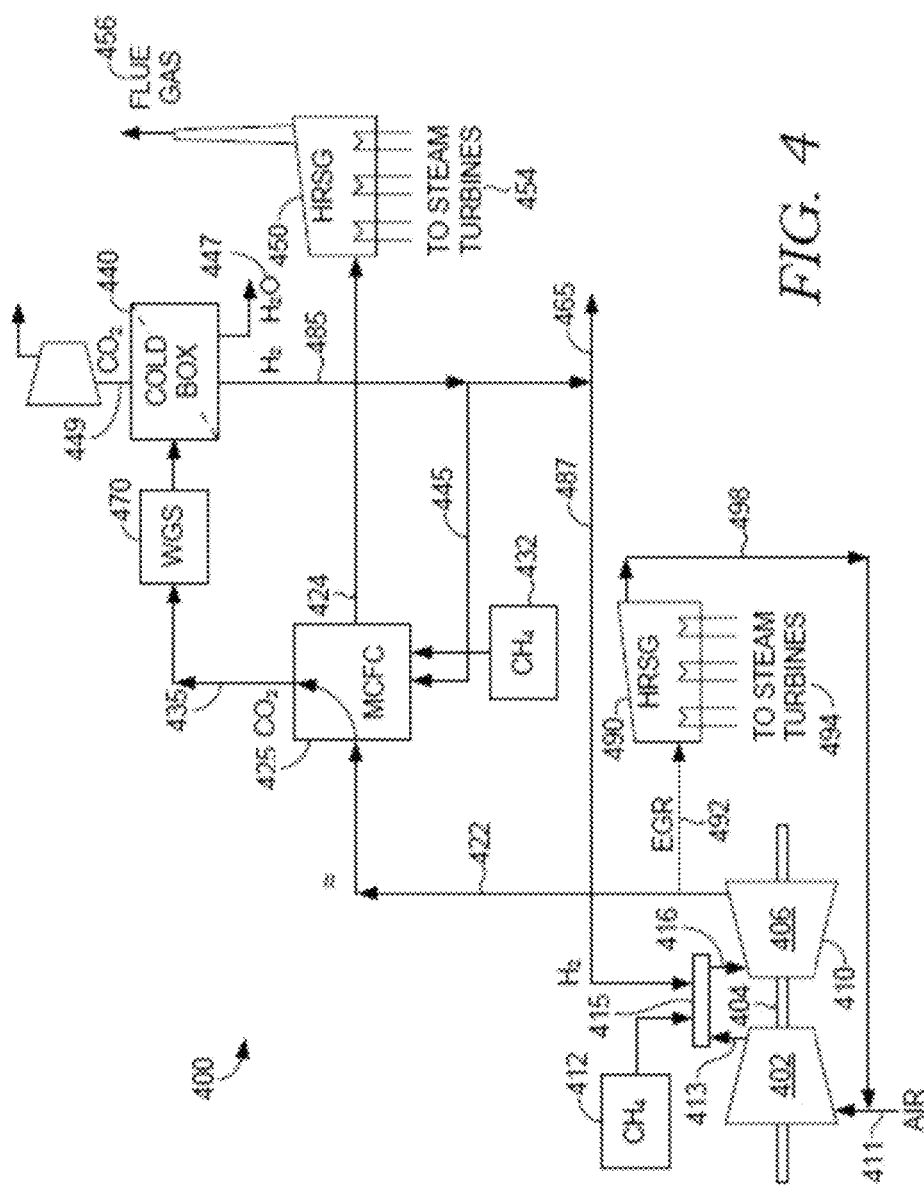
FIG. 4 schematically shows an example of a combined cycle system for generating electricity based on combustion of a carbon-based fuel.

FIG. 4 schematically shows an example of an integrated system including introduction of both $CO_2$-containing recycled exhaust gas and $H_2$ or CO from the fuel cell anode exhaust into the combustion reaction for powering a turbine. In FIG. 4, the turbine can include a compressor 402, a shaft 404, an expander 406, and a combustion zone 415. An oxygen source 411 (such as air and/or oxygen-enriched air) can be combined with recycled exhaust gas 498 and compressed in compressor 402 prior to entering combustion zone 415. A fuel 412, such as $CH_4$, and optionally a stream containing $H_2$ or CO 187 can be delivered to the combustion zone. The fuel and oxidant can be reacted in zone 415 and optionally but preferably passed through expander 406 to generate electric power. The exhaust gas from expander 106 can be used to form two streams, e.g., a $CO_2$-containing stream 422 (that can be used as an input feed for fuel cell array 425) and another $CO_2$-containing stream 492 (that can be used as the input for a heat recovery and steam generator system 490, which can, for example, enable additional electricity to be generated using steam turbines 494). After passing through heat recovery system 490, including optional removal of a portion of $H_2O$ from the $CO_2$-containing stream, the output stream 498 can be recycled for compression in compressor 402 or a second compressor that is not shown. The proportion of the exhaust from expander 406 used for $CO_2$-containing stream 492 can be determined based on the desired amount of $CO_2$ for addition to combustion zone 415.

As used herein, the EGR ratio is the flow rate for the fuel cell bound portion of the exhaust gas divided by the combined flow rate for the fuel cell bound portion and the recovery bound portion, which is sent to the heat recovery generator. For example, the EGR ratio for flows shown in FIG. 4 is the flow rate of stream 422 divided by the combined flow rate of streams 422 and 492.

The $CO_2$-containing stream 422 can be passed into a cathode portion (not shown) of a molten carbonate fuel cell array 425. Based on the reactions within fuel cell array 425, $CO_2$ can be separated from stream 422 and transported to the anode portion (not shown) of the fuel cell array 425. This can result in a cathode output stream 424 depleted in $CO_2$. The cathode output stream 424 can then be passed into a heat recovery (and optional steam generator) system 450 for generation of heat exchange and/or additional generation of electricity using steam turbines 454 (which may optionally be the same as the aforementioned steam turbines 494). After passing through heat recovery and steam generator system 450, the resulting flue gas stream 456 can be exhausted to the environment and/or passed through another type of carbon capture technology, such as an amine scrubber.

After transport of $CO_2$ from the cathode side to the anode side of fuel cell array 425, the anode output 435 can optionally be passed into a water gas shift reactor 470. Water gas shift reactor 470 can be used to generate additional $H_2$ and $CO_2$ at the expense of CO (and $H_2O$) present in the anode output 435. The output from the optional water gas shift reactor 470 can then be passed into one or more separation stages 440, such as a cold box or a cryogenic separator. This can allow for separation of an $H_2O$ stream 447 and $CO_2$ stream 449 from the remaining portion of the anode output. The remaining portion of the anode output 485 can include unreacted $H_2$ generated by reforming but not consumed in fuel cell array 425. A first portion 445 of the $H_2$-containing stream 485 can be recycled to the input for the anode(s) in fuel cell array 425. A second portion 487 of stream 485 can be used as an input for combustion zone 415. A third portion 465 can be used as is for another purpose and/or treated for subsequent further use. Although FIG. 4 and the description herein schematically details up to three portions, it is contemplated that only one of these three portions can be exploited, only two can be exploited, or all three can be exploited according to the invention.

Figure 5:
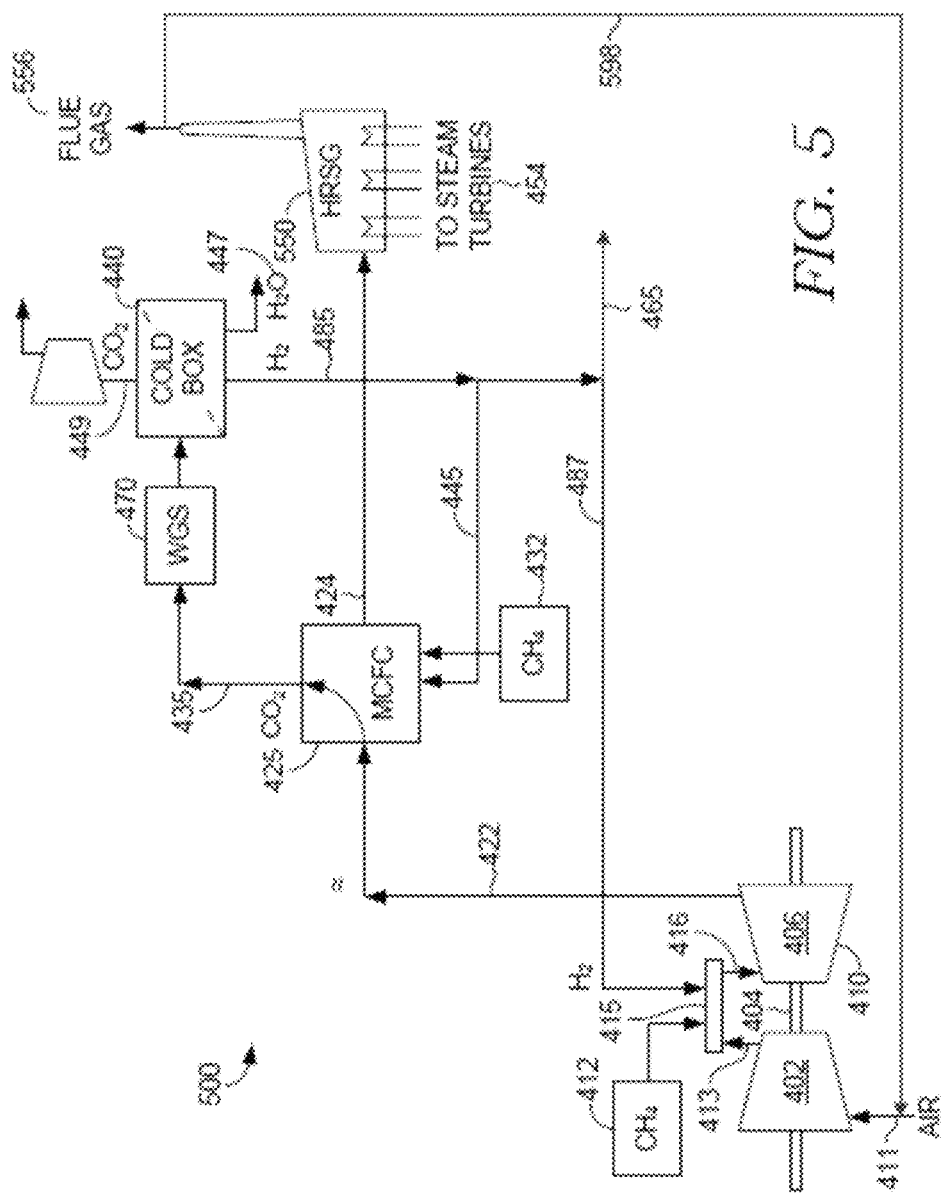
FIG. 5 schematically shows an example of a combined cycle system for generating electricity based on combustion of a carbon-based fuel.
Figure 6:
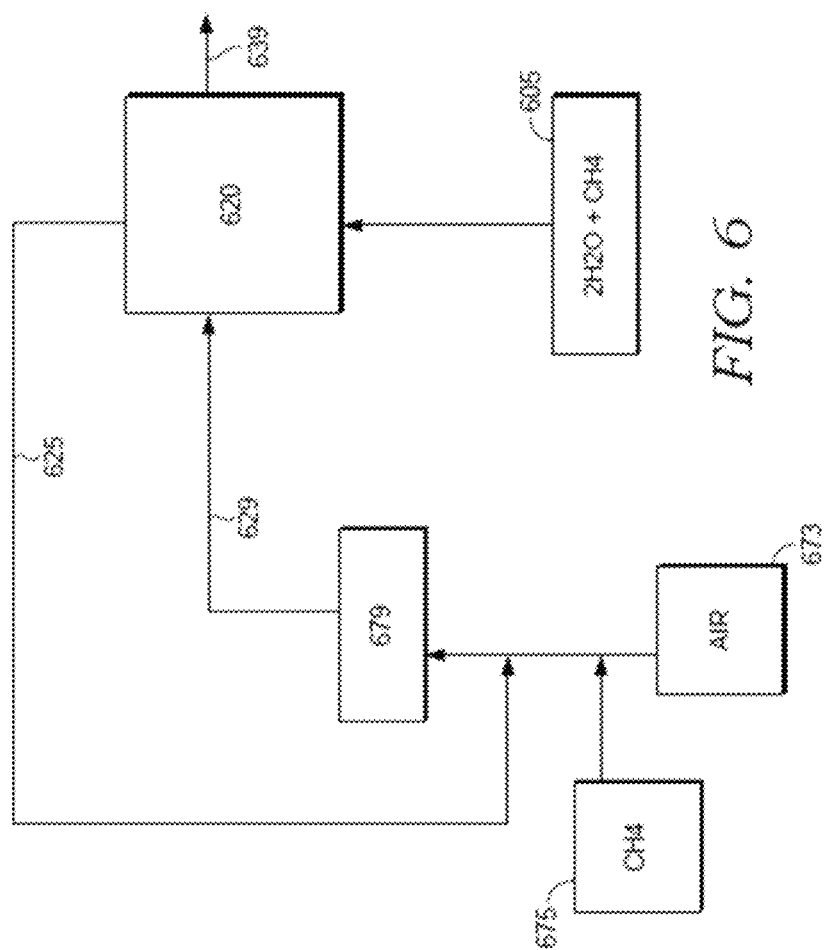
FIG. 6 schematically shows an example of a balanced configuration for operating a molten carbonate fuel cell.

In FIG. 4, the exhaust for the exhaust gas recycle loop is provided by a first heat recovery and steam generator system 490, while a second heat recovery and steam generator system 450 can be used to capture excess heat from the cathode output of the fuel cell array 425. FIG. 5 shows an alternative embodiment where the exhaust gas recycle loop is provided by the same heat recovery steam generator used for processing the fuel cell array output. In FIG. 5, recycled exhaust gas 598 is provided by heat recovery and steam generator system 550 as a portion of the flue gas stream 556. This can eliminate the separate heat recovery and steam generator system associated with the turbine.

In various embodiments of the invention, the process can be approached as starting with a combustion reaction for powering a turbine, an internal combustion engine, or another system where heat and/or pressure generated by a combustion reaction can be converted into another form of power. The fuel for the combustion reaction can comprise or be hydrogen, a hydrocarbon, and/or any other compound containing carbon that can be oxidized (combusted) to release energy. Except for when the fuel contains only hydrogen, the composition of the exhaust gas from the combustion reaction can have a range of $CO_2$ contents, depending on the nature of the reaction (e.g., from at least about 2 vol % to about 25 vol % or less). Thus, in certain embodiments where the fuel is carbonaceous, the $CO_2$ content of the exhaust gas can be at least about 2 vol %, for example at least about 4 vol %, at least about 5 vol %, at least about 6 vol %, at least about 8 vol %, or at least about 10 vol %. Additionally or alternately in such carbonaceous fuel embodiments, the $CO_2$ content can be about 25 vol % or less, for example about 20 vol % or less, about 15 vol % or less, about 10 vol % or less, about 7 vol % or less, or about 5 vol % or less. Exhaust gases with lower relative $CO_2$ contents (for carbonaceous fuels) can correspond to exhaust gases from combustion reactions on fuels such as natural gas with lean (excess air) combustion. Higher relative $CO_2$ content exhaust gases (for carbonaceous fuels) can correspond to optimized natural gas combustion reactions, such as those with exhaust gas recycle, and/or combustion of fuels such as coal.

In some aspects of the invention, the fuel for the combustion reaction can contain at least about 90 volume % of compounds containing five carbons or less, e.g., at least about 95 volume %. In such aspects, the $CO_2$ content of the exhaust gas can be at least about 4 vol %, for example at least about 5 vol %, at least about 6 vol %, at least about 7 vol %, or at least about 7.5 vol %. Additionally or alternately, the $CO_2$ content of the exhaust gas can be about 13 vol % or less, e.g., about 12 vol % or less, about 10 vol % or less, about 9 vol % or less, about 8 vol % or less, about 7 vol % or less, or about 6 vol % or less. The $CO_2$ content of the exhaust gas can represent a range of values depending on the configuration of the combustion-powered generator. Recycle of an exhaust gas can be beneficial for achieving a $CO_2$ content of at least about 6 vol %, while addition of hydrogen to the combustion reaction can allow for further increases in $CO_2$ content to achieve a $CO_2$ content of at least about 7.5 vol %.

Alternative Configuration—High Severity NOx Turbine

Gas turbines can be limited in their operation by several factors. One typical limitation can be that the maximum temperature in the combustion zone can be controlled below certain limits to achieve sufficiently low concentrations of nitrogen oxides (NOx) in order to satisfy regulatory emission limits. Regulatory emission limits can require a combustion exhaust to have a NOx content of about 20 vppm or less, and possible 10 vppm or less, when the combustion exhaust is allowed to exit to the environment.

NOx formation in natural gas-fired combustion turbines can be a function of temperature and residence time. Reactions that result in formation of NOx can be of reduced and/or minimal importance below a flame temperature of about 1500° F., but NOx production can increase rapidly as the temperature increases beyond this point. In a gas turbine, initial combustion products can be mixed with extra air to cool the mixture to a temperature around 1200° F., and temperature can be limited by the metallurgy of the expander blades. Early gas turbines typically executed the combustion in diffusion flames that had stoichiometric zones with temperatures well above 1500° F., resulting in higher NOx concentrations. More recently, the current generation of 'Dry Low Nox' (DLN) burners can use special pre-mixed burners to burn natural gas at cooler lean (less fuel than stoichiometric) conditions. For example, more of the dilution air can be mixed in to the initial flame, and less can be mixed in later to bring the temperature down to the ~1200° F. turbine-expander inlet temperature. The disadvantages for DLN burners can include poor performance at turndown, higher maintenance, narrow ranges of operation, and poor fuel flexibility. The latter can be a concern, as DLN burners can be more difficult to apply to fuels of varying quality (or difficult to apply at all to liquid fuels). For low BTU fuels, such as fuels containing a high content of $CO_2$, DLN burners are typically not used and instead diffusion burners can be used. In addition, gas turbine efficiency can be increased by using a higher turbine-expander inlet temperature. However, because there can be a limited amount of dilution air, and this amount can decrease with increased turbine-expander inlet temperature, the DLN burner can become less effective at maintaining low NOx as the efficiency of the gas turbine improves.

In various aspects of the invention, a system integrating a gas turbine with a fuel cell for carbon capture can allow use of higher combustion zone temperatures while reducing and/or minimizing additional NOx emissions, as well as enabling DLN-like NOx savings via use of turbine fuels that are not presently compatible with DLN burners. In such aspects, the turbine can be run at higher power (i.e., higher temperature) resulting in higher NOx emissions, but also higher power output and potentially higher efficiency. In some aspects of the invention, the amount of NOx in the combustion exhaust can be at least about 20 vppm, such as at least about 30 vppm, or at least about 40 vppm. Additionally or alternately, the amount of NOx in the combustion exhaust can be about 1000 vppm or less, such as about 500 vppm or less, or about 250 vppm or less, or about 150 vppm or less, or about 100 vppm or less. In order to reduce the NOx levels to levels required by regulation, the resulting NOx can be equilibrated via thermal NOx destruction (reduction of NOx levels to equilibrium levels in the exhaust stream) through one of several mechanisms, such as simple thermal destruction in the gas phase; catalyzed destruction from the nickel cathode catalyst in the fuel cell array; and/or assisted thermal destruction prior to the fuel cell by injection of small amounts of ammonia, urea, or other reductant. This can be assisted by introduction of hydrogen derived from the anode exhaust. Further reduction of NOx in the cathode of the fuel cell can be achieved via electrochemical destruction wherein the NOx can react at the cathode surface and can be destroyed. This can result in some nitrogen transport across the membrane electrolyte to the anode, where it may form ammonia or other reduced nitrogen compounds. With respect to NOx reduction methods involving an MCFC, the expected NOx reduction from a fuel cell/fuel cell array can be about 80% or less of the NOx in the input to the fuel cell cathode, such as about 70% or less, and/or at least about 5%. It is noted that sulfidic corrosion can also limit temperatures and affect turbine blade metallurgy in conventional systems. However, the sulfur restrictions of the MCFC system can typically require reduced fuel sulfur levels that reduce or minimize concerns related to sulfidic corrosion. Operating the MCFC array at low fuel utilization can further mitigate such concerns, such as in aspects where a portion of the fuel for the combustion reaction corresponds to hydrogen from the anode exhaust.

Operating the Fuel Cell at Low Voltage

The conventional fuel cell practice teaches that molten carbonate and solid oxide fuel cells should be operated to maximize power density. The ability to maximize power density can be limited by a need to satisfy other operating constraints, such as temperature differential across the fuel cell. Generally, fuel cell parameters are selected to optimize power density as much as is feasible given other constraints. As an example, FIG. 6-13 of the NETL Fuel Cell Handbook and the discussion surrounding FIG. 6-13 teach that operation of a fuel cell at low fuel utilization is hindered by the decrease in fuel conversion that occurs as the fuel utilization is decreased. Generally, a higher operating voltage $V_A$ is desired to increase power density.

An aspect of the invention can be to operate the fuel cell at low fuel utilization, and to overcome the problem of decreased $CH_4$ conversion by decreasing the voltage. The decreased voltage can increase the amount of heat available for use in the conversion reactions. In various aspects, the fuel cell can be operated at a voltage $V_A$ of less than about 0.7 Volts, for example less than about 0.68 V, less than about 0.67 V, less than about 0.66 V, or about 0.65 V or less. Additionally or alternatively, the fuel cell can be operated at a voltage $V_A$ of at least about 0.60, for example at least about 0.61, at least about 0.62, or at least about 0.63. In so doing, energy that would otherwise leave the fuel cell as electrical energy at high voltage can remain within the cell as heat as the voltage is lowered. This additional heat can allow for increased endothermic reactions to occur, for example increasing the $CH_4$ conversion to syngas.

Figure 7:
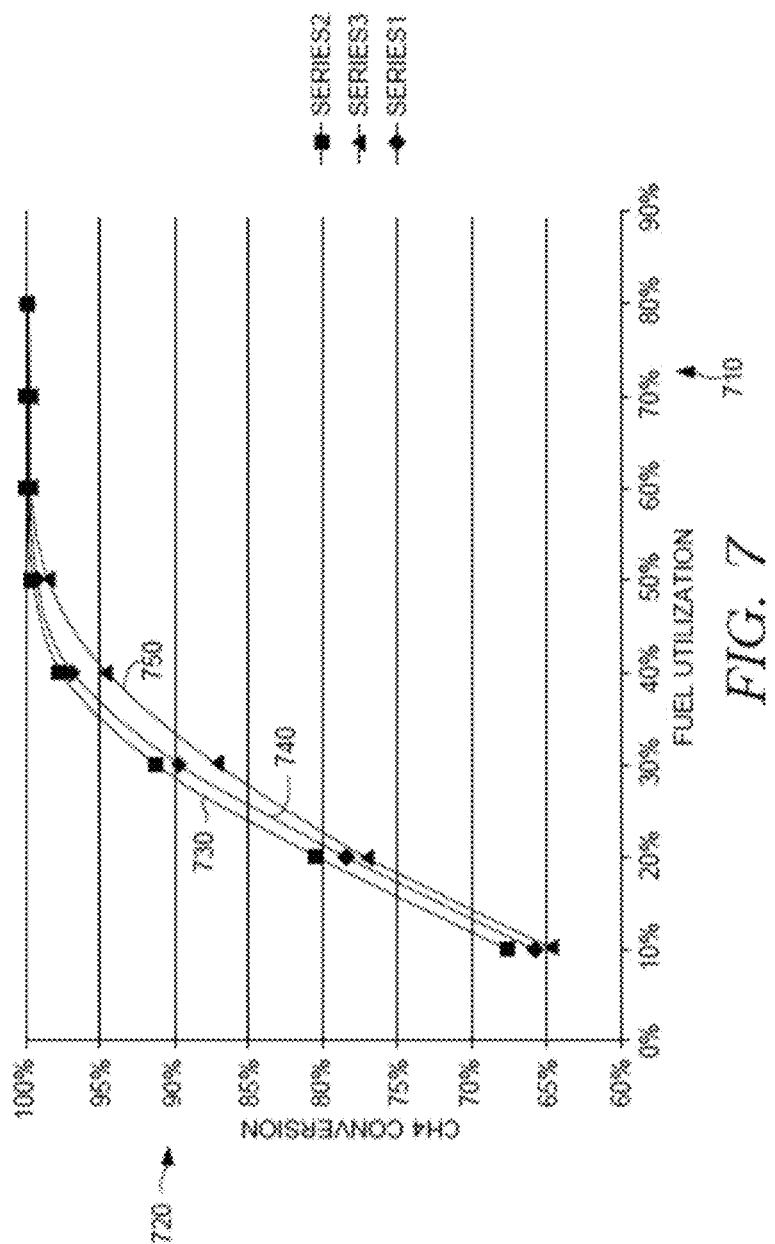
FIGS. 7 and 8 show examples of $CH_4$ conversion at different fuel cell operating voltages $V_A$.
Figure 8:
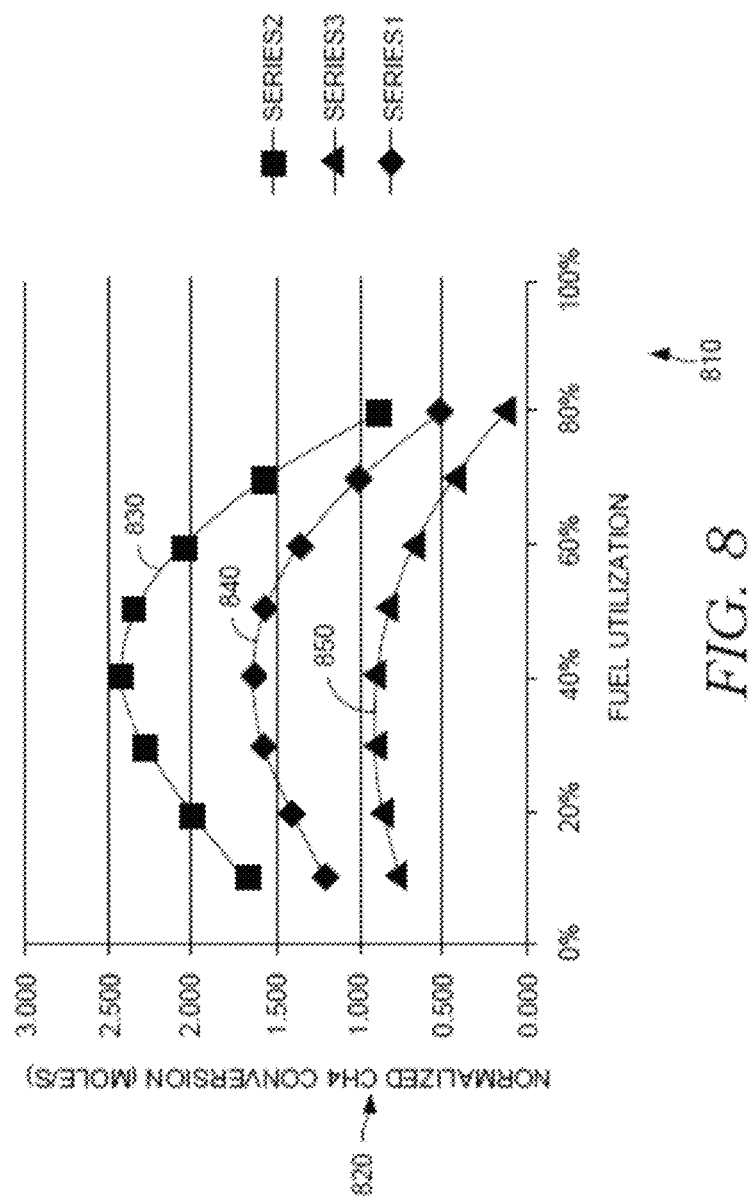

A series of simulations were performed to illustrate the benefits of operating a molten carbonate fuel cell according to the invention. Specifically, the simulations were performed to illustrate the benefit of running the fuel cell at lower voltage across different fuel utilizations. The impact of running the fuel cell at lower voltage and low fuel utilization is shown in FIGS. 7 and 8. FIG. 7 illustrates a model of the fuel cell in a representation analogous to FIG. 6-13 of the NETL Fuel Cell Handbook. The simulations used to produce the results shown in FIG. 7 were run at a constant $CH_4$ flow rate. FIG. 7 shows the conversion 720 that can occur at different fuel utilization 710 percentages for different operating voltages. At high voltage (0.8V) 750, as the fuel utilization is decreased, the $CH_4$ conversion also appeared to be decreased to a low level. As the voltage is lowered (to 0.7V, 740, and 0.6V, 730), the $CH_4$ conversion at each fuel utilization point modeled appeared to be higher than the corresponding conversion at 0.8V. While FIG. 7 shows only a few percentage increase in $CH_4$ conversion, the impact can actually be quite substantial, as illustrated in FIG. 8.

The simulations used to produce the results shown in FIG. 8 were not performed at a constant flow rate of $CH_4$, but at a constant fuel cell area instead. In FIG. 8, the same operation of the fuel cell was illustrated not on a percentage of $CH_4$ conversion basis, but on an absolute flow rate of $CH_4$ for a fixed fuel cell area. The x-axis 810 shows the fuel utilization and the y-axis 820 shows normalized $CH_4$ conversion. Plot 830 shows simulated results produced at 0.6V. Plot 840 shows the simulated results produced at 0.7V. Plot 850 shows the simulated results produced at 0.8V. As the fuel utilization is decreased, and especially as the voltage is decreased, the current density appeared to be increased by more than a factor of 5 for the data shown in FIGS. 7 and 8. As such, the power density can be increased by lowering the operating voltage under operating conditions consistent with aspects of the invention. The increased power density and lower voltage seems to be contrary to the affect achieved during conventional operations, where lower operating voltage typically results in lower power density. As shown in FIG. 8, the impact on total $CH_4$ conversion appeared significant: much higher conversion of $CH_4$, measured as an absolute flow rate, was achieved at lower fuel utilization when the voltage was decreased.

Additional Embodiments

Embodiment 1. A method for operating a molten carbonate fuel cell, the method comprising: introducing an anode fuel stream comprising reformable fuel into an anode inlet of an anode of a molten carbonate fuel cell; introducing a cathode inlet stream comprising $CO_2$ and $O_2$ into a cathode inlet of a cathode of the molten carbonate fuel cell; operating the molten carbonate fuel cell at a first operating condition to generate electrical power and at least 30 mW/cm² of waste heat, the first operating condition providing a current density of at least about 150 mA/cm²; generating an anode exhaust from an anode outlet of the molten carbonate fuel cell; and performing an effective amount of an endothermic reaction to maintain a temperature differential between the anode inlet and the anode outlet of about 100° C. or less.

Embodiment 2. A method for operating a molten carbonate fuel cell, the method comprising: introducing an anode fuel stream comprising reformable fuel into an anode inlet of an anode of a molten carbonate fuel cell; introducing a cathode inlet stream comprising $CO_2$ and $O_2$ into a cathode inlet of a cathode of the molten carbonate fuel cell; operating the molten carbonate fuel cell at a first operating condition to generate electricity, the first operating condition providing a current density of at least about 150 mA/cm², the first operating condition having a corresponding baseline operating condition; generating an anode exhaust from an anode outlet of the molten carbonate fuel cell; and performing an effective amount of an endothermic reaction to maintain a temperature differential between the anode inlet and the anode outlet of about 80° C. or less, wherein operating the molten carbonate fuel cell at the baseline operating condition would result in a temperature increase of at least about 100° C. between the anode inlet and the anode outlet, the baseline operating condition for the molten carbonate fuel cell being defined as an operating condition that is the same as the first operating condition except that the baseline operating condition comprises a fuel utilization of the anode of the molten carbonate fuel cell of about 75% and the anode fuel stream in the baseline operating condition comprises at least about 80 vol % of methane.

Embodiment 3. A method for operating a molten carbonate fuel cell, the method comprising: introducing an anode fuel stream comprising reformable fuel into an anode inlet of an anode of a molten carbonate fuel cell; introducing a cathode inlet stream comprising $CO_2$ and $O_2$ into a cathode inlet of a cathode of the molten carbonate fuel cell; operating the molten carbonate fuel cell at a first operating condition to generate electrical power at a first power density and waste heat, the first operating condition comprising a first anode inlet temperature, a first anode inlet flow rate, a first anode fuel partial pressure, a first anode water partial pressure, a first cathode inlet flow rate, a first cathode inlet $CO_2$ partial pressure, and a first cathode inlet $O_2$ partial pressure, the first operating condition having a corresponding maximum power operating condition; generating an anode exhaust from an anode outlet of the molten carbonate fuel cell; and performing an effective amount of an endothermic reaction to maintain a temperature differential between the anode inlet and the anode outlet of about 80° C. or less, wherein operating the fuel cell assembly at the maximum power operating condition would result in a power density that differs from the first power density by less than about 20%, the maximum power operating condition corresponding to an operating condition that generates the maximum power density for an operating condition that comprises the first anode inlet temperature, the first anode inlet flow rate, the first anode fuel partial pressure, the first anode water partial pressure, the first cathode inlet flow rate, the first cathode inlet $CO_2$ partial pressure, and the first cathode inlet $O_2$ partial pressure.

Embodiment 4. The method of Embodiment 3, wherein the power density at the maximum power operating condition differs from the first power density by less than about 15%.

Embodiment 5. The method of any of the above Embodiments, further comprising withdrawing a product stream from the molten carbonate fuel cell comprising one or more reaction products generated by performing the effective amount of the endothermic reaction.

Embodiment 6. The method of Embodiment 5, wherein the product stream is withdrawn from the molten carbonate fuel cell without passing through an anode of the molten carbonate fuel cell.

Embodiment 7. The method of any of the above Embodiments, wherein the molten carbonate fuel cell further comprises one or more integrated endothermic reaction stages.

Embodiment 8. The method of Embodiment 7, wherein at least one integrated endothermic reaction stage of the one or more integrated endothermic reaction stages comprises an integrated reforming stage, the anode fuel stream being passed through the integrated reforming stage prior to being introduced into the anode inlet of the anode of the molten carbonate fuel cell.

Embodiment 9. The method of Embodiment 7 or 8, wherein performing an effective amount of an endothermic reaction comprises reforming a reformable fuel.

Embodiment 10. The method of any of the above Embodiments, wherein performing an effective amount of an endothermic reaction comprises performing an endothermic reaction that consumes at least about 40% of the waste heat generated by operating the molten carbonate fuel cell at the first operating condition.

Embodiment 11. The method of any of the above Embodiments, wherein a temperature at the anode outlet is less than 50° C. greater than a temperature at the anode inlet.

Embodiment 12. The method of the above Embodiments, wherein the molten carbonate fuel cell is operated to generate waste heat of at least about 40 mW/cm$^2$ (e.g., at least about 50 mW/cm$^2$, or at least about 60 mW/cm$^2$).

Embodiment 13. The method of any of the above Embodiments, wherein the first operating condition provides a current density of at least about 200 mA/cm$^2$.

Embodiment 14. The method of any of the above Embodiments, wherein the molten carbonate fuel cell is operated at a voltage $V_A$ of less than about 0.7 Volts (e.g., about 0.67 Volts or less, or about 0.65 Volts or less).

Embodiment 15. The method of any of the above Embodiments, wherein no portion of the anode exhaust is directly or indirectly recycled to the anode, directly or indirectly recycled to the cathode, or a combination thereof.

Embodiment 16. The method of any of the above Embodiments, wherein less than 10 vol % of the anode exhaust is directly or indirectly recycled to the anode of the molten carbonate fuel cell or the cathode of the molten carbonate fuel cell.

Embodiment 17. The method of any of the above Embodiments, further comprising separating from the anode exhaust a $H_2$-containing stream, a syngas-containing stream, or a combination thereof.

Embodiment 18. The method of Embodiment 17, wherein less than 10 vol % of $H_2$ produced in the anode of the molten carbonate fuel cell in a single pass is directly or indirectly recycled to the anode of the molten carbonate fuel cell or the cathode of the molten carbonate fuel cell.

Embodiment 19. The method of Embodiment 17, wherein less than 10 vol % of the syngas-containing stream is directly or indirectly recycled to the anode of the molten carbonate fuel cell or the cathode of the molten carbonate fuel cell.

Examples

In an aspect of the invention, the waste heat generated by running the fuel cell at a high power density can be used to facilitate an endothermic reaction within an endothermic reaction stage integrated with the fuel cell. In some aspects, an integrated endothermic reaction stage can be defined as a stage that is heat integrated with one or more fuel cells, so that the integrated endothermic reaction stage can use the heat from the fuel cells as a heat source for the endothermic reaction. In an aspect, the waste heat generated can be approximately balanced with the endothermic reaction's heat demand to achieve a temperature differential between the anode inlet and outlet of approximately zero. Alternatively, a negative temperature differential can be achieved.

Several example simulations are provided below to illustrate performing an endothermic reaction to achieve a desired temperature differential from the anode inlet to the anode outlet. For these simulations, a fuel cell producing ~1 MW of electricity at a total electrical efficiency of about 50% was used. The fuel cell was simulated to operate at a $CH_4$ flow rate of ~2.5 mole/s.

The fuel cell's steam reforming reaction and water gas shift reaction consumed about 0.4 MW of heat. This combined reaction (reforming and water gas shift combined $CH_4+2H_2O\Rightarrow 4H_2+CO_2$) has been explained previously with reference to equation 3. The oxidation reaction produced about 1.0 MW of electricity and about 0.8 MW of heat. The oxidation reaction (anode $H_2$ oxidation $H_2+CO_3^{2-}\Rightarrow H_2O+CO_2+2e^-$) has been explained previously with reference to equation 4. The combustion of excess $H_2$ (and/or CO) in the cathode burner produced about 0.6 MW of heat. The net effect was the production of about 1.0 MW of electricity and $-0.4+0.8+0.6=\sim 1.0$ MW of heat, for an overall 50% approximate electrical efficiency. The oxidation reaction, the steam reforming, and the water gas shift reactions occurred internally to the fuel cell stack in this simulation (for a combined $-0.4+0.8=\sim 0.4$MW of heat generation), while the combustion in the cathode burner was external to the fuel cell stack. In this simulation, the net ~0.4MW of heat generated within the stack led to a temperature rise across the stack of about 75° C.

One or more endothermic reactions can be selected to consume some, all, or more than the ~0.4 MW of heat, thereby producing a temperature differential less than about 75° C. The dehydrogenation of ethane to ethylene, dehydrogenation of propane to propylene, and aromatization of hexane to benzene are non-limiting examples of endothermic reactions that individually or collectively may be used to consume the heat generated in the anode.

The dehydrogenation of ethane to ethylene within a fuel cell's integrated endothermic reaction stage was simulated. The dehydrogenation of ethane to ethylene required ~136.4 kJ/mol of heat. In the present simulation, ~2.9 mole/s of $C_2H_6$ were converted to $C_2H_4$ (and $H_2$) in the fuel cell's integrated endothermic reaction stage. In so doing, this endothermic reaction consumed the heat generated by the fuel cell, which resulted in an approximately isothermal operation, or T of zero across the stack. As a second variation, ~5.8 mole/s of $C_2H_6$ were converted to $C_2H_4$ (and $H_2$), which resulted in a net endothermic operation with a T of about −75° C.

The dehydrogenation of propane to propylene within a fuel cell's integrated endothermic reaction stage was also simulated. The dehydrogenation of propane to propylene required ~123.7 kJ/mol of heat. In the present simulation, ~3.2 mole/s of $C_3H_8$ were converted to $C_3H_6$ (and $H_2$) in the fuel cell's integrated endothermic reaction stage. In so doing, this endothermic reaction consumed the heat generated by the fuel cell, which resulted in an approximately isothermal operation, or T of zero across the stack. As a second variation, ~6.4 mole/s of $C_3H_6$ (and $H_2$) were converted to $C_3H_6$ (and $H_2$), which resulted in a net endothermic operation with a T of about −75° C.

The aromatization of hexane to benzene within a fuel cell's integrated endothermic reaction stage was also simulated. The aromatization of hexane to benzene required ~248.9 kJ/mol of heat. In the present simulation, ~1.6 mole/s of $C_6H_{14}$ were converted to $C_6H_6$ (and $4H_2$) in the fuel cell's integrated endothermic reaction stage. In so doing, this endothermic reaction consumed the heat generated by the fuel cell, which resulted in an approximately isothermal operation, or T of zero across the stack. As a second variation, ~3.2 mole/s of $C_6H_{14}$ were converted to $C_6H_6$ (and $4H_2$), which resulted in a net endothermic operation with a T of about −75° C.

These simple examples illustrate endothermic reactions that could be suitable for use with aspects of the invention. The first two examples represent the broad class of catalytic dehydrogenation chemistry that could be performed in a fuel cell's integrated endothermic reaction stage. The third example illustrates the broad class of chemistry known as "naphtha reforming", in which alkanes are converted to aromatics, with evolution of $H_2$. In addition to these examples, many other kinds of endothermic chemistry could be performed in a fuel cell's integrated endothermic reaction stage.

Although the present invention has been described in terms of specific embodiments, it is not so limited. Suitable alterations/modifications for operation under specific conditions should be apparent to those skilled in the art. It is therefore intended that the following claims be interpreted as covering all such alterations/modifications that fall within the true spirit/scope of the invention.

What is claimed is:

1. A method for operating a molten carbonate fuel cell, the method comprising:
    introducing an anode fuel stream comprising reformable fuel into an anode inlet of an anode of a molten carbonate fuel cell;
    introducing a cathode inlet stream comprising CO2 and O2 into a cathode inlet of a cathode of the molten carbonate fuel cell;
    operating the molten carbonate fuel cell at a first operating condition to generate electricity, the first operating condition providing a current density of at least about 150 mA/cm2, the first operating condition having a corresponding baseline operating condition;
    generating an anode exhaust from an anode outlet of the molten carbonate fuel cell; and
    performing an effective amount of an endothermic reaction to maintain a temperature differential between the anode inlet and the anode outlet of about 80° C. or less, wherein operating the molten carbonate fuel cell at the baseline operating condition would result in a temperature increase of at least about 100° C. between the anode inlet and the anode outlet, the baseline operating condition for the molten carbonate fuel cell being defined as an operating condition that is the same as the first operating condition except that the baseline operating condition comprises a fuel utilization of the anode of the molten carbonate fuel cell of about 75% and the anode fuel stream in the baseline operating condition comprises at least about 80 vol % of methane.

2. A method for operating a molten carbonate fuel cell, the method comprising:
    introducing an anode fuel stream comprising reformable fuel into an anode inlet of an anode of a molten carbonate fuel cell;
    introducing a cathode inlet stream comprising CO2 and O2 into a cathode inlet of a cathode of the molten carbonate fuel cell;
    operating the molten carbonate fuel cell at a first operating condition to generate electrical power at a first power density and waste heat, the first operating condition comprising a first anode inlet temperature, a first anode inlet flow rate, a first anode fuel partial pressure, a first anode water partial pressure, a first cathode inlet flow rate, a first cathode inlet CO2 partial pressure, and a first cathode inlet O2 partial pressure, the first operating condition having a corresponding maximum power operating condition;
    generating an anode exhaust from an anode outlet of the molten carbonate fuel cell; and
    performing an effective amount of an endothermic reaction to maintain a temperature differential between the anode inlet and the anode outlet of about 80° C. or less, wherein operating the fuel cell assembly at the maximum power operating condition would result in a power density that differs from the first power density by less than about 20%, the maximum power operating condition corresponding to an operating condition that generates the maximum power density for an operating condition that comprises the first anode inlet temperature, the first anode inlet flow rate, the first anode fuel partial pressure, the first anode water partial pressure, the first cathode inlet flow rate, the first cathode inlet CO2 partial pressure, and the first cathode inlet O2 partial pressure.

3. The method of claim 2, wherein the power density at the maximum power operating condition differs from the first power density by less than about 15%.

4. The method of claim 1, further comprising withdrawing a product stream from the molten carbonate fuel cell comprising one or more reaction products generated by performing the effective amount of the endothermic reaction.

5. The method of claim 4, wherein the product stream is withdrawn from the molten carbonate fuel cell without passing through an anode of the molten carbonate fuel cell.

6. The method of claim 1, wherein the molten carbonate fuel cell further comprises one or more integrated endothermic reaction stages.

7. The method of claim 6, wherein at least one integrated endothermic reaction stage of the one or more integrated endothermic reaction stages comprises an integrated reforming stage, the anode fuel stream being passed through the integrated reforming stage prior to being introduced into the anode inlet of the anode of the molten carbonate fuel cell.

8. The method of claim 6, wherein performing an effective amount of an endothermic reaction comprises reforming a reformable fuel.

9. The method of claim 2, wherein performing an effective amount of an endothermic reaction comprises performing an endothermic reaction that consumes at least about 40% of the waste heat generated by operating the molten carbonate fuel cell at the first operating condition.

10. The method of claim 1, wherein a temperature at the anode outlet is less than 50° C. greater than a temperature at the anode inlet.

11. The method of claim 1, wherein the molten carbonate fuel cell is operated to generate waste heat of at least about 40 mW/cm2.

12. The method of claim 1, wherein the first operating condition provides a current density of at least about 200 mA/cm2.

13. The method of claim 1, wherein the molten carbonate fuel cell is operated at a voltage VA of less than about 0.7 Volts.

14. The method of claim 1, wherein no portion of the anode exhaust is directly or indirectly recycled to the anode, directly or indirectly recycled to the cathode, or a combination thereof.

15. The method of claim 1, wherein less than 10 vol % of the anode exhaust is directly or indirectly recycled to the anode of the molten carbonate fuel cell or the cathode of the molten carbonate fuel cell.

16. The method of claim 1, further comprising separating from the anode exhaust a H2-containing stream, a syngas-containing stream, or a combination thereof.

17. The method of claim 16, wherein less than 10 vol % of H2 produced in the anode of the molten carbonate fuel cell in a single pass is directly or indirectly recycled to the anode of the molten carbonate fuel cell or the cathode of the molten carbonate fuel cell.

18. The method of claim 16, wherein less than 10 vol % of the syngas-containing stream is directly or indirectly recycled to the anode of the molten carbonate fuel cell or the cathode of the molten carbonate fuel cell.

* * * * *